US009133443B2

(12) United States Patent
Wong et al.

(10) Patent No.: US 9,133,443 B2
(45) Date of Patent: Sep. 15, 2015

(54) MUTANT ENZYMES

(75) Inventors: Luet Lok Wong, Oxford (GB); Stephen Graham Bell, Oxford (GB); Christopher Whitehouse, Oxford (GB)

(73) Assignee: Isis Innovation Limited, Oxford (GB)

(*) Notice: Subject to any disclaimer, the term of this patent is extended or adjusted under 35 U.S.C. 154(b) by 588 days.

(21) Appl. No.: 12/681,868

(22) PCT Filed: Oct. 8, 2008

(86) PCT No.: PCT/GB2008/003407
§ 371 (c)(1),
(2), (4) Date: May 18, 2010

(87) PCT Pub. No.: WO2009/047498
PCT Pub. Date: Apr. 16, 2009

(65) Prior Publication Data
US 2010/0240106 A1    Sep. 23, 2010

(30) Foreign Application Priority Data
Oct. 8, 2007 (GB) .................................. 0719620.7

(51) Int. Cl.
C12P 7/64 (2006.01)
C07H 21/04 (2006.01)
C12N 15/52 (2006.01)
C12N 9/02 (2006.01)

(52) U.S. Cl.
CPC .................................. *C12N 9/0071* (2013.01)

(58) Field of Classification Search
CPC ........... C12Q 1/6883; C12Q 2600/158; C12Q 1/6886; C12Q 2600/136; C12Q 2600/106; C12Q 1/6809; C12Q 1/26; C12Q 2600/156; C12N 9/0071; C12N 15/52; C12N 9/0004; C12N 9/0069; C12N 9/0006; C12N 9/0073; C07K 14/00; C07K 14/195; C07K 14/32; C12P 7/04; C12P 7/42; C12P 7/02; C12P 7/18
See application file for complete search history.

(56) References Cited

U.S. PATENT DOCUMENTS

| 5,763,237 | A | 6/1998 | Savithiry et al. ............... 435/148 |
| 6,100,074 | A | 8/2000 | Flitsch et al. .................. 435/189 |
| 6,117,661 | A | 9/2000 | Wong et al. .................... 435/189 |
| 6,794,168 | B1 | 9/2004 | Wong et al. .................... 435/189 |
| 7,211,420 | B1 | 5/2007 | Wong et al .................... 435/189 |
| 7,531,335 | B1 | 5/2009 | Hauer et al. ................... 435/189 |
| 7,960,155 | B1 | 6/2011 | Hauer et al. |
| 2003/0100744 | A1 | 5/2003 | Farinas et al. .................. 435/189 |
| 2005/0037411 | A1 | 2/2005 | Arnold et al. .................. 435/189 |
| 2005/0059045 | A1* | 3/2005 | Arnold et al. ..................... 435/6 |
| 2005/0059128 | A1 | 3/2005 | Arnold et al. |
| 2005/0202419 | A1 | 9/2005 | Cirino et al. ................. 536/23.2 |
| 2009/0209010 | A1* | 8/2009 | Fasan et al. .................... 435/106 |

FOREIGN PATENT DOCUMENTS

| AU | 780694 | 4/2005 |
| CN | 1365393 A | 8/2002 |
| EP | 0334841 | 9/1993 |
| EP | 1470219 | 10/2004 |
| EP | 1639091 | 3/2006 |
| EP | 1660646 | 5/2006 |
| GB | 2 294 692 | 5/1996 |
| GB | 2 306 485 | 5/1997 |
| JP | 3061490 B2 | 7/2000 |
| JP | 2003521889 A | 7/2003 |
| WO | WO 88/01641 | 3/1988 |
| WO | WO 94/01564 | 1/1994 |
| WO | WO 96/14419 | 5/1996 |
| WO | WO 97/16553 | 5/1997 |
| WO | WO 00/31273 | 6/2000 |
| WO | 0107574 A2 | 2/2001 |
| WO | 02083868 A2 | 10/2002 |
| WO | 03/008563 A2 | 1/2003 |
| WO | 2004038655 A2 | 5/2004 |
| WO | 2005017105 A2 | 2/2005 |
| WO | 2005017106 A2 | 2/2005 |
| WO | WO 2005/017116 | 2/2005 |
| WO | 2005083100 A1 | 9/2005 |
| WO | 2006105082 A2 | 10/2006 |
| WO | 2009047498 A2 | 4/2009 |

OTHER PUBLICATIONS

Oliver Lentz, Klonierung, expression and charakterisierung der cytochrome P450-monooxygenase CYP102A3 aus *Bacillus subtilis* sowie veranderung ihrer regioselekivitat durch gerichtete evolution, a Doctoral Thesis, Sep. 2004, Institut Fur Technische Biochemie Der Universitat Stuttgart, Germany.*
Appel et al., "A P450 BM-3 mutant hydroxylates alkanes, cycloalkanes, arenes and heteroarenes," *J. Biotechnol.*, 88:167-171, 2001.
Atkins et al., "Molecular Recognition in Cytochrome P-450: Alteration of Regioselective Alkane Hydroxylation via Protein Engineering," *J Am. Chem. Soc.*, 111:2715-2717, 1989.
Atkins et al., "The Roles of Active Site Hydrogen Bonding in Cytochrome P-450 cam as Revealed by Site-directed Mutagenesis," *J. Biol. Chem.*, 263:18842-18849, 1988.
Bogaards et al., "Human Cytochrome P450 Enzyme Selectivities in the Oxidation of Chlorinated Benzenes," *Toxicology and Applied Pharmacology*, 132:44-52, 1995.
Carmichael and Wong, "Protein engineering of *Bacillus megaterium* CYP102," *Eur. J Biochem.*, 268:3117-3125, 2001.
Cirino and Arnold, "A self-sufficient peroxide-driven hydroxylation biocatalyst," *Angew. Chem. Int. Ed.*, 42:3299-3301, 2003.
Cowart et al., "Structural determinants of active site binding affinity and metabolism by cytochrome P450 BM-3," *Arch. Biochem. Biophys.*, 387:117-124, 2001.
Di Nardo et al., "Wild-type CYP102A1 as a biocatalyst: turnover of drugs usually metabolized by human liver enzymes," *J Biol Inorg Chem*, 12:313-323, 2007.

(Continued)

*Primary Examiner* — Iqbal H Chowdhury
(74) *Attorney, Agent, or Firm* — Norton Rose Fulbright US LLP

(57) ABSTRACT

This invention relates to mutant enzymes with enhanced properties and processes for oxidation of organic compound substrates using such enzymes.

12 Claims, 2 Drawing Sheets

(56) References Cited

OTHER PUBLICATIONS

Di Primo et al., "Mutagenesis of a Single Hydrogen Bond in Cytochrome P-450 Alters Cation Binding and Heme Solvation," *J. Biol. Chem.*, 265:5361-5363, 1990.
Dong and Porter, "Coexpression of Mammalian Cytochrome P450 and Reductase in *Escherichia coli*," *Archives of Biochemistry and Biophysics*, 327:254-259, 1996.
England et al., "The oxidation of naphthalene and pyrene by cytochrome P450$_{cam}$," *FEBS Letters*, 424:271-274, 1998.
Filipovic et al., "Ethylbenzene Hydroxylation by Cytochrome P450$_{cam}$," *Biochemical and Biophysical Research Communications*, 189:488-495, 1992.
Gilardi et al., "Molecular lego: design of molecular assemblies of P450 enzymes for nanobiotechnology," *Biosensors & Bioelectronics*, 17:133-145, 2002.
Glieder et al., "Laboratory evolution of a soluble, self-sufficient, highly active alkane hydroxylase," *Nat. Biotechnol.*, 20, 1135-1139, 2002.
Gooch et al., "Effects of ortho- and Non-ortho-Substituted Polychlorinated Biphenyl Congeners on the Hepatic Monooxygenase System in Scup (*Stenotomus chrysops*)," *Toxicol. Appl. Pharmacol.*, 98:422-433, 1989.
Gotoh, "Substrate Recognition Sites in Cytochrome P450 Family 2 (CYP2) Proteins Inferred from Comparative Analyses of Amino Acid and Coding Nucleotide Sequences," *J. Biol. Chem*, 267:83-90, 1992.
Graham-Lorence et al., "An active site substitution, F87V, converts cytochrome P450 BM-3 into a regio- and stereoselective (14S, 15R)-arachidonic acid epoxygenase," *J. Biol. Chem.*, 272:1127-1135, 1997.
Hegg et al., "Herbicide-Degrading a-Keto Acid-Dependent Enzyme TfdA: Metal Coordination Environment and Mechanistic Insights," *Biochemistry*, 38:16714-16726, 1999.
Jones et al., "Engineering the selectivity of aliphatic C-H bond oxidation catalysed by cytochrome P450cam," *Chem. Communications*, 21:2413-2414, 1996.
Jones et al., "The oxidation of polychlorinated benezenes by genetically engineered cytochrome P450$_{cam}$: potential applications in bioremediation," *Chem. Commun.*, 3:247-248, 2000.
Kubo et al., "Enantioselective epoxidation of terminal alkenes to (R)- and (S)-epoxides by engineered cytochromes P450 BM-3," *Chemistry Eur. J.*, 12:1216-1220, 2006.
Li et al., "Directed evolution of the fatty-acid hydroxylase P450 BM-3 into an indole-hydroxylating catalyst," *Chem. Eur. J.*, 6:1531-1536, 2000.
Li et al., "Engineering cytochrome P450 BM-3 for oxidation of polycyclic aromatic hydrocarbons," *Appl. Environ. Microbiol.*, 67:5735-5739, 2001.
Li et al., "Rational evolution of a medium chain-specific cytochrome P-450 BM-3 variant," *Biochim. Biophys. Acta*, 1545:114-121, 2001.
Loida et al., "Molecular Recognition in Cytochrome P-450: Mechanism for the Control of Uncoupling Reactions," *Biochemistry*, 32:11530-11538, 1993.
Lussenburg et al., "Evaluation of alkoxyresorufins as fluorescent substrates for cytochrome P450 BM3 and site-directed mutants," *Anal Biochem*, 341:148-155, 2005.
Mayes et al., "Decreased substrate affinity upon alteration of the substrate-docking region in cytochrome P450$_{BM-3}$," *FEBS Lett.*, 414:213-218, 1997.
Meinhold et al., "Direct conversion of ethane to ethanol by engineered cytochrome P450 BM3," *ChemBioChem*, 6:1765-1768, 2005.
Meinhold et al., "Engineering Cytochrome P450 BM3 for Terminal Alkane Hydroxylation," *Adv Synth Catal*, 348:763-772, 2006.
Mueller et al., "Twenty Five Years of P450cam Research," In: CytoChrome P450: Structure, Mechanism and Biochemistry, 2nd Ed. Ortiz de Montellano Ed., Plenum Press, New York, pp. 83-124, 1995.
Murataliev et al., "Chimeragenesis of the fatty acid binding site of cytochrome P450BM3. Replacement of residues 73-84 with the homologous residues from the insect cytochrome P450 CYP4C7," *Biochemistry*, 43:1771-1780, 2004.
Nickerson et al., "The catalytic activity of cytochrome P450$_{cam}$ towards styrene oxidation is increased by site-spcific mutagenesis," *FEBS Letters*, 405:153-156, 1997.
Noble et al., "Roles of key active-site residues in flavocytochrome P450 BM3," *Biochem. J.*, 339:371-379, 1999.
Oliver et al., "A single mutation in cytochrome P450 BM3 changes substrate orientation in a catalytic intermediate and the regiospecificity of hydroxylation," *Biochemistry*, 36:1567-1572, 1997.
Oliver et al., "Engineering the substrate specificity of *Bacillus megaterium* cytochrome P-450 BM3: hydroxylation of alkyl trimethylammonium compounds," *Biochem. J.*, 327:537-544, 1997.
Ost et al., "Rational re-design of the substrate binding site of flavocytochrome P450 BM3," *FEBS Lett*, 486:173-177, 2000.
PCT International Search Report issued in International Application No. PCT/GB99/03873, mailed May 23, 2000.
Peters et al., "Regio- and enantioselective alkane hydroxylation with engineered cytochromes P450 BM-3," *J. Am. Chem. Soc.*, 125:13442-13450, 2003.
Schulze et al., "Activation of phosphorothionate pesticides based on a cytochrome P450 BM-3 (CYP102 A1) mutant for expanded neurotoxin detection in food using acetylcholinesterase biosensors," *Anal. Chem.*, 76:1720-1725, 2004.
Schwaneberg et al., "A continuous spectrophotometric assay for P450 BM-3, a fatty acid hydroxylating enzyme, and its mutant F87A," *Anal. Biochem.*, 269:359-366, 1999.
Shimoji et al., "Design of a Novel P450: A Functional Bacterial—Human cytochrome P450 Chimera," *Biochemistry*, 37:8848-8852, 1998.
Sibbesen et al., "Putidaredoxin Reductase-Putadaredoxin-Cytochrome P450$_{cam}$ Triple Fusion Protein," *J. Biol. Chem.*, 271:22462-22469, 1996.
Sowden et al., "Biotransformation of the sesquiterpene (+)-valencene by cytochrome P450$_{cam}$ and P450$_{BM-3}$," *Org. Biomol. Chem.*, 3:57-64, 2005.
Tee and Schwaneberg, "A screening system for the directed evolution of epoxygenases: importance of position 184 in P450BM3 for stereoselective styrene epoxidation," *Angew Chem Int Ed*, 45:5380-5383, 2006.
Tuck et al., "Active Sites of the Cytochrome p450$_{cam}$ (CYP101) F89787W and F87A Mutants," *J. Biol. Chem.*, 268:269-275, 1993.
Urlacher et al., "Biotransformation of β-ionone by engineered cytochrome P450 BM-3," *Appl. Microbiol. Biotechnol.*, 70:53-59, 2006.
van Vugt-Lussenburg et al., "Heterotropic and homotropic cooperativity by a drug-metabolising mutant of cytochrome P450 BM3," *Biochem. Biophys. Res. Commun.*, 346:810-818, 2006.
van Vugt-Lussenburg et al., "Identification of critical residues in novel drug metabolizing mutants of cytochrome P450 BM3 using random mutagenesis," *J. Med. Chem.*, 50:455-461, 2007.
White et al., "Regioselectivity in the Cytochromes P-450: Control by Protein Constraints and by Chemical Reactivities," *Archives of Biochemistry and Biophysics*, 228:493-502, 1984.
Wong et al., "Sensitive assay for laboratory evolution of hydroxylases toward aromatic and heterocyclic compounds," *J Biomol Screen*, 10:246-252, 2005.
Chang et al.; "Homology Modeling and Substrate Binding Study of Human CYP4A11 Enzyme"; Molecular Research Institute, Proteins; Feb. 15, 1999; 34 (3); 403-15.
Li et al.; "The Structure of the Cytochrome p450BM-3 Haem Domain Complexed with the Fatty Acid Substrate, Palmitoleic Acid"; (1997); Nature Structural Biology 4; 140-146.
Munro et al.; "Cytochrome P450—redox partner fusion enzymes." Mar. 2007; Biochim Biophys Acta.; 1770 (3):345-59.
Whitehouse et al.; "Evolved CYP102A1 (P450BM3) variants oxidise a range of non-natural substrates and offer new selectivity options" 2008; Chem. Commun.; 966-968.
Whitehouse et al; "Desaturation of alkylbenzenes by cytochrome P450(BM3) (CYP102A1)"; 2008; Chemistry 2008;14(35).
Yun et al.; "The bacterial P450 BM3: a prototype for a biocatalyst with human P450 activities"; Jul. 2007, Trends in Biotechnology; vol. 25, Issue 7, pp. 289-298.

(56) References Cited

OTHER PUBLICATIONS

International Preliminary Report on Patentability, issued Apr. 13, 2010 (published Apr. 13, 2010) during the prosecution of International Application No. PCT/GB2008/003407.
Written Opinion, issued Apr. 8, 2010 during the prosecution of International Application No. PCT/GB2008/003407.
International Search Report issued Jun. 4, 2009 (published Apr. 9, 2009) during the prosecution of International Application No. PCT/GB2008/003407.
European Patent Office, Patent Abstracts of Japan, Publication date Mar. 18, 1991; Application No. 01197296.
Examiner's Search Report dated Feb. 7, 2008.
Chen, Mike M.Y., et. al.; "Comparison of Random Mutagenesis and Semi-Rational Designed Libraries for Improved Cytochrome P450 BM3-catalyzed Hydroxylation of Small Alkanes"; Protein Engineering, Design & Selection, pp. 1-8; 2012.
Whitehouse, Christopher, J.C., et. al.; Structural Basis for the Properties of Two Single-Site Proline Mutants of CYP102A1 ($P450_{BM3}$); ChemBioChem 2010, vol. 11, pp. 2549-2556.
Kille, Sabrina, et. al.; "Regio- and Stereoselectivity of P450-catalysed Hydroxylation of Steroids Controlled by Laboratory Evolution"; Nature Chemistry, vol. 3, Sep. 2011; pp. 738-743.
Cirino, Patrick C.; "Laboratory Evolution of Cytochrome P450 Peroxygenase Activity"; Thesis; California Institute of Technology, 2004.
Irene Axarli, et al., "Engineering the substrate specificity of cytochrome P450 CYP102A2 by directed evolution: production of an efficient enzyme for bioconversion of fine chemicals"; Laboratory of Enzyme Technology, Department of Agricultural Biotechnology, Biomolecular Engineering 22 (2005) 81-88.
Giovanna Di Nardo et al., "Wild-type CYP102A1 as a biocatalyst turnover of drugs usually metabolised by human liver enzymes", JBIC Journal of Biological Inorganic Chemistry, Springr, Berlin, DE, vol. 12, No. 3, pp. 313-323.
Huang et al., "Filling a hole in cytochrome P450 BM3 improves substrate binding and catalytic efficiency" J Mol Biol (2007) 373, 633-651.
Watanabe et al, "Oxidation of acyclic monoterpenes by P450 BM-3 monooxygenase: influence of the substrate E/Z-isomerism on enzyme chemo- and regioselectivity" Tetrahedron 63 (2007) 9413-9422.
Maurer et al, "Catalytic Hydroxylation in Biphasic Systems using CYP102A1 Mutants" Adv Synth Catal 2005, 347, 1090-1098.
Mowat et al, "Structures of Mutant Forms of the Heme Domain of Flavocytochrome P450 BM3", Annual Report 2004, Mar. 13, 2007.
Database UniProt (online) Sep. 13, 2007, "SubName: Full=YrhJ", Database accession No. A7Z710.
Eiben et al: "Preparative use of Isolated CYP102 monooxygenases—a critical appraisal" Journal of Biotechnology 124 (2006) 662-669.
Whitehouse et al., A Highly Active Single-Mutation Variant of P450BM3 (CYP102A1), ChemBioChem 2009, 10, 1654-1656.
Rupasinghe et al., "The cytochrome P450 gene family CYP157 does not contain EXXR in the K-helix reducing the absolute conserved P450 residues to a single cysteine" FEBS Letters 580 (2006) 6338-6342.
Nelson et al, "P450 superfamily: update on new sequences, gene mapping, accession numbers and nomenclature", Pharmacogenetics (1996) 6 1-42.
Lentz et al.,"Altering the Regioselectivity of Cytochrome P450 CYP102A3 of *Bacillus subtilis* by Using a New Versatile Assay System", ChemBioChem 2006, 7, 345-350.
Lentz et al., "Substrate specificity of native and mutated cytochrome P450 (CYP102A3) from *Bacillus subtilis*", J Biotech 108 (2004) 41-49.
Bloom et al.,"Protein stability promotes evolvability", PNAS, Apr. 2006, vol. 103, No. 15, 5869-5874.
Damsten et al., "Application of drug metabolising mutants of cytochrome P450 BM3 (CYP102A1) as biocatalysts for the generation of reactive metabolites", Chemico-Biological Interactions 171 (2008) 96-107.
Munzer et al., "Stereoselective hydroxylation of an achiral cyclopentanecarboxylic acid derivative using engineered P450s BM-3", Chem Commun 2005, 2597-2599.
Stjernschantz et al, "Structural rationalization of novel drug metabolizing mutants of cytochrome P450 BM3", Proteins 2008, 71, 336-352.

* cited by examiner

SEQUENCE LISTING

<160> NUMBER OF SEQ ID NOS: 16

<210> SEQ ID NO 1
<211> LENGTH: 3144
<212> TYPE: DNA
<213> ORGANISM: Bacillus megaterium
<220> FEATURE:
<221> NAME/KEY: CDS
<222> LOCATION: (1)..(3144)

<400> SEQUENCE: 1

```
aca att aaa gaa atg cct cag cca aaa acg ttt gga gag ctt aaa aat       48
Thr Ile Lys Glu Met Pro Gln Pro Lys Thr Phe Gly Glu Leu Lys Asn
1               5                   10                  15 tta ccg tta tta aac aca gat aaa ccg gtt caa gct ttg atg aaa att      96
Leu Pro Leu Leu Asn Thr Asp Lys Pro Val Gln Ala Leu Met Lys Ile
                20                  25                  30 gcg gat gaa tta gga gaa atc ttt aaa ttc gag gcg cct ggt cgt gta     144
Ala Asp Glu Leu Gly Glu Ile Phe Lys Phe Glu Ala Pro Gly Arg Val
            35                  40                  45 acg cgc tac tta tca agt cag cgt cta att aaa gaa tgc gat gaa tca     192
Thr Arg Tyr Leu Ser Ser Gln Arg Leu Ile Lys Glu Cys Asp Glu Ser
        50                  55                  60
```

-continued

```
cgc ttt gat aaa aac tta agt caa gcg gca ctt aaa ttt gta cgt gat        240
Arg Phe Asp Lys Asn Leu Ser Gln Ala Ala Leu Lys Phe Val Arg Asp
 65                  70                  75                  80 ttt gca gga gac ggg tta ttt aca agc tgg acg cat gaa aaa aat tgg        288
Phe Ala Gly Asp Gly Leu Phe Thr Ser Trp Thr His Glu Lys Asn Trp
                 85                  90                  95 aaa aaa gcg cat aat atc tta ctt cca agc ttc agt cag cag gca atg        336
Lys Lys Ala His Asn Ile Leu Leu Pro Ser Phe Ser Gln Gln Ala Met
            100                 105                 110 aaa ggc tat cat gcg atg atg gtc gat atc gcc gtg cag ctt gtt caa        384
Lys Gly Tyr His Ala Met Met Val Asp Ile Ala Val Gln Leu Val Gln
        115                 120                 125 aag tgg gag cgt cta aat gca gat gag cat att gaa gta ccg gaa gac        432
Lys Trp Glu Arg Leu Asn Ala Asp Glu His Ile Glu Val Pro Glu Asp
130                 135                 140 atg aca cgt tta acg ctt gat aca att ggt ctt tgc ggc ttt aac tat        480
Met Thr Arg Leu Thr Leu Asp Thr Ile Gly Leu Cys Gly Phe Asn Tyr
145                 150                 155                 160 cgc ttt aac agc ttt tac cga gat cag cct cat cca ttt att aca agt        528
Arg Phe Asn Ser Phe Tyr Arg Asp Gln Pro His Pro Phe Ile Thr Ser
                165                 170                 175 atg gtc cgt gca ctg gat gaa gca atg aac aag ctg cag cga gca aat        576
Met Val Arg Ala Leu Asp Glu Ala Met Asn Lys Leu Gln Arg Ala Asn
            180                 185                 190 cca gac gac cca gct tat gat gaa aac aag cgc cag ttt caa gaa gat        624
Pro Asp Asp Pro Ala Tyr Asp Glu Asn Lys Arg Gln Phe Gln Glu Asp
        195                 200                 205 atc aag gtg atg aac gac cta gta gat aaa att att gca gat cgc aaa        672
Ile Lys Val Met Asn Asp Leu Val Asp Lys Ile Ile Ala Asp Arg Lys
210                 215                 220 gca agc ggt gaa caa agc gat gat tta tta acg cat atg cta aac gga        720
Ala Ser Gly Glu Gln Ser Asp Asp Leu Leu Thr His Met Leu Asn Gly
225                 230                 235                 240 aaa gat cca gaa acg ggt gag ccg ctt gat gac gag aac att cgc tat        768
Lys Asp Pro Glu Thr Gly Glu Pro Leu Asp Asp Glu Asn Ile Arg Tyr
                245                 250                 255 caa att att aca ttc tta att gcg gga cac gaa aca aca agt ggt ctt        816
Gln Ile Ile Thr Phe Leu Ile Ala Gly His Glu Thr Thr Ser Gly Leu
            260                 265                 270 tta tca ttt gcg ctg tat ttc tta gtg aaa aat cca cat gta tta caa        864
Leu Ser Phe Ala Leu Tyr Phe Leu Val Lys Asn Pro His Val Leu Gln
        275                 280                 285 aaa gca gca gaa gaa gca gca cga gtt cta gta gat cct gct cca agc        912
Lys Ala Ala Glu Glu Ala Ala Arg Val Leu Val Asp Pro Ala Pro Ser
290                 295                 300 tac aaa caa gtc aaa cag ctt aaa tat gtc ggc atg gtc tta aac gaa        960
Tyr Lys Gln Val Lys Gln Leu Lys Tyr Val Gly Met Val Leu Asn Glu
305                 310                 315                 320 gcg ctg cgc tta tgg cca act gct cct gcg ttt tcc cta tat gca aaa       1008
Ala Leu Arg Leu Trp Pro Thr Ala Pro Ala Phe Ser Leu Tyr Ala Lys
                325                 330                 335 gaa gat acg gtg ctt gga gga gaa tat cct tta gaa aaa ggc gac gaa       1056
Glu Asp Thr Val Leu Gly Gly Glu Tyr Pro Leu Glu Lys Gly Asp Glu
            340                 345                 350 cta atg gtt ctg att cct cag ctt cac cgt gat aaa aca att tgg gga       1104
Leu Met Val Leu Ile Pro Gln Leu His Arg Asp Lys Thr Ile Trp Gly
        355                 360                 365 gac gat gtg gaa gag ttc cgt cca gag cgt ttt gaa aat cca agt gcg       1152
Asp Asp Val Glu Glu Phe Arg Pro Glu Arg Phe Glu Asn Pro Ser Ala
```

-continued

```
            370                 375                 380
att ccg cag cat gcg ttt aaa ccg ttt gga aac ggt cag cgt gcg tgt        1200
Ile Pro Gln His Ala Phe Lys Pro Phe Gly Asn Gly Gln Arg Ala Cys
385                 390                 395                 400 atc ggt cag cag ttc gct ctt cat gaa gca acg ctg gta ctt ggt atg        1248
Ile Gly Gln Gln Phe Ala Leu His Glu Ala Thr Leu Val Leu Gly Met
                405                 410                 415 atg cta aaa cac ttt gac ttt gaa gat cat aca aac tac gag ctg gat        1296
Met Leu Lys His Phe Asp Phe Glu Asp His Thr Asn Tyr Glu Leu Asp
    420                 425                 430 att aaa gaa act tta acg tta aaa cct gaa ggc ttt gtg gta aaa gca        1344
Ile Lys Glu Thr Leu Thr Leu Lys Pro Glu Gly Phe Val Val Lys Ala
435                 440                 445 aaa tcg aaa aaa att ccg ctt ggc ggt att cct tca cct agc act gaa        1392
Lys Ser Lys Lys Ile Pro Leu Gly Gly Ile Pro Ser Pro Ser Thr Glu
                450                 455                 460 cag tct gcc aaa aaa gca cgc aaa aag gca gaa aac gct cat aat acg        1440
Gln Ser Ala Lys Lys Ala Arg Lys Lys Ala Glu Asn Ala His Asn Thr
465                 470                 475                 480 ccg ctg ctt gtg cta tac ggt tca aat atg gga aca gct gaa gga acg        1488
Pro Leu Leu Val Leu Tyr Gly Ser Asn Met Gly Thr Ala Glu Gly Thr
                485                 490                 495 gcg cgt gat tta gca gat att gca atg agc aaa gga ttt gca ccg cag        1536
Ala Arg Asp Leu Ala Asp Ile Ala Met Ser Lys Gly Phe Ala Pro Gln
                500                 505                 510 gtc gca acg ctt gat tca cac gcc gga aat ctt ccg cgc gaa gga gct        1584
Val Ala Thr Leu Asp Ser His Ala Gly Asn Leu Pro Arg Glu Gly Ala
                515                 520                 525 gta tta att gta acg gcg tct tat aac ggt cat ccg cct gat aac gca        1632
Val Leu Ile Val Thr Ala Ser Tyr Asn Gly His Pro Pro Asp Asn Ala
530                 535                 540 aag caa ttt gtc gac tgg tta gac caa gcg tct gct gat gaa gta aaa        1680
Lys Gln Phe Val Asp Trp Leu Asp Gln Ala Ser Ala Asp Glu Val Lys
545                 550                 555                 560 ggc gtt cgc tac tcc gta ttt gga tgc ggc gat aaa aac tgg gct act        1728
Gly Val Arg Tyr Ser Val Phe Gly Cys Gly Asp Lys Asn Trp Ala Thr
                565                 570                 575 acg tat caa aaa gtg cct gct ttt atc gat gaa acg ctt gcc gct aaa        1776
Thr Tyr Gln Lys Val Pro Ala Phe Ile Asp Glu Thr Leu Ala Ala Lys
                580                 585                 590 ggg gca gaa aac atc gct gac cgc ggt gaa gca gat gca agc gac gac        1824
Gly Ala Glu Asn Ile Ala Asp Arg Gly Glu Ala Asp Ala Ser Asp Asp
                595                 600                 605 ttt gaa ggc aca tat gaa gaa tgg cgt gaa cat atg tgg agt gac gta        1872
Phe Glu Gly Thr Tyr Glu Glu Trp Arg Glu His Met Trp Ser Asp Val
610                 615                 620 gca gcc tac ttt aac ctc gac att gaa aac agt gaa gat aat aaa tct        1920
Ala Ala Tyr Phe Asn Leu Asp Ile Glu Asn Ser Glu Asp Asn Lys Ser
625                 630                 635                 640 act ctt tca ctt caa ttt gtc gac agc gcc gcg gat atg ccg ctt gcg        1968
Thr Leu Ser Leu Gln Phe Val Asp Ser Ala Ala Asp Met Pro Leu Ala
                645                 650                 655 aaa atg cac ggt gcg ttt tca acg aac gtc gta gca agc aaa gaa ctt        2016
Lys Met His Gly Ala Phe Ser Thr Asn Val Val Ala Ser Lys Glu Leu
                660                 665                 670 caa cag cca ggc agt gca cga agc acg cga cat ctt gaa att gaa ctt        2064
Gln Gln Pro Gly Ser Ala Arg Ser Thr Arg His Leu Glu Ile Glu Leu
                675                 680                 685 cca aaa gaa gct tct tat caa gaa gga gat cat tta ggt gtt att cct        2112
```

```
                Pro Lys Glu Ala Ser Tyr Gln Glu Gly Asp His Leu Gly Val Ile Pro
                    690             695             700 cgc aac tat gaa gga ata gta aac cgt gta aca gca agg ttc ggc cta      2160
Arg Asn Tyr Glu Gly Ile Val Asn Arg Val Thr Ala Arg Phe Gly Leu
705                 710             715                 720 gat gca tca cag caa atc cgt ctg gaa gca gaa gaa gaa aaa tta gct      2208
Asp Ala Ser Gln Gln Ile Arg Leu Glu Ala Glu Glu Glu Lys Leu Ala
                725             730             735 cat ttg cca ctc gct aaa aca gta tcc gta gaa gag ctt ctg caa tac      2256
His Leu Pro Leu Ala Lys Thr Val Ser Val Glu Glu Leu Leu Gln Tyr
            740             745             750 gtg gag ctt caa gat cct gtt acg cgc acg cag ctt cgc gca atg gct      2304
Val Glu Leu Gln Asp Pro Val Thr Arg Thr Gln Leu Arg Ala Met Ala
        755             760             765 gct aaa acg gtc tgc ccg ccg cat aaa gta gag ctt gaa gcc ttg ctt      2352
Ala Lys Thr Val Cys Pro Pro His Lys Val Glu Leu Glu Ala Leu Leu
    770             775             780 gaa aag caa gcc tac aaa gaa caa gtg ctg gca aaa cgt tta aca atg      2400
Glu Lys Gln Ala Tyr Lys Glu Gln Val Leu Ala Lys Arg Leu Thr Met
785             790             795             800 ctt gaa ctg ctt gaa aaa tac ccg gcg tgt gaa atg aaa ttc agc gaa      2448
Leu Glu Leu Leu Glu Lys Tyr Pro Ala Cys Glu Met Lys Phe Ser Glu
                805             810             815 ttt atc gcc ctt ctg cca agc ata cgc ccg cgc tat tac tcg att tct      2496
Phe Ile Ala Leu Leu Pro Ser Ile Arg Pro Arg Tyr Tyr Ser Ile Ser
            820             825             830 tca tca cct cgt gtc gat gaa aaa caa gca agc atc acg gtc agc gtt      2544
Ser Ser Pro Arg Val Asp Glu Lys Gln Ala Ser Ile Thr Val Ser Val
        835             840             845 gtc tca gga gaa gcg tgg agc gga tat gga gaa tat aaa gga att gcg      2592
Val Ser Gly Glu Ala Trp Ser Gly Tyr Gly Glu Tyr Lys Gly Ile Ala
    850             855             860 tcg aac tat ctt gcc gag ctg caa gaa gga gat acg att acg tgc ttt      2640
Ser Asn Tyr Leu Ala Glu Leu Gln Glu Gly Asp Thr Ile Thr Cys Phe
865             870             875             880 att tcc aca ccg cag tca gaa ttt acg ctg cca aaa gac cct gaa acg      2688
Ile Ser Thr Pro Gln Ser Glu Phe Thr Leu Pro Lys Asp Pro Glu Thr
                885             890             895 ccg ctt atc atg gtc gga ccg gga aca ggc gtc gcg ccg ttt aga ggc      2736
Pro Leu Ile Met Val Gly Pro Gly Thr Gly Val Ala Pro Phe Arg Gly
            900             905             910 ttt gtg cag gcg cgc aaa cag cta aaa gaa caa gga cag tca ctt gga      2784
Phe Val Gln Ala Arg Lys Gln Leu Lys Glu Gln Gly Gln Ser Leu Gly
        915             920             925 gaa gca cat tta tac ttc ggc tgc cgt tca cct cat gaa gac tat ctg      2832
Glu Ala His Leu Tyr Phe Gly Cys Arg Ser Pro His Glu Asp Tyr Leu
    930             935             940 tat caa gaa gag ctt gaa aac gcc caa agc gaa ggc atc att acg ctt      2880
Tyr Gln Glu Glu Leu Glu Asn Ala Gln Ser Glu Gly Ile Ile Thr Leu
945             950             955             960 cat acc gct ttt tct cgc atg cca aat cag ccg aaa aca tac gtt cag      2928
His Thr Ala Phe Ser Arg Met Pro Asn Gln Pro Lys Thr Tyr Val Gln
                965             970             975 cac gta atg gaa caa gac ggc aag aaa ttg att gaa ctt ctt gat caa      2976
His Val Met Glu Gln Asp Gly Lys Lys Leu Ile Glu Leu Leu Asp Gln
            980             985             990 gga gcg cac ttc tat att tgc gga    gac gga agc caa atg    gca cct gcc  3024
Gly Ala His Phe Tyr Ile Cys Gly    Asp Gly Ser Gln Met    Ala Pro Ala
        995                 1000                   1005
```

```
gtt gaa gca acg ctt atg aaa agc tat gct gac gtt cac caa gtg      3069
Val Glu Ala Thr Leu Met Lys Ser Tyr Ala Asp Val His Gln Val
    1010                1015                1020 agt gaa gca gac gct cgc tta tgg ctg cag cag cta gaa gaa aaa      3114
Ser Glu Ala Asp Ala Arg Leu Trp Leu Gln Gln Leu Glu Glu Lys
1025                1030                1035 ggc cga tac gca aaa gac gtg tgg gct ggg                          3144
Gly Arg Tyr Ala Lys Asp Val Trp Ala Gly
1040                1045
```

<210> SEQ ID NO 2
<211> LENGTH: 1048
<212> TYPE: PRT
<213> ORGANISM: Bacillus megaterium

<400> SEQUENCE: 2

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Cys Asp Glu Ser
    50                  55                  60

Arg Phe Asp Lys Asn Leu Ser Gln Ala Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Ala Pro Ser
    290                 295                 300

Tyr Lys Gln Val Lys Gln Leu Lys Tyr Val Gly Met Val Leu Asn Glu
305                 310                 315                 320
```

```
Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
    450                 455                 460

Gln Ser Ala Lys Lys Ala Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
            595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
            645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735
```

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
            850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
            930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
            1010                1015                1020

Ser Glu Ala Asp Ala Arg Leu Trp Leu Gln Gln Leu Glu Glu Lys
            1025                1030                1035

Gly Arg Tyr Ala Lys Asp Val Trp Ala Gly
            1040                1045

<210> SEQ ID NO 3
<211> LENGTH: 21
<212> TYPE: PRT
<213> ORGANISM: Bacillus megaterium

<400> SEQUENCE: 3

Phe Ser Gln Gln Ala Met Lys Gly Tyr His Ala Met Met Val Asp Ile
1               5                   10                  15

Ala Val Gln Leu Val
            20

<210> SEQ ID NO 4
<211> LENGTH: 21
<212> TYPE: PRT
<213> ORGANISM: Bacillus megaterium

```
<400> SEQUENCE: 4

Asp Ile Ala Val Gln Leu Val Gln Lys Trp Glu Arg Leu Asn Ala Asp
1               5                   10                  15

Glu His Ile Glu Val
            20

<210> SEQ ID NO 5
<211> LENGTH: 21
<212> TYPE: PRT
<213> ORGANISM: Bacillus megaterium

<400> SEQUENCE: 5

Leu Asp Glu Ala Met Asn Lys Leu Gln Arg Ala Asn Pro Asp Asp Pro
1               5                   10                  15

Ala Tyr Asp Glu Asn
            20

<210> SEQ ID NO 6
<211> LENGTH: 21
<212> TYPE: PRT
<213> ORGANISM: Bacillus megaterium

<400> SEQUENCE: 6

Phe Gln Glu Asp Ile Lys Val Met Asn Asp Leu Val Asp Lys Ile Ile
1               5                   10                  15

Ala Asp Arg Lys Ala
            20

<210> SEQ ID NO 7
<211> LENGTH: 21
<212> TYPE: PRT
<213> ORGANISM: Bacillus megaterium

<400> SEQUENCE: 7

His Glu Thr Thr Ser Gly Leu Leu Ser Phe Ala Leu Tyr Phe Leu Val
1               5                   10                  15

Lys Asn Pro His Val
            20

<210> SEQ ID NO 8
<211> LENGTH: 21
<212> TYPE: PRT
<213> ORGANISM: Bacillus megaterium

<400> SEQUENCE: 8

Val Leu Val Asp Pro Ala Pro Ser Tyr Lys Gln Val Lys Gln Leu Lys
1               5                   10                  15

Thr Val Gly Met Val
            20

<210> SEQ ID NO 9
<211> LENGTH: 21
<212> TYPE: PRT
<213> ORGANISM: Bacillus megaterium

<400> SEQUENCE: 9

Glu Ala Leu Arg Leu Trp Pro Thr Ala Pro Ala Phe Ser Leu Tyr Ala
1               5                   10                  15

Lys Glu Asp Thr Val
            20
```

<210> SEQ ID NO 10
<211> LENGTH: 20
<212> TYPE: PRT
<213> ORGANISM: Bacillus megaterium

<400> SEQUENCE: 10

Gly Asp Asp Val Glu Glu Phe Arg Pro Glu Arg Phe Glu Asn Pro Ser
1               5                   10                  15

Ala Ile Pro Gln
            20

<210> SEQ ID NO 11
<211> LENGTH: 21
<212> TYPE: PRT
<213> ORGANISM: Bacillus megaterium

<400> SEQUENCE: 11

Lys Pro Phe Gly Asn Gly Gln Arg Ala Cys Ile Gly Gln Gln Phe Ala
1               5                   10                  15

Leu His Glu Ala Thr
            20

<210> SEQ ID NO 12
<211> LENGTH: 21
<212> TYPE: PRT
<213> ORGANISM: Bacillus megaterium

<400> SEQUENCE: 12

Phe Gly Asn Gly Gln Arg Ala Cys Ile Gly Gln Gln Phe Ala Leu His
1               5                   10                  15

Glu Ala Thr Leu Val
            20

<210> SEQ ID NO 13
<211> LENGTH: 21
<212> TYPE: PRT
<213> ORGANISM: Bacillus megaterium

<400> SEQUENCE: 13

Gly Met Met Leu Lys His Phe Asp Phe Glu Asp His Thr Asn Tyr Glu
1               5                   10                  15

Leu Asp Ile Lys Glu
            20

<210> SEQ ID NO 14
<211> LENGTH: 42
<212> TYPE: DNA
<213> ORGANISM: Artificial sequence
<220> FEATURE:
<223> OTHER INFORMATION: Oligonucleotide used to introduce SpeI
      restriction site

<400> SEQUENCE: 14
gctcataata cgccgctact agtgctatac ggttcaaata tg                                42

<210> SEQ ID NO 15
<211> LENGTH: 30
<212> TYPE: DNA
<213> ORGANISM: Artificial sequence
<220> FEATURE:
<223> OTHER INFORMATION: Forward primer used in error-prone PCR

<400> SEQUENCE: 15

-continued

```
tctcgagaat tcataatcat cggagacgcc                                    30
```

<210> SEQ ID NO 16
<211> LENGTH: 30
<212> TYPE: DNA
<213> ORGANISM: Artificial sequence
<220> FEATURE:
<223> OTHER INFORMATION: Reverse primer used in error-prone PCR

<400> SEQUENCE: 16

```
tggatccact agtagcggcg tattatgagc                                    30
```

MUTANT ENZYMES

This application is a national phase filing under 35 USC §371 of PCT International Application No. PCT/GB2008/003407 filed Oct. 8, 2008, which claims priority to Patent Application GB No. 0719620.7, filed Oct. 8, 2007, both of which are incorporated by reference herein in their entirety.

FIELD OF THE INVENTION

The invention relates to mutant enzymes with enhanced properties.

BACKGROUND OF THE INVENTION

Biological enzyme catalysts, such as $P450_{BM-3}$ enzymes, find increasing use in a variety of industrial applications, ranging from synthesis of fine chemicals, intermediates, pharmaceuticals and drug metabolites to degradation of organic chemical contaminants and pollutants. Protein engineering, using directed evolution or site-directed mutagenesis, can be used to isolate variants of known enzymes, which may create new opportunities and applications for their catalytic activities.

$P450_{BM-3}$ from *Bacillus megaterium* (1) belongs to the superfamily of cytochrome P450 enzymes. There are over 7,700 genes encoding P450 enzymes in the various gene sequence databases. Nomenclature of P450 enzymes has been systemized. The superfamily of enzymes are referred to as CYP, followed by a number for a family of enzymes (hence CYP1, CYP51, CYP102, etc.) which are divided into sub-families denoted by alphabets (hence CYP1A, CYP101B, etc.) and each sub-family member is denoted by a number (hence CYP1A1, CYP3A4, CYP101D3, etc.). A gene encoding a CYP enzyme is denoted by italics, e.g. CYP101A1 gene. $P450_{BM-3}$ has been designated CYP102A1, i.e. it is the first member of the CYP102 family. Henceforth the systemic name of CYP102A1 will be used for $P450_{BM-3}$.

CYP102A1 (1) is an attractive enzyme for biotransformation applications because it is catalytically self-sufficient. Unlike other P450 enzymes, in which the P450 monooxygenase and the electron transfer co-factor proteins are separate entities, CYP102A1 has the haem monooxygenase domain fused to the diflavin electron transfer reductase domain, which contains both the FAD and FMN prosthetic groups in a single polypeptide. The natural substrates of CYP102A1 are believed to be linear or branched medium chain fatty acids (1,2). The crystal structure of the CYP102A1 haem domain became available in 1993 (3), revealing the active site structure and the presence of a substrate access channel. The crystal structure with a bound substrate, published four years later, indicated a change in the side chain conformation for F87 upon substrate binding (4).

Protein engineering of CYP102A1 has been reviewed (5-7). Early studies focused on the active site residue F87, with the F87V, F87A, F87Y and F87G mutations showing varied effects on the activity and selectivity of fatty acid oxidation (8-11). Mutations at F87 have been found to be beneficial to the oxidation of a variety of substrates (7). Residues such as F42, R47, and Y51 at the entrance to the substrate access channel were also targeted. Neutralizing or reversing the charge at the 47 position altered the substrate specificity (8,12), as did the hydrophobic substitution Y51A, while the F42A mutation lowered enzymatic activity (10). WO0031273 disclosed the use of the R47L/Y51F couplet of mutations to promote entry, binding and oxidation of hydrophobic organic molecules such as polyaromatic and terpenoid hydrocarbons. The couplet was also combined with the F87A, I263A, A264G and M354A mutations to give enhanced activity and/or product selectivity of substrate oxidation (13,14). The R47L/Y51F combination, and the R47L and Y51F mutations on their own, are now commonly used in CYP102A1 engineering (15-19).

In addition to rational selection of mutation sites, screening techniques have been utilized to identify other mutations and mutation sites which have desirable effects on activity and selectivity. Random or site saturation mutagenesis was applied to CYP102A1 as early as 1997 (20). NO20020380 disclosed the use of indigo formation via indole oxidation as a screening method to discover CYP102A1 mutants with new activity. Saturation mutagenesis was applied to a number of residues likely to affect substrate binding, and the mutant A74G/F87V/L188Q was reported to oxidize a wide range of organic molecules with enhanced activity and altered selectivity compared to the wild type (21-25). AT342351T disclosed the formation of p-nitrophenol, which is spectroscopically detected, via oxidation of a ω-p-nitrophenoxycarboxylic acid, as a screening procedure in a set of random mutagenesis experiments. The mutations V26T, R47F, S72G, A74G, F87A&V, L188A,G,N,K,Q,R,S&W, M354T were disclosed (26,27).

The p-nitrophenol screening method was extended by using p-nitrophenoxyoctane as the surrogate substrate. WO2002083868, EP1470219 and US2005202419 (subsequently corrected in WO2005017116, EP1660646, and US2005037411) disclosed the mutations L52I, I58V, F87A, H100R, S106R, F107L, A135S, M145A&V, A184V, N239H, S274T, L324I, V340M, I366V, K434E, E442K, V446I.

WO2003008563 and US2003100744 disclosed the results of further rounds of random mutagenesis, gene shuffling and screening using the same method, and reported the mutations M30I, E64A, V78A, F87A,D,G,H,I,K,N,R,V&W, H138Y, F162S, H171Q, T175I, V178I, A184V, N186D, D217V, I220T, K224I, S226I, D232G, T235A, H236Q, E252G, R255S, I258T, I259V, T268Q, A290V, A295T, L353V, D370Q, E380G, G396M, T411A, M416L.

WO2005017105, US2005059128, and EP1639091 disclosed the use of the same methods and reported the mutations R47C, L75I&W, V78A,F&T, A82L,F,G,I,S&T, F87I, L&V, T88C, K94I, P142S, T175I, A184V, F205C, S226R, H236Q, E252G, R255S, T260,L,N&S, A290V, A328V&M, L353V.

WO2006105082 then disclosed the mutations R47C, V78F, A82S, K94I, P141S, T175I, A184V, F205C, S226R, H236Q, E252G, R255S, A290V, A291V, A328F, L353V.

These series of mutants generated by random mutagenesis show enhanced activity for the oxidation of alkanes from ethane to medium chain alkanes (28-30). There were also selectivity changes, in particular when the directed evolution variants were combined with mutations introduced into the active site by site-directed mutagenesis, e.g. in octane oxidation where the mutations shift the site of oxidation towards the terminal carbon (31), selective epoxidation of terminal alkenes (32), and enantioselectivity in the oxidation of cyclopentanecarboxylic acid derivatives (33). It is notable that better results can often be obtained by combining directed evolution with rational re-design.

CYP102A3 is a P450 enzyme in the same sub-family as CYP102A1. Random mutagenesis of CYP102A3, followed by alkane oxidation and monitoring NADH formation in the presence of an alcohol dehydrogenase specific for terminal alcohols, gave rise to a mutant that formed 50% 1-octanol from octane oxidation. This is the highest proportion of terminal C—H bond oxidation of a linear alkane observed to date by an engineered CYP102 family P450 enzyme (34).

There is a continuing need to isolate further mutants of industrially useful enzymes, such as CYP102A1 enzymes, in order to further understand the impact of structural changes on their catalytic mechanism, improve their catalytic turnover, and expand their range of substrates and/or products. In general, engineering of P450 enzymes such as CYP102A1 is carried out to enhance enzymatic activity, with control of product selectivity and substrate specificity being important secondary objectives. Mutations and mutation sites which can couple selectivity control to enhanced monooxygenase activity are conspicuously lacking, such that enzymatic turnover of compounds may be fast but not sufficiently selective, or there is some selectivity but the reactions are slow, or the desired product is not formed. There is also a need for screening methods that can provide mutants with enhanced activity and/or desirable selectivity.

SUMMARY OF THE INVENTION

It has now been found that, according to the present invention, substitution mutations at specific positions of CYP102A1 have desirable effects in enhancing monooxygenase activity and also provide for altered selectivity. These mutation sites were identified through use of an innovative screening method that provides for selection both of enhanced activity and enhanced/altered selectivity.

The present invention provides a mutant CYP102A1 enzyme, which has enhanced monooxygenase activity and/or altered selectivity and comprises a substitution at one or more of positions 117, 131, 191, 215, 276, 307, 330, 377, 401, 403, 425 of CYP102A1. There is additionally provided a process for oxidizing a substrate which is an organic compound, which process comprises oxidizing said organic compound with a mutant CYP102A1 enzyme of the invention.

The claimed substitutions form part of the same inventive concept, as they share effects in enhancing monoxygenase activity and/or alter selectivity of CYP102A1. Substitutions at positions 330, 401 and 403 also exert their effects via common structural and/or functional mechanisms, as outlined below.

SEQUENCE IN THE SEQUENCE LISTING

SEQ ID NO:1 is the sequence of CYP102A1.

DETAILED DESCRIPTION OF THE INVENTION

Figure 1:
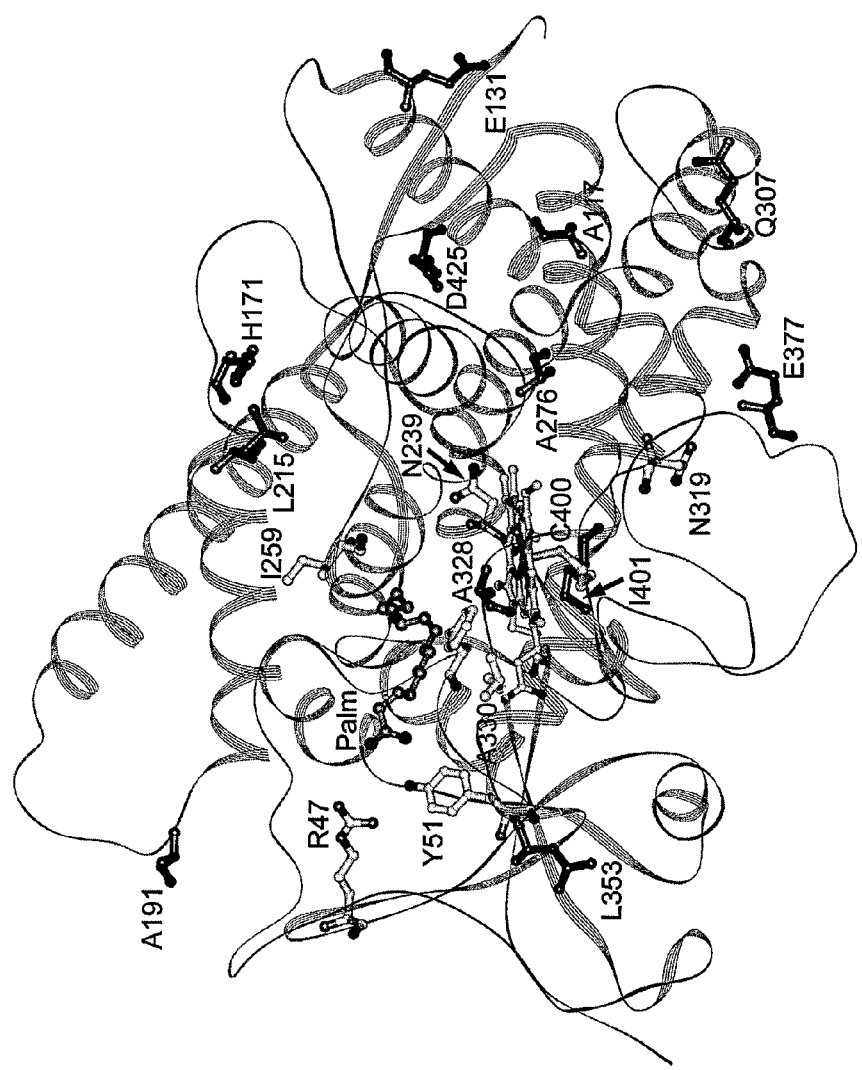
FIG. 1: Location of relevant residues in CYP102A1 (P450$_{BM-3}$). Palm denotes a fatty acid substrate of the enzyme.

The invention is applicable to natural and artificial homologues of CYP102A1, for example, which comprise sequence that has at least 40% amino acid sequence identity to CYP102A1. Such homologues typically comprise amino acid sequence which corresponds to (i.e. is homologous to or the same as) the haem monooxygenase domain of CYP102A1 (represented by amino acid positions 1 to 480).

The enzyme of the invention comprises (or consists of) sequence which has at least 40% identity to SEQ ID NO:1 (the sequence of CYP102A1). In preferred embodiments, the sequence may be at least 55%, 65%, 80% or 90% and more preferably at least 95%, 97% or 99% homologous thereto over at least 20, preferably at least 30, for instance at least 40, 60, 100, 200, 300, 400 or more contiguous amino acids, or even over the entire sequence of the homologue. In one embodiment the enzyme of the invention has any of the specified percentage homologies when compared to amino acid residues 1 to 480 of CYP102A1. The contiguous amino acids may include the active site. This homology may alternatively be measured not over contiguous amino acids but over only the amino acids in the active site. Thus the homologue is typically at least 40% homologous to CYP102A1 on the basis of amino acid identity. The enzyme of the invention may have a percentage identity with CYP102A1 sequence which is the same as any of the specific percentage homology values (i.e. it may have at least 40%, 55%, 80% or 90% and more preferably at least 95%, 97% or 99% identity) across any of the lengths of sequence mentioned above.

The homologous sequence may represent a mutated portion of the CYP102A1 sequence and/or may be present in the form of the full-length fused polypeptide of the enzyme of the invention.

Any of the homologous proteins (i.e. described as being homologous to another protein) mentioned herein are typically at least 40% homologous to the relevant protein. Homology can be measured using known methods. For example the UWGCG Package provides the BESTFIT program which can be used to calculate homology (for example used on its default settings) (Devereux et al (1984) Nucleic Acids Research 12, 387-395). The PILEUP and BLAST algorithms can be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Typically the homologous protein differs from the relevant protein by at least, or less than, 2, 5, 10, 20, 40, 50 or 60 mutations (each of which can be substitutions, insertions or deletions) when compared to all of the protein or over any of the lengths of contiguous amino acids mentioned above.

The enzymatic activity of the CYP102A1 enzyme of the invention is typically measured in vitro using any of the substrates or conditions mentioned herein and is given as the NADPH oxidation rate, the product formation rate and coupling efficiency. The rates are turnover frequencies and given in (nmol NADPH) (nmol CYP102A1)$^{-1}$ (min)$^{-1}$ or (nmol product) (nmol CYP102A1)$^{-1}$ (min)$^{-1}$. Coupling efficiency is the percentage of NADPH consumed which was utilised for product formation, i.e. a percentage of the theoretical maximum efficiency. The CYP102A1 enzyme of the invention (for example when used in the process of the invention) may typically have a coupling efficiency of at least 1%, such as at least 2%, 4%, 6%, 10%, 20%, 40%, 80% or more. The CYP102A1 enzyme (for example when used in the process of the invention) typically has a product formation rate of at least 2 min$^{-1}$, such as at least 4, 10, 15, 20, 25, 50, 100, 200, 300, 500, 700, 1000, 2000 min$^{-1}$ or more. Where more than one product is formed (which is commonly the case), the product formation rates represent the total amount of all oxidation products formed. In some embodiments, product formation rate of a specific oxidation product is measured, i.e. not all oxidation products may be measured.

The mutant CYP102A1 enzymes of the invention display an enhanced monooxygenase activity and/or an altered selectivity with respect to the corresponding wild type CYP102A1 enzyme. Enhanced monooxygenase activity may be characterised in terms of an increased coupling efficiency or an increased product formation rate with one or more substrates for oxidation. The increased coupling efficiency or increased product formation rate may or may not be shared across all substrates utilised by the mutant CYP102A1 enzyme. The mutant CYP102A1 enzymes typically display a coupling efficiency which is at least 10%, 20%, 50%, 100%, 500%, 1000% or 1500% greater than that of the wild type enzyme. The mutant CYP102A1 enzymes may also have a product formation rate which is at least 50%, 100%, 150%, 500%, 1000%, 2000%, 5000%, 10000% greater than that of the wild type enzyme.

It is to be understood that the mutant CYP102A1 enzymes of the invention may also display other altered characteristics with respect to the corresponding wild type enzyme and mutants disclosed in the literature, such that the effects may include, but may also not be limited to, enhanced monooxygenase activity. For example, the mutant enzyme may display an altered substrate specificity, allowing preferential utilization of specific substrates, or may display monooxygenase activity where the wild type enzyme or known mutants are not able to oxidize the substrate organic compound.

The mutant enzymes of the invention may also display altered product selectivity where a product formed in minor proportions by the wild type becomes the dominant product for the mutant, or new products formed in minor proportions or not at all by the wild type become the majority or dominant product. Further altered characteristics of the mutant enzymes and of the oxidation processes carried out by the mutant enzymes are described below.

The mutant CYP102A1 enzymes comprise a substitution at one or more of positions 117, 131, 191, 215, 276, 307, 330, 377, 401, 403, and 425 of CYP102A1. Typically, they may comprise substitutions at 2 or more, 3 or more, 4 or more, 5 or more, 6 or more of the positions defined above. In one preferred embodiment, where there is a substitution at position 330, there are less than 5 other substitutions, such as less than 3, or in one embodiment none of the other positions are substituted.

Where specific mutants of CYP102A1 are described, the letter of the amino acid residue present in the natural form of CYP102A1 is followed by the position, followed by the amino acid in the mutant. These positions can be correlated to the numbering shown in SEQ ID NO:1. To denote multiple mutations in the same protein each mutation is listed separated by slashes. Also, particularly preferred mutants may be described using internal denominations as outlined below.

While mutations are defined by reference to a position in CYP102A1, the invention also encompasses equivalent substitution mutations at a homologous or corresponding position in the polypeptide chain of a homologue of CYP102A1 which shares at least 40% amino acid identity to SEQ ID NO:1. An equivalent position is determined by reference to the amino acid sequence of SEQ ID NO:1 (the amino acid sequence of SEQ ID NO:1 is found in SEQ ID NO:2). The homologous or corresponding position can be readily deduced by lining up the sequence of the homologue and the sequence of CYP102A1 (SEQ ID NO:1) based on the homology between the sequences. The PILEUP and BLAST algorithms can be used to line up the sequences. Where the homologous or corresponding amino acid referred to is an active site residue, it will generally be in a similar place in the active site of the homologue as any of the specific amino acids discussed herein.

Despite having a highly conserved tertiary structure, the P450 superfamily of enzymes is well known to those skilled in the art to be unusual among proteins and enzymes in having primary structures with low homology (35-37). There are now >6500 CYP genes in the genome databases, and >150 structures in the Protein Data Bank. All P450 structures determined to date show a characteristic topography incorporating a helix-rich domain packed against a mainly β strand domain, as described by Poulos and co-workers in the first reported crystal structure of a P450 enzyme (CYP101A1) (38). The helices are termed A-L, and the β strands β1-β5, with the overall topography now being known as the 'P450 fold" (38-42). Of the secondary structural elements, the B and B' helices, the BC loop, the F and G helices and the FG loop on the distal side of the haem form the substrate binding pocket. Sequence alignments readily identify residues within these helices and loops, but there is a high degree of variability within this general framework, both in terms of amino acid sequence and structural arrangement, and it is this that gives rise to the myriad specificity, activity and selectivity patterns of P450 catalysis.

P450 enzymes in different families have homologies (amino acid identities) as low as 20% (35-37). A sample of alignment between CYP102A1 and structurally characterized P450 enzymes is shown in Table A. Until recently, continued sequence analysis had suggested that as few as three residues out of typically 400-460 in P450 enzymes or domains were absolutely conserved: the proximal cysteine ligand to the haem iron, and the EXXR motif in the K helix that might play a role in haem association and binding (43). However, results on the CYP157 family published in 2006 showed that even the EXXR motif is not conserved, leaving the proximal cysteine as the only conserved residue across the whole P450 superfamily. In the systematic classification of the P450 superfamily (44), enzymes with just 40% amino acid identity are therefore placed within the same family, and closely related members of a family (>55% identity) are grouped into sub-families (see, for example, Table B).

It is in fact the detailed molecular structure, substrate specificity and product selectivity that are conserved within a family rather than sequence identity, which is often low. The most striking example is the CYP51 family of sterol 14α-demethylases that are found in all kingdoms of life. These play the pivotal role of oxidative demethylation of the C14 methyl group of intermediates formed after cyclization of squalene oxide. Sequence alignments showed that homology between known CYP51 family genes from across all kingdoms of life was on average 30%, rising as high as 95% in closely related species such as mammals and falling as low as 23% between lower organisms (45). It is increasingly recognized that the 40% cut-off for assigning enzymes to the same family could be too high in some instances, and that enzymatic activity and the higher homology often observed for active site residues may need to be taken more into consideration in future.

Thus, homologues that are typically at least 40% homologous to CYP102A1 on the basis of amino acid identity may also be readily identifiable on the basis of the "P450 fold", and alignment of sequences of homologues to introduce an equivalent mutation at a corresponding or homologous position may be assisted by knowledge of the conserved nature of the arrangement of α helices and β strands that comprises the P450 fold shared throughout the enzyme family.

It is to be understood that CYP102A1 is a fusion of the electron transfer reductase domain and the haem monooxygenase domain. These domains may be cleaved proteolytically or by truncation of the full-length gene. The active site (substrate binding pocket) is located in the haem domain. Some members of the CYP102 family are not fusion proteins but the sequence homology with the CYP102A1 haem domain is 40%. Thus, sequence homology may be measured solely over the haem domain in these circumstances. Equivalent residues in these enzymes to those in CYP102A1 disclosed in the present invention can be identified by sequence homology and structural analysis known to those skilled in the art.

An amino acid in the active site is one which lines or defines the site in which the substrate is bound during catalysis or one which lines or defines a site through which the substrate must pass before reaching the catalytic site. Therefore such an amino acid typically interacts with the substrate during entry to the catalytic site or during catalysis. Such an interaction typically occurs through an electrostatic interaction (between charged or polar groups), hydrophobic interaction, hydrogen bonding or van der Waals forces. Active site amino acids can be identified by sequence alignment and reference to the known crystal structure of the haem domain of wild type CYP102A1, or the crystal structure of the homologues.

Where the mutated residue is not an active site residue, computerized or manual alignment of sequences of the homologue and of CYP102A1 is carried out to deduce the homologous or corresponding position, which may be assisted by knowledge of the residues flanking the mutated position in CYP102A1. Thus, for example, the 10 N-terminally and C-terminally flanking residues to the following positions in CYP102A1 are:

FSQQAMKGYH(A117)MMVDIAVQLV;
(SEQ ID NO: 3)

DIAVQLVQKW(E131)RLNADEHIEV;
(SEQ ID NO: 4)

LDEAMNKLQR(A191)NPDDPAYDEN;
(SEQ ID NO: 5)

FQEDIKVMND(L215)VDKIIADRKA;
(SEQ ID NO: 6)

HETTSGLLSF(A276)LYFLVKNPHV;
(SEQ ID NO: 7)

VLVDPAPSYK(Q307)VKQLKTVGMV;
(SEQ ID NO: 8)

EALRLWPTAP(A330)FSLYAKEDTV;
(SEQ ID NO: 9)

GDDVEEFRP(E377)RFENPSAIPQ;
(SEQ ID NO: 10)

KPFGNGQRAC(I401)GQQFALHEAT;
(SEQ ID NO: 11)

FGNGQRACIG(Q403)QFALHEATLV;
(SEQ ID NO: 12)

GMMLKHFDFE(D425)HTNYELDIKE
(SEQ ID NO: 13)

Conservation of 2, 3 or more of the N- and/or C-terminal flanking residues can allow for deduction of the homologous or corresponding position at which a mutation is to be introduced.

Similar analyses can be carried out for any other positions in CYP102A1 that are referred to in the description so as to identify the homologous or corresponding site in a naturally occurring homologue of CYP102A1.

Functional fragments of CYP102A1 enzymes are also encompassed in the present invention. These fragments may thus comprise only those amino acids which are required for oxidation activity. Thus, with reference to the polypeptide sequence of CYP102A1, the reductase domain and/or up to 20 residues at the N-terminal or C-terminal portion of the monooxygenase domain could be deleted without significantly affecting folding of the active site or the intrinsic substrate oxidation ability of the monooxygenase domain. In homologues of CYP102A1, similar truncations are possible, and the extent of truncation possible can be determined by methods for monitoring oxidation activity that are described herein. Truncated forms of the enzyme may possess advantageous properties in terms of stability, expression level, and activity of the protein.

The nature of the amino acid to be substituted at the positions of CYP102A1 described herein (or equivalent positions as defined above) is primarily determined by the requirement for the mutant to display an enhanced monooxygenase activity. Thus, an amino acid that is introduced will typically enhance monooxygenase activity. Where any reference is made to specific substitution mutations in CYP102A1, it is to be understood that any substitution of another amino acid residue at the same position which has effects which are redundant over, or similar to, the effect of the specific substitution mutation on the oxidation activity of the CYP102A1 enzyme, is encompassed according to the present invention. Similarly, where a specific substitution mutation also has an effect on another parameter of the CYP102A1 enzyme, such as substrate specificity, or the range or ratio of oxidation products obtained in oxidation of a given substrate, it is to be understood that substitutions of other amino acid residues that also elicit a redundant or similar effect are also contemplated for use according to the invention.

In some embodiments, the substitution introduces a conservative change, which replaces the amino acid with another amino acid of similar chemical structure, similar chemical properties or similar side-chain volume. The amino acids introduced may have similar polarity, hydrophilicity or hydrophobicity to the amino acids they replace. Conservative amino acid changes are well known in the art and may be selected in accordance with the changes defined in Table C. Where amino acids have similar polarity, this can also be determined by reference to the hydropathy scale for amino acid side chains (Table D).

Conservative amino acid changes may also be determined by reference to the Point Accepted Mutation (PAM) or BLOcks SUbstitution Matrix (BLOSUM) family of scoring matrices for conservation of amino acid sequence. Thus, conservative amino acid changes may be members of an equivalence group, being a set of amino acids having mutually positive scores in the similarity representation of the scoring matrix selected for use in an alignment of the reference and mutant polypeptide chains.

It is to be understood that the definitions of physical characteristics provided in Table C are not considered to be limiting on the invention and that non-polar amino acids include amino acids with aliphatic side chains and amino acids with aromatic side chains. The amino acid proline is classified as non-polar but it also has the property of being rigid and can cause changes in secondary structure. For example prolines are often found at the end of helices. Also, depending on the specific context of the side chain of a given amino acid residue, for example the amino acid tyrosine, generally classed as non-polar due to its aromatic ring, may have analogous functional effects to a polar amino acid residue such as threonine via its hydroxyl group. Thus, tyrosine may be considered to be both a non-polar and a polar amino acid for the purposes of the invention. Furthermore, amino acids which are described as polar or hydrophilic may be uncharged or charged, and may also be basic or acidic. The amino acid histidine is well known to have a pKa value near 7, so that at neutral pH depending upon the protein environment, it may or not be protonated on its side chain, and thus may or not carry a charge. Thus, histidine may be considered to be both a polar charged or a polar uncharged amino acid residue for the purposes of the invention.

Specific examples of conservative amino acid changes for positions 117, 131, 215, 307, 330, 401, and 403 in CYP102A1 (or equivalent positions thereto) include, but are not limited to:

A117V, A117I, A117L, A117P, A117M, A117F, A117W, A117Y;
E131D;
L215I, L215V, L215P, L215F, L215W, L215Y;
Q307H, Q307N, Q307S, Q307T, Q307Y;
A330P, A330I, A330L, A330M, A330V, A330F, A330W, A330Y;
I401P, I401I, I401L, I401M, I401V, I401F, I401W, I401Y;
Q403N, Q403H, Q403A, Q403T, Q403Y.

In other preferred embodiments, the amino acid substitution introduces a polar amino acid at a given position of the wild type enzyme, typically where the existing residue is a non-polar residue, thus changing polarity. Specific examples of polar amino acid substitutions for positions 191 and 276 in CYP102A1 (or equivalent positions thereto) include, but are not limited to:

A191T, A191S, A191C, A191Y, A191H, A191K; A191R, A191N, A191Q;
A276T, A276S, A276C, A276Y, A276H, A276K, A276R, A276N, A276Q.

Contrastingly, in other preferred embodiments, the amino acid substitution introduces a non-polar amino acid at a given position of the wild type enzyme, typically where the existing residue is a polar residue. For example, a non-polar amino acid may be introduced at position 377 or 403, or an equivalent position thereto. Specific examples include but are not limited to:

E377A, E377V, E377L, E377I, E377P, E377F, E377Y, E377W;
Q403P, Q403W, Q403F, Q403Y;

In a further embodiment, the amino acid substitution causes a charged side chain group to be lost at a given position of the wild type enzyme. Thus, the substitution introduces an uncharged amino acid at the relevant position. This may or may not lead to a loss of polarity at this position, such that either a polar uncharged or a non-polar (aromatic or aliphatic) residue is introduced. For example, a non-polar or a polar uncharged residue may be introduced at position 425, or at an equivalent position thereto. Specific examples include, but are not limited to:

D425N, D425Q, D425H, D425S, D425T, D425A, D425L, D425V, D425I, D425P, D425W, D425Y, D425F.

In still further embodiments, an amino acid of an increased side-chain volume is introduced at a position of the invention. In preferred embodiments, an amino acid of increased side-chain volume, typically a bulky non-polar amino acid is introduced at position 330, 401, 403 or at an equivalent position thereto. Particularly preferred substitutions for position 330 are A330P, A330V, A330L, A330I, A330W, A330F, A330Y. Particularly preferred substitutions for position 403 are Q403P, Q403W, Q403F. In other embodiments, for example at position 377, it may be preferred that the amino acid to be introduced has a reduced side-chain volume, such as E377A or E377G.

The mutations discussed herein are generally introduced into the enzyme by using methods known in the art, such as site directed mutagenesis of the enzyme, PCR and gene shuffling methods or by the use of multiple mutagenic oligonucleotides in cycles of site-directed mutagenesis. Thus the mutations may be introduced in a directed or random manner. The mutagenesis method thus produces one or more polynucleotides encoding one or more different mutants. Typically a library of mutant genes is produced which can be used to produce a library of mutant enzymes.

The enzyme may have 1, 2, 3, 4, 5 to 10, 10 to 20, 20 to 40 or more other mutations in addition to the one or more mutations specified above, such as substitutions, insertions or deletions. These additional mutations may or may not enhance monooxygenase activity of the mutant CYP102A1 enzyme. The other mutations may be in the active site or outside the active site. For example, the mutations may be in the second sphere, i.e. residues which affect or contact the position or orientation of one or more of the amino acids in the active site. An insertion will typically be N and/or C terminal. Thus the enzyme may contain a short peptide of up to 20 amino acids or a full-length protein fused to either or both of the termini, e.g. to aid protein purification by affinity chromatography or immobilisation on a solid matrix. A deletion typically comprises the deletion of amino acids which are not involved in catalysis, such as those outside the active site (thus the enzyme is a mutated fragment of a naturally occurring enzyme).

Other mutations in the active site typically alter the position and/or conformation of the substrate when it is bound in the active site. The mutations may make the site on the substrate which is to be oxidized more accessible to the haem group. Thus the mutations may be substitutions to an amino acid which has a smaller or larger, or more or less polar, side chain.

Additional mutations can include amino acid residue changes that can increase the stability of the enzyme. These mutations typically prevent oligomerisation of the protein, e.g. dimerisation of P450$_{cam}$ (CYP101A1) has been removed by substitution of Cys344, preferably to alanine. The crystal structure of full-length CYP102A1 is not yet available, only those of the separate haem and FAD/FMN domains. A similar substitution is not necessary for CYP102A1 because Cys334 of CYP101A1 aligns with Asp370 in CYP102A1. However, the crystal structure of the full-length CYP102A1 and/or the reductase domain may reveal cysteine residues that may be removed by substitution with alanine to improve protein stability. Other mutations can also inhibit oligomerisation arising from contacts between hydrophobic patches on protein surfaces. Still further mutations include insertions/deletions that aid enzyme purification and/or immobilisation, and mutations that allow the protein to be prepared in soluble form, for example by the introduction of deletions or a polyhistidine tag, or by mutation of the N-terminal membrane anchoring sequence.

Preferably, the additional mutations are selected from one or more of the following mutations in CYP102A1: R47L, Y51F, A74G, A264G, N239H, I259V, L353I, F87A, F87L, F87G, H171L, L188Q, N319Y, I263A, A328P, or from the same mutations at equivalent positions thereto. It is also to be understood that the same considerations apply as outlined above in reference to positions 117, 131, 191, 215, 276, 307, 330, 377, 401, 403 and 425, in relation to selecting other amino acid changes that have redundant or similar effects to those specifically listed. Thus, for example, depending on whether the specific additional mutation listed above is a conservative change, changes polarity or introduces an uncharged amino acid, an analogous range of amino acids would be suitable for introduction at each additional position.

In particularly preferred embodiments, the mutant CYP102A1 enzymes of the invention comprise one or more groups of mutations selected from the following groups of mutations in CYP102A1:
  i) A330P
  ii) A191T/N239H/I259V/A276T/L353I;
  iii) F87A/H171L/Q307H/N319Y;
  iv) F87A/A330P/E377A/D425N;
  v) F87A/A117V/E131D/L215I;
  vi) I401P;
  vii) R47L/Y51F/I401P;
  viii) F87A/I401P;
  ix) R47L/Y51F/F87A/I401P;
  x) R47L/Y51F/A330P/I401P;
  xi) Q403P;
  xii) R47L/Y51F/Q403P;
  xiii) R47L/Y51F/F87A/Q403P.
or comprise equivalent groups of mutations thereto.

The A330P mutation as defined in i) is an unusual mutant in several respects, as unlike other directed evolution variants whose effects may depend on a medley of altered residues acting in concert, its activity derives from a single point mutation. In CYP102A1, A330 lies next to a naturally occurring proline residue at position 329, and thus A330P juxtaposes two prolines at a primary substrate contact point in an area of β-sheet (3). The crystal structure of the mutant (FIG. 2) suggests that this constricts the access channel and makes the active site less accessible, thereby leading to a more closed active site and altering the binding configuration for substrates. As will be seen below, this has characteristic effects on monooxygenase activity and product selectivity.

Groups of mutations and iii) enhance the activity of CYP102A1, while broadly mirroring the specificity traits displayed by the wild type enzyme. With the exception of residue 87 in groups iii) to v), none of the positions mutated in any of the groups of mutations are active site residues.

For example in group ii), position 353 lies next to a substrate access channel residue 354, while residues 191, 239, 259, 276 and 353 are located at the protein surface. A191 is noticeably displaced on palmitate binding according to the crystal structure (4), and lies on the outer lip of the access channel. It is speculated that mutating this residue may have effects on substrate enticement and/or capture.

In group iii), position 171 is located on or close to the protein surface, while residues 307 and 319 are close to the region thought to be the docking site for the electron transfer reductase domain, and thus may potentially mediate its effects on enhancement of monooxygenase activity through influences on electron transfer kinetics.

Group of mutations iv) includes the A330P mutation at a substrate contact point, and mutations at positions 377 and 425 which are located peripherally in the enzyme structure close to the protein surface, as are positions 117, 131, and 215 in group of mutations v).

In still preferred embodiments, the mutant CYP102A1 enzymes of the invention of the classes defined above:
  i) additionally comprise one or more of the following mutations in CYP102A1: R47L, Y51F, A74G, A264G, or equivalent mutations thereto;
  ii) additionally comprise one or more of the following mutations in CYP102A1: R47L, Y51F, F87A, F87L; and
  iii) additionally comprise one or more of the following mutations in CYP102A1: F87A, F87G, I259V, I263A.

It is to be understood that up to 1, 2, 3, 4, 5 to 10, 10 to 20 or more other mutations in addition to the specific mutations or specific additional mutations specified above may also be included in these preferred embodiments of the mutant CYP102A1 enzymes of the invention.

The substrate for the oxidation process is any organic compound, more typically any organic compound capable of being oxidized by a monooxygenase enzyme. The suitability of any organic compound for oxidation by a monooxygenase enzyme may be routinely determined by the methods described herein.

The oxidation process causes the formation of a C—O bond in the compound, generally as the alcohol from the oxidation of a carbon-hydrogen bond, but an epoxide may be formed from the oxidation of a C=C bond. The oxidation may thus introduce an alcohol, aldehyde, ketone or epoxide group. Alternatively the oxidation may cause the further oxidation of an oxygen containing group, such as converting an alcohol group into an aldehyde or ketone. 1, 2 or more carbon atoms may be attacked in the same substrate molecule. Oxidation can also result in N- and O-dealkylation of the substrate molecule.

The oxidation typically gives rise to 1, 2 or more oxidation products. These different products may result from different carbon atoms being attacked and/or from different degrees of oxidation occurring at a given carbon atom.

The oxidation may occur on either a ring carbon atom or a substituent carbon atom or both. At least the initial oxidation will involve attack of a C—H bond which may be activated or non-activated or attack at a carbon-carbon double bond (typically giving an epoxide). Generally an activated C—H bond is where the carbon atom is in a benzylic or allylic position. Aromatic rings and olefinic double bonds activate C—H bonds to attack by stabilising the radical intermediate or any build-up of charge generated during the reaction pathway. The carbon of the C—H bond may be primary, secondary or tertiary. The oxidation may occur to result in dehydrogenation leading to a C=C double bond formation rather than insertion of an oxygen atom. This is most likely to occur when the alkyl substituent is branched, or dehydrogenation leads to a C=C bond that is conjugated to an aromatic system, or dehydrogenation leads to the formation of an aromatic system.

The substrate can either be a natural substrate of a wild type CYP102A1 enzyme or a substrate which is not normally a substrate for the wild type enzyme, but which is capable of being utilized as such in the mutant enzyme. Examples of natural substrates for the CYP102A1 enzymes are branched and straight chain fatty acids, which are hydroxylated by wild type CYP102A1 at sub-terminal positions ($\omega$-1 to $\omega$-3). Preferred examples are lauric acid, undecanoic acid, decanoic acid, nonanoic acid and octanoic acid.

In preferred embodiments, the substrate is a short-chain alkane or a medium-chain alkane or an alkylbenzene. The term alkane refers to acyclic branched or unbranched hydrocarbons having the general formula $C_nH_{2n+2}$.

A short-chain alkane has typically from 1 to about 9 carbon atoms, more preferably 1 to 8, 1 to 6, or 1 to 4 carbon atoms. A $C_1$-$C_8$ alkyl group or moiety can be linear or branched. Where it is a $C_1$-$C_4$ alkyl moiety, it can be, for example, methyl, ethyl, n-propyl, i-propyl, sec-butyl and t-butyl.

An alkylbenzene has one or more alkyl groups or moieties substituted at positions on the benzyl aromatic ring. The numbers of carbon atoms in the alkyl groups or moieties can be typically from 1 to about 8 carbon atoms, more preferably 1 to 8, 1 to 6, or 1 to 4 carbon atoms.

In some embodiments there may be 1, 2, 3 or more substituents present on the backbone of the short-chain or medium-chain alkane or directly substituted on the benzyl ring, or on the alkyl substituent of the alkylbenzene. Any combination of the following substituents may be present. The substituent is typically a halogen atom or an alkyl or alkenyl group, which generally has 1 to 6 carbons, the substituent optionally being substituted with one or more halogens. The substituent may also comprise 1, 2 or more oxygen, halogen or nitrogen atoms and for example may be an alcohol, aldehyde, ketone, ether, amine or epoxide group.

Examples of preferred short-chain alkane substrates include, but are not limited to pentane, 3-methylpentane, 2-methylbutane, butane, propane, ethane and methane, octane and nonane. Examples of preferred alkylbenzene substrates include, but are not limited to propylbenzene, ethylbenzene, butylbenzene, cumene, t-butylbenzene, o-xylene, m-xylene, p-cymene and ethylanisole. Other preferred aromatic compounds are naphthalene and fluorene.

It is to be noted that organic compounds such as butane, naphthalene, and in particular, propane, t-butylbenzene and o-xylene are broadly classified as "non-natural" substrates for the wild type CYP102A1 enzyme, but are capable of being oxidized by the mutant CYP102A1 enzymes of the invention. A non-natural substrate can be defined as a molecule which has no detectable coupling rate and/or product formation when incubated with the wild type CYP102A1. Non-natural substrates may also include molecules which are oxidized at <10% of the rate for a natural substrate by the wild type CYP102A1 enzyme such that they may not be regarded as a bona fide substrate.

In other embodiments of the invention, the substrate is a terpene, for example a monoterpene, or a sesquiterpene. The substrate can also be a cycloalkene. Although the terpenes used in the present invention will generally have the formula $(C_5H_8)_n$, where n is 2 or more, especially 2 or 3, it is to be understood that the term "a terpene" extends to compounds which are strictly referred to as "a terpenoid", involving the loss or shift of a fragment, generally a methyl group. Thus, for example, sesquiterpenes (where n is 3) which can be used in the present invention may contain only, say, 14, rather than 15, carbon atoms. Generally the terpene is one which can be built up from isoprene units. The terpene may be cyclic or acyclic. It is moreover understood that a "terpenoid" also extends to compounds that are related to terpenes and may contain one or more oxygen atom, for example in the form of an alcohol or a ketone group, such as damascones and ionones, in particular $\beta$-ionone.

The monoterpenes (where n is 2) will generally have 10 carbon atoms, typically with 1 to 3 double bonds, especially 1 or 2 ring double bonds, and typically with 0 to 2 rings. It is possible for one of the rings to be formed as a bridge containing, typically 0 or 1 carbon atoms. In other words, it can be formed by a direct link between 2 carbon atoms of an existing ring or with an intermediate methylene group. If the terpene is acyclic it will generally contain at least 2 double bonds and generally 3.

The sesquiterpenes will normally contain 14 or 15 carbon atoms, typically with 0 to 2 double bonds and typically 1 to 3 rings, with the possibility of fused rings and/or bridged rings.

The rings which may be present in the terpenes will typically have from 3 to 9 carbon atoms, more especially 5 or 6 carbon atoms. Thus, in particular, the terpenes will contain a cyclohexane, or cyclohexadiene ring.

The terpenes will generally contain a total of 3 or 4 exocyclic methyl or methylene groups, for example 2 methyl groups and 1 methylene group or 3 methyl groups for a monoterpene, and 3 methyl groups and 1 methylene group or 4 methyl groups for a sesquiterpene.

The monoterpene is typically a limonene such as R-limonene, a pinene such as (+)-$\alpha$-pinene, terpinene, sabinene, thujene, myrcene, ocimeme, nerol or geraniol.

The sesquiterpene is generally formed by a head-to-tail arrangement of three isoprene units. The sesquiterpene is typically an aromadendrene, caryophyllene, longifolene, valencene, isobazzanene, silphinene, ishwarane, isopatchchoul-3-ene, or isosesquicarene. It is particularly preferred that the sesquiterpene substrate be valencene.

The cycloalkene generally comprises up to 9 ring members, e.g. it is a 5, 6, 7, 8, 9 or more membered ring. The cycloalkene is typically a cyclohexene.

Substituted derivatives of any of the terpenes or cycloalkenes mentioned above may also be used. Typically 1, 2, 3 or more substituents are present. Any combination of the following substituents may be present. The substituent is typically a halogen atom or an oxygen or nitrogen containing group or an alkyl or alkenyl group, which generally has 1 to 6 carbons, the substituent optionally being substituted with one or more halogens.

The substituent typically has the formula $C_nH_kX_m$, wherein X is the halogen, oxygen or nitrogen containing group, n is 1, 2, 3 or more, m is 1, 2, 3, 4 or more and k is an integer which has an appropriate value so that the valencies of the substituent $C_nH_kX_m$ are satisfied. For an alkyl substituent k+m=2n+1. Typically k is 1, 2, 3, 4 or more, or may be 0, i.e.

the substituent is a perhaloalkyl group. The halogen is typically fluorine, chlorine or bromine. The substituent may also comprise 1, 2 or more oxygen atoms and for example may be an alcohol, aldehyde, ketone or epoxide group.

In further embodiments of the invention, the substrate is a halo aromatic compound. The halo aromatic compound is typically a benzene or biphenyl compound. The benzene ring is optionally fused and can be substituted. The halogen is typically chlorine. In many cases there is more than one halogen atom in the molecule, typically 2 to 5 or 6, for example 3. Generally 2 of the halogen atoms will be ortho or para to one another. The compound may or may not contain an oxygen atom such as a hydroxy group, an aryloxy group or a carboxy group. The compound may or may not be chlorophenol or a chlorophenoxyacetic acid compound.

Specific compounds which could be oxidized by the process of the present invention include 1,2-; 1,3- and 1,4-dichlorobenzene, 1,2,4-; 1,2,3- and 1,3,5-trichlorobenzene, 1,2,4,5- and 1,2,3,5-tetrachlorobenzene, pentachlorobenzene, hexachlorobenzene, and 3,3'-dichlorobiphenyl.

Other compounds which could be oxidized by the process include recalcitrant halo aromatic compounds, especially dioxins and halogenated dibenzofurans, and the corresponding compounds where one or both oxygen atoms is/are replaced by sulphur, in particular compounds of the dioxin class which possess at least one halo substituent, such as dioxin itself, 2,3,7,8-tetrachlorodibenzodioxin.

The oxidation of halo aromatic compounds typically gives rise to 1, 2 or more oxidation products. The atom which is oxidized may be a ring carbon. These oxidation products will generally comprise 1 or more hydroxyl groups. Generally, therefore, the oxidation products are phenols which can readily be degraded by a variety of *Pseudomonads* and other bacteria, whereas the unoxidized halo aromatic compounds are refractory to oxidation. As described below, this makes the enzyme of the invention suitable for decontamination of a locus contaminated with a halo aromatic compound.

Still further substrates contemplated for use in the processes of the invention include, but are not limited to chloraoxazone, aniline, p-nitrophenol, nifedipine, thujone diastereomers, alkenes (including propene, 1-hexene and styrene), indole, polycyclic aromatic hydrocarbons, propanolol, alkoxyresorufins (including 7-ethoxyresorufin, 7-methoxyresorufin, 7-penthoxyresorufin, 7-benzyloxyresorufin), buspirone, testosterone, amodiaquine, dextromethorphan, acetaminophen, 3,4-methylenedioxymethylamphetamine (MDMA).

The oxidation process carried out with a mutant CYP102A1 enzyme of the present invention may be differentiated from that carried out by another wild type or mutant CYP102A1 enzyme in terms of an improved coupling rate or rate of product formation, as defined above. The processes of the invention may also be characterized by formation of a specific product from the oxidized substrate, typically one which is not formed by the wild type CYP102A1 enzyme or another mutant CYP102A1 enzyme, or one which is formed in negligible quantities, i.e. less than 10%, 8%, 5%, 2%, 1% or less of the total amount of product. For example, oxidation of propylbenzene may produce 2-propylphenol, or 1-phenyl-2-propanol with high selectivity, or oxidation of ethylbenzene may produce 2-phenylethanol and styrene.

Processes carried out with the mutant CYP102A1 enzyme of the invention may also display an altered ratio or number of oxidation products, as compared to the oxidation process carried out by a wild type CYP102A1 enzyme or other mutant CYP102A1 enzyme. Where an altered ratio of products is present, the product formation rate for a specific oxidation product is typically increased with reference to the corresponding process carried out by a wild type CYP102A1 enzyme or other mutant CYP102A1 enzymes. The increase in the prevalence of a specific oxidation product may be at least 10%, 20%, 50%, more preferably 100%, 200%, 300%, 500% or more over the amount of said oxidation product in the product mixture as formed by the wild type CYP102A1 enzyme or other mutant CYP102A1 enzymes.

Specific examples of oxidation products that may show increased prevalence in the processes of the invention include: i) 1-phenyl-2-propanol, wherein the oxidized substrate is propylbenzene; ii) 2-ethylphenol, wherein the oxidized substrate is ethylbenzene; iii) 1-phenyl-2-butanol or 4-phenyl-2-butanol, wherein the oxidized substrate is butylbenzene; iv) benzylalcohol, wherein the oxidized substrate is toluene; v) 2-methyl-2-phenylpropan-1-ol, wherein the oxidized substrate is t-butylbenzene; vi) 2-methylbenzylalcohol, wherein the oxidized substrate is o-xylene; vii) carvacrol or thymol or 4-isopropylbenzylalcohol, wherein the oxidized substrate is p-cymene; viii) nootkatone, wherein the oxidized substrate is valencene; ix) 2-nonanol, wherein the oxidized substrate is nonane; x) 2-butanone or 2-butanol, wherein the oxidized substrate is butane; xi) 3-methyl-3-pentanol, wherein the oxidized substrate is 3-methylpentane; 2-propanol, wherein the oxidized substrate is propane; xiii) trans-isopiperitenol, wherein the oxidized substrate is R-limonene; xiv) 2,3-pinene epoxide, cis-verbenol, trans-verbenol, wherein the oxidized substrate is a-pinene; xv) 9-fluorenol, wherein the oxidized substrate is fluorene; xvi) 8-hydroxydodecanoic acid and 7-hydroxydodecanoic acid, wherein the oxidized substrate is lauric acid.

The process is typically carried out in the presence of the CYP102A1 enzyme, the substrate and the natural co-factors of the enzyme which are NADPH and dioxygen. In one embodiment the process is carried out with an enzyme such as a dehydrogenase and its co-substrate to regenerate the NADPH from NADP$^+$ with concomitant oxidation of the co-substrate of the dehydrogenase enzyme. In another embodiment the process is carried out by regenerating the NADPH co-factor by electrochemical methods known to those in the art.

It is understood that the increased activity and altered selectivity arise from substitutions in the haem domain of the CYP102A1 enzyme. The present invention therefore also provides for systems in which the substrate oxidation process is carried out in the presence of the haem domain of the enzyme (a), the substrate, an electron transfer reductase (b), an electron transfer redoxin (c), co-factor for the enzyme and an oxygen donor. In this system the flow of electrons is generally: co-factor→(b)→(c)→(a).

(b) is generally an electron transfer reductase which is able to mediate the transfer of electrons from the co-factor to (c), such as a naturally occurring reductase or a protein which has homology with a naturally occurring reductase, typically having at least 70% homology; or a fragment of the reductase or homologue. (b) is typically a reductase of any electron transfer chain found in naturally occurring P450 enzyme systems, and is typically a flavin dependent reductase, such as putidaredoxin reductase.

(c) is generally an electron transfer redoxin which is able to mediate the transfer of electrons from the co-factor to (a) via (b). (c) is typically a naturally occurring electron transfer redoxin or a protein which has homology with a naturally occurring electron transfer redoxin, typically having at least at least 70% homology; or a fragment of the redoxin or homologue. (c) is typically a redoxin of any electron transfer chain found in naturally occurring P450 enzyme systems. (c) is typically a 2Fe-2S redoxin, such as putidaredoxin, or a flavodoxin Typically (a), (b) and (c) are present as separate proteins; however they may be present in the same fusion protein. Typically only two of them, preferably (b) and (c), are present in the fusion protein. Typically these components are contiguous in the fusion protein and there is no linker peptide present.

Alternatively a linker may be present between the components. The linker generally comprises amino acids that do not have bulky side chains and therefore do not obstruct the folding of the protein subunits. Preferably the amino acids in the linker are uncharged. Preferred amino acids in the linker are glycine, serine, alanine or threonine. In one embodiment the linker comprises the sequence N-Thr-Asp-Gly-Gly-Ser-Ser-Ser-C. The linker is typically from at least 5 amino acids long, such as at least 10, 30 or 50 or more amino acids long.

In the process the concentration of the enzyme, (b) or (c) is typically from $10^{-8}$ to $10^{-2}$M, preferably from $10^{-7}$ to $10^{-4}$M. Generally the process is carried out at a temperature and/or pH at which the enzyme is functional, such as when the enzyme has at least 20%, 50%, 80% or more of peak activity. Typically the pH is from 3 to 11, such as 5 to 9 or 6 to 8, preferably 7 to 7.8 or 7.4. Typically the temperature is 10° C. to 90° C., such as 25° C. to 75° C. or 30° C. to 60° C.

In the process more than one different mutant CYP102A1 enzyme of the invention may be present. Typically each mutant will be able to oxidize different substrates or may be able to oxidize a given substrate better than another enzyme, and thus using a mixture of mutant CYP102A1 enzymes will enable a wider range of substrates to be oxidized. The process may also include wild type CYP102A1 enzymes, other P450 enzymes or their homologues, any monooxygenase enzyme, and any other enzyme useful in the desired synthesis or oxidation reaction.

In one embodiment the process is carried out in the presence of a substance able to remove hydrogen peroxide by-product (e.g. a catalase). In another embodiment the process is carried out in the presence of the full-length enzyme or the haem domain of the enzyme, substrate and an oxygen atom donor, such as hydrogen peroxide or t-butylhydroperoxide, for example using the peroxide shunt.

In a further embodiment, the process is carried out in the presence of the full-length enzyme or only the haem domain of the enzyme, substrate and oxygen in an electrochemical cell such that the two electrons required for oxygen activation and generation of the active intermediate are supplied by the electrode, either by direct electron transfer from the electrode or indirectly via a small molecule mediator.

The process may be carried out inside or outside a cell. The cell is typically in culture, at a locus, in vivo or in planta (these aspects are discussed below). The process is typically carried out at a locus such as in land (e.g. in soil) or in water (e.g. fresh water or sea water). When it is carried out in culture the culture typically comprises different types of cells of the invention, for example expressing different mutant CYP102A1 enzymes of the invention. Generally such cells are cultured in the presence of assimilable carbon and nitrogen sources.

Typically the cell in which the process is carried out is one in which the mutant CYP102A1 of the invention, or wild type CYP102A1 does not naturally occur. In another embodiment the mutant CYP102A1 enzyme is expressed in a cell in which wild type CYP102A1 does naturally occur, but at higher levels than naturally occurring levels. The cell may produce 1, 2, 3, 4 or more different mutant CYP102A1 enzymes of the invention. These mutant CYP102A1 enzymes may be capable of oxidising different organic compound substrates, different short-chain alkanes or different alkylbenzenes.

The cell may be prokaryotic or eukaryotic and is generally any of the cells or of any of the organisms mentioned herein. Preferred cells are *Escherichia coli*, *Pseudomonas* sp., flavobacteria or fungi cells (e.g. *Aspergillus* and yeast, especially *Pichia* sp.). Also contemplated for use according to the invention are *Rhodococcus* sp. and *Bacillus* sp. The cell may or not be one which in its naturally occurring form is able to oxidize any of the substrates or generate any of the oxidation products mentioned herein. Typically the cell is in a substantially isolated form and/or substantially purified form, in which case it will generally comprise at least 90%, e.g. at least 95%, 98% or 99% of the cells or dry mass of the preparation.

The cell is typically produced by introducing into a cell (i.e. transforming the cell with) a vector comprising a polynucleotide that encodes the mutant CYP102A1 enzyme of the invention. It is to be understood that due to the degeneracy of the nucleotide code, more than one polynucleotide can encode each of the mutant CYP102A1 enzymes of the invention. It is also to be understood that the nucleotide sequence may be engineered to exhibit a codon bias suitable for a particular cell or organism. The vector may integrate into the genome of the cell or remain extra-chromosomal. The cell may develop into the animal or plant discussed below. Typically the coding sequence of the polynucleotide is operably linked to a control sequence which is capable of providing for the expression of the coding sequence by the host cell. The control sequence is generally a promoter, typically of the cell in which the monooxygenase is expressed.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

The vector is typically a transposon, plasmid, virus or phage vector. It typically comprises an origin of replication. It typically comprises one or more selectable marker genes, for example an ampicillin resistance gene in the case of a bacterial plasmid. The vector is typically introduced into host cells using conventional techniques including calcium phosphate precipitation, DEAE-dextran transfection, or electroporation.

The invention further provides a transgenic animal or plant whose cells are any of the cells of the invention. The animal or plant is transgenic for one or more mutant CYP102A1 gene(s). They may be a homozygote or a heterozygote for such genes, which are typically transiently introduced into the cells, or stably integrated (e.g. in the genome). The animal is typically a worm (e.g. earthworm) or a nematode. The plant or animal may be obtained by transforming an appropriate cell (e.g. embryo stem cell, callus or germ cell), fertilizing the cell if required, allowing the cell to develop into the animal or plant and breeding the animal or plant if required. The animal or plant may be obtained by sexual or asexual reproduction (e.g. cloning), propagation of an animal or plant of the invention or of the F1 organism (or any generation removed from the F1, or the chimera that develops from the transformed cell).

As discussed above the process may be carried out at a locus. Thus the invention also provides a method of treating a locus contaminated with a substrate of the invention, for example a short chain alkane, an alkylbenzene or a halo aromatic compound. The method comprises contacting the locus with a mutant CYP102A1 enzyme, cell, animal or plant of the invention. These organisms are then typically allowed to oxidize the halo aromatic compound. In one embodiment the organisms used to treat the locus are native to the locus. Thus they may be obtained from the locus (e.g. after contamination), transformed/transfected (as discussed above) to express the mutant CYP102A1 (and optionally an appropriate electron transfer reductase and/or redoxin).

In one embodiment the locus is treated with more than one type of organism of the invention, e.g. with 2, 3, 4, or more types which express different monooxygenases which oxidize different organic compound substrates, for example different short chain alkanes, alkylbenzenes or halo aromatic compounds. In one embodiment such a collection of organisms between them is able to oxidize all substrates of a specific group, i.e. short chain alkanes that are present in the contaminated area.

The organisms (e.g. in the form of the collection) may carry out the process of the invention in a bioreactor (e.g. in which they are present in immobilised form). Thus the water or soil to be treated may be passed through such a bioreactor. Soil may be washed with water augmented with surfactants or ethanol and then introduced into the bioreactor.

Screening Design/Isolation of Mutants of the Invention

The methods disclosed to date for screening libraries of CYP102A1 mutants generated by random mutagenesis and gene shuffling have tended to use surrogate substrates such as indole (indigo formation) and p-nitrophenol derivatives (detection of p-nitrophenol released). Some of the selected mutants with enhanced oxidation activity for the surrogate substrate have been found to possess enhanced activity towards compounds with different structures but product selectivity changes are less common.

As regards screens for product selectivity, WO2006105082 disclosed a method for conjugating the product alcohol to a compound that can be detected spectroscopically. Similarly, increased selectivity for 1-octanol in octane oxidation by CYP102A3 was obtained by targeting this product in a dehydrogenase screening procedure (34). These approaches bias the search towards selectivity, with smaller increases in activity. Also, only those mutations that promote the formation of the specific target compound are found, while mutations at sites that affect product selectivity in different and potentially desirable manners towards a wider range of compounds are not revealed.

In contrast, the screening method used to isolate mutants according to the present invention utilizes a combination of screening a random library of mutants for indigo formation via indole oxidation followed by searching for enhanced activity and selectivity for products of chemical interest. Thus the most active mutants from the indole oxidation screen were further screened via in vivo oxidation of naphthalene, propylbenzene and octane. The products were analyzed by gas-liquid chromatography (see Examples section). Naphthalene is more hydrophobic than indole and more closely resembles the hydrocarbon substrates often targeted in P450 catalysis. Propylbenzene is smaller than naphthalene but poses a test for product selectivity changes because of competition between aromatic ring oxidation, benzylic oxidation, and attack at the two non-activated aliphatic carbon centers. Octane presents a different challenge being flexible and less compact, and having four different sets of C—H bonds available for oxidation, inviting mutations that bias selectivity towards terminal and internal positions. Variants with increased product formation rates and/or altered product profiles were selected for activity studies in vitro.

In this multi-step procedure ~1,500 colonies were screened in the initial indigo formation (activity) step, which number was reduced to ~800 colonies after gene shuffling of 11 of the first generation of mutants. 130 colonies out of these 800 were taken forward to the in vivo substrate oxidation screening steps. Of these 130, 5 variants were selected for further studies in vitro, all of which showed increased activity and/or altered product selectivity towards a broad range of organic compounds, from naphthalene to pentane. Thus, the screening method used to isolate mutants according to the present invention allows for efficient, stringent selection of mutants with increased activity and/or product selectivity. The small size of the initial library that was screened in the discovery of the mutations also indicates that the approach used by the Inventors for discovery of variants of CYP102A1 has yet to exhaust its potential.

A further difference to previously disclosed directed evolution techniques was that screening on CYP102A1 using indigo formation involved mutagenesis at specific sites (e.g. site saturation) in the CYP102A1 haem domain, whereas the present screening involved random mutagenesis of the full-length haem domain gene. Thus, the screen has the potential to isolate increased numbers of variants. Furthermore, it is clear that site-saturation mutagenesis could be applied to specific mutants isolated in accordance with the present invention so as to isolate further useful variants.

EXAMPLES

Materials and Methods

General reagents and chemical substrates of analytical grade or higher quality were from Alfa-Aesar, Fisher Scientific and Sigma-Aldrich or their subsidiary companies. Solvents of HPLC quality were from Rathburn Chemicals (UK) and subsidiaries of Sigma-Aldrich and Merck. Buffer components were from Anachem, UK. NADPH (tetrasodium salt) was from Apollo Scientific and Melford Laboratories. Isopropyl-$\beta$-D-thiogalactopyranoside (IPTG) was from Melford Laboratories. Restriction enzymes, T4 DNA ligase and the related buffers were from New England Biolabs. Taq and KOD Polymerases were from Merck Biosciences. Competent and supercompetent *E. coli* strains were from Stratagene. Site-directed mutagenesis was carried out using the PCR method described in the Stratagene Quik-Change mutagenesis kit. The appropriate lengths of oligonucleotide flanking the altered codon in the mutagenic oligonucleotides were designed following the manufacturers' instructions. Oligonucleotides were from MWG Biotech. General molecular biology manipulations were carried out according to literature methods (Sambrook, J., Fritsch, E. F., and Maniatis, T. (1989) *Molecular Cloning: A Laboratory Manual*, $2^{nd}$ Ed., Cold Spring Harbor Laboratory Press, New York). All mutant genes were fully sequenced on an automated ABI 377XL Prism DNA sequencer by the facility at the Department of Biochemistry, University of Oxford. UV/visible spectra and enzyme activity assays were run at 30° C. on a Varian Cary 50 spectrophotometer. $^1$H NMR spectra were acquired on a Varian UnityPlus 500 MHz spectrometer. Gas chromatography (GC) was carried out on Thermo Finnigan Trace and 8000 Top instruments equipped with flame-ionisation detectors (FIDs) using DB-1 fused silica capillary columns and helium as the carrier gas. The injectors were maintained at 200° C. or 250° C. and the FIDs at 250° C.

Mutagenesis, Design, Directed Evolution and Screening Procedures

A SpeI restriction site was introduced downstream of the pGLW11 haem domain-coding region (13) of the CYP102A1 gene using oligonucleotide:

5' GCTCATAATACGCCGCT<u>ACTAGT</u>GCTATACGGTTCAAATATG-3'
   (SEQ ID NO: 14)

(the SpeI recognition sequence underlined) and its reverse complement, resulting in silent mutations at residues 482 and 483.

Error-prone PCR was carried out between this site and an EcoRI site upstream of the haem domain-coding region using the forward and reverse primers:

5' TCTCGA<u>GAATTC</u>ATAATCATCGGAGACGCC-3';
   (SEQ ID NO: 15)

the EcoRI recognition sequence underlined); and

5'-TGGATCC<u>ACTAGT</u>AGCGGCGTATTATGAGC-3';
   (SEQ ID NO: 16)

the SpeI recognition sequence underlined).

Libraries were constructed from wild type CYP102A1 (WT) and mutant F87A templates under conditions designed to introduce 1-3 mutations per 1,000 bp according to the Stratagene GeneMorph protocol employed. Genes were amplified by 30 cycles of strand separation at 94° C. for 60 s, annealing at 45° C. for 90 s and extension at 68° C. for 110 s+2 s per cycle. After digestion with EcoRI and SpeI, short fragments were reincorporated into pGLW11 (SpeI WT variant) using T4 DNA Ligase, transformed into E. coli DH5α competent cells and grown for 36 h on Luria-Bertani (LB) agar plates.

Around 1500 colonies were screened. Those showing indigo formation (Gillam, E. M. J. et al (1999) Biochem. Biophys. Res. Commun. 265, 469-472; Li, Q. S., et al (2000) Chem. Eur. J. 6, 1531-1536) were isolated, transferred to fresh plates and grown for a further 36 h to minimise false positives prior to sequencing. 11 variants representing 16 new mutations of potential interest were then shuffled by random-priming recombination (Shao, Z., et al (1998) Nucleic Acids Res. 26, 681-683).

The protocol given by Volkov and Arnold (Volkov, A. A., and Arnold, F. H. (2000) Methods Enzymol. 328, 447-456) was modified at stage 9, where Taq and KOD Polymerases were employed with 2 µL MgSO$_4$ rather than Pfu Polymerase. PCR was carried out on the assembly strands as described above, but using KOD Polymerase. Samples were digested, ligated and plated out as before.

Of ~800 colonies, some 130 displayed indigo formation. These were grown up on a 5-10 mL scale and screened in vivo for naphthalene and propylbenzene oxidation activity using gas chromatography. The 12 variants that showed the largest increases in the product peak areas or altered product profiles compared to WT were sequenced, grown up on a larger scale and screened against the same two substrates. Of these, 5 were selected for studies in vitro.

We also prepared various single-site mutants and combinations thereof with the 5 mutants from the random mutagenesis screening procedure and examined these in vivo for indigo formation and for naphthalene, propylbenzene and octane oxidation activity using gas chromatography. The single-site mutations were R47L, Y51F, E267V, I263A, A74G, L188Q, M177V/K, A399P, I401P, G402P, Q403P, V302I, A264G, A99T, S270I, R179H, and F87L/A/G. The majority of these were previously known mutations (at R47, Y51, I263, A74, L188, M177, A264, F87) or ones we found in earlier rounds of the random mutagenesis/screening procedure (at E267, V302, A99, S270, R179) that were chosen for another round on the basis of their location in the structure being likely to have some effect on substrate binding. The proline mutations at A399, I401, G402 and Q403 were chosen based on the structural changes observed in the crystal structure of the A330P mutant (FIG. 2), one of the five mutants selected from the screening procedure. These mutants were then also screened by the in vivo screen method for evidence of increased activity.

The R47L and Y51F mutations, either on their own or when combined with other mutations, were not as effective as the R47L/Y51F couplet. The other single-site mutations showed different effectiveness in the indigo formation screen, while the I401P and Q403P single site mutants showed increased product formation over the wild type in the in vivo oxidation screen and these mutants were prepared and their activity studied in vitro. Variants R47L/Y51F (RLYF) and F87A were prepared as described (13). The RLYF couplet was introduced into variants KT2 and A330P using NcoI and AflII restriction sites in standard cloning procedures (Sambrook, J., Fritsch, E. F., and Maniatis, T. (1989) Molecular Cloning: A Laboratory Manual, 2$^{nd}$ Ed., Cold Spring Harbor Laboratory Press, New York). The F87A mutation was introduced to the KT2, I401P, RYLF/I401P, and RYLF/Q403P variants by site-directed mutagenesis. The I401P and Q403P mutation were introduced to the RLYF and RLYF/A330P variants by site-directed mutagenesis.

Protein Expression and Purification

Variants of interest were transferred into the pET28 vector using NcoI and BamHI restriction sites so that expression levels could be more tightly controlled with the T7 promoter over the tac promoter in the pGLW11 vector. 30 ml·L$^{-1}$ of an overnight culture of E. coli JM109(DE3) harbouring the plasmid was inoculated into LB medium containing 0.4% (v/v) glycerol and 30 mg·L$^{-1}$ kanamycin and grown at 37° C. with shaking at 180 rpm to an OD$_{600}$ of >1. Protein expression was induced by adding isopropyl-β-D-thiogalactopyranoside (IPTG) to 0.4 mM. The temperature was lowered to 30° C. and after a further 12 h of growth at 30° C. cells were harvested by centrifugation. The red-brown pellet from each 1 L growth was re-suspended in 25 mL 40 mM potassium phosphate buffered at pH 7.4, 1 mM in dithiothreitol (phosphate buffer). The cells were lysed by sonication, and cell debris was cleared by centrifugation at 37,500 g for 30 min at 4° C. The supernatant was loaded onto an Amersham-Pharmacia DEAE fast flow Sepharose column (200×50 mm) pre-equilibrated with phosphate buffer from which the protein was eluted using a linear gradient of 80-400 mM ammonium sulphate in phosphate buffer. The red P450 fractions were collected and concentrated by ultrafiltration, desalted using a Sephadex G-25 column pre-equilibrated with phosphate buffer, and re-concentrated by ultrafiltration. The solution was centrifuged at 9,250 g for 5 min at 4° C. and filter sterilised. FPLC anion-exchange purification was carried out on an Amersham-Pharmacia Source-Q column (120×26 mm) using a linear gradient of 0-30% 15× phosphate buffer. Fractions with A$_{418}$/A$_{280}$>0.35 were collected, concentrated by ultrafiltration and filter sterilised before being stored at −20° C. in 50% (v/v) glycerol. Glycerol and salts were removed from proteins immediately prior to experiments using an Amersham Pharmacia 5 ml PD-10 column pre-equilibrated with 50 mM Tris buffer at pH 7.4.

NADPH Turnover Rate Determinations

NADPH turnovers (except butane and propane) were run in 1250 µL of 50 mM Tris (pH 7.4) oxygenated at 30° C. and containing 0.1 or 0.25 µM enzyme, 125 µg bovine liver catalase and 1 mM substrate added as a 100 mM stock in DMSO. Protein concentration was determined as described (13) or via CO-difference spectra (Omura, T and Sato, R (1964) *J. Biol. Chem,* 239, 2379-85). Assays were held at 30° C. for 1 min prior to NADPH addition as a 20 mg·ml$^{-1}$ stock to a final concentration of ~160 μM or ~320 μM (equivalent to 1 or 2AU). In butane and propane turnovers, substrate was bubbled into 3000 μL of Tris on ice for a minimum of 30 minutes while oxygen was bubbled into 1000 μL of Tris, also on ice. CYP102A1 (0.25 μM) and catalase (concentration as above) were added gently to the oxygenated portion, followed by the substrate-saturated Tris. The full cuvette was promptly sealed, inverted several times, and held at 30° C. for 2 min prior to NADPH addition to 1 AU.

In all turnovers, absorbance decay at 340 nm was monitored and the NADPH consumption rate was derived using $\epsilon_{340}$=6.22 mM$^{-1}$ cm$^{-1}$. To ensure accurate coupling determination, enzyme concentrations of up to 2.5 μM were employed to drive the slower turnovers of WT and F87A to completion as necessary. Data from at least three experiments has been averaged to within ±5% (aromatics) or ±10% (alkalies and all turnovers with NADPH rates below 200 min$^{-1}$).

internal standard peak areas and plotted against product concentration. 2-methyl-2-phenyl-propan-1-ol, which could not be sourced commercially, was produced in vivo, isolated and identified by MS: M149.00; and $^1$H NMR: d 1.38 (6H, s, gem dimethyl), 3.59 (2H, s, CH$_2$), 7.24 (1H, m, p-phenyl), 7.34 (2H, m, m-phenyl), 7.37 (2H, m, o-phenyl). For lauric acid oxidation by CYP102A1 and its mutants, 990 μL of the incubation mixture was mixed with 10 μL of internal standard solution (25 mM decanoic acid in ethanol) and 2 μL of concentrated HCl. The mixture was extracted three times with 400 μL of ethyl acetate and the organic extracts were combined and dried over MgSO$_4$. Solvent was evaporated under a stream of dinitrogen and the sample dissolved in 200 μL acetonitrile. Excess (25 μL) N,O-Bis(trimethylsilyl)trifluoroacetamide with trimethylchlorosilane (BSTFA+TMCS, 99:1) was added and the mixture left for at least 120 min to produce the trimethylsilyl ester of the carboxylic acid group and trimethylsilyl ether of the alcohol, if formed. The reaction mixtures were used directly for GC analysis.

| Calibrants, internal standards and oven temperatures used in GC product analysis. | | | |
|---|---|---|---|
| Substrate | Calibrant | Internal Standard | Oven temperature, [Column length] |
| Propylbenzene | 1-phenyl-1-propanol | | Held at 60° C. for 1 min then raised at 15° C. min$^{-1}$ to 150° C. [7 m] |
| n-butylbenzene | 1-phenyl-2-butanol | | |
| Ethylbenzene | 1-phenyl-1-ethanol | | |
| Toluene | o-cresol | | |
| o-xylene | 2-methylbenzylalcohol | 4-benzylphenol | |
| m-xylene | 2-methylbenzylalcohol | | |
| t-butylbenzene | 4-t-butylphenol | | |
| p-cymene | p-αα-trimethyl benzylalcohol | | |
| cumene | 2-phenyl-2-propanol | | |
| R- & S-limonenes | Perillyl alcohol | | |
| fluorene | 9-fluorenol | | |
| 1,4-dichlorobenzene | 2,5-dichlorophenol | | |
| α-pinene | α-pinene oxide | | |
| β-ionone | α-ionone epoxide | | |
| Octane | 2-octanol | | Held at 40° C. for 1 min then raised at 15° C. min$^{-1}$ to 130° C. [7 m] |
| Naphthalene | 1-naphthol | | Held at 100° C. for 1 min then raised at 15° C. min$^{-1}$ to 220° C. [7 m] |
| Valencene | nootkatone | 1-undecanol | |
| Lauric acid | 12-hydroxylauric acid | decanoic acid | |
| Pentane | 3-pentanol | 2-octanol | Raised from 70° C. to 90° C. at 1° C. min$^{-1}$ then raised at 65° C. min$^{-1}$ to 220° C. [60 m] |
| 3-methylpentane | 3-methyl-2-pentanol | | |
| 2-methylbutane | 3-methyl-2-butanol | | |
| Butane | 2-butanol | 3-pentanol | Raised from 60° C. to 80° C. at 2° C. min$^{-1}$ then raised at 70° C. min$^{-1}$ to 220° C. [60 m] |
| Propane | 2-propanol | | |

Product Analysis

For substrates other than lauric acid, 3 μL of internal standard (100 mM in DMSO) was added to 1000 μL of each completed turnover prior to extraction into 400 μL ethyl acetate or chloroform. Centrifugation was carried out at 21,000 g for 3½ min in 1500-μL microcentrifuge tubes. Products were identified by matching the GC elution times observed to those of authentic equivalents. FID responses were calibrated using a representative equivalent for each product group as detailed in the table below, using the assumption that isomeric mono-oxygenated products give comparable responses. Samples containing a range of known concentrations of the chosen product and 1 mM in DMSO were prepared in Tris and extracted as above. The integrated peak areas derived were expressed as ratios of the Results Of the variants generated by random mutagenesis which were screened both for enhanced activity and altered product selectivity in vivo, five specific variants were selected for in vitro studies. These were:
(i) A330P
(ii) A191T/N239H/I259V/A276T/L353I (Mutant KT2)
(iii) F87A/H171L/Q307H/N319Y (Mutant KSK19)
(iv) F87A/A330P/E377A/D425N (Mutant KT5)
(v) F87A/A117V/E131D/L215I (Mutant LO25)

All five mutants were readily expressed and purified by standard procedures (13). None showed evidence of formation of the inactive, "P420" form upon storage at −20° C. in 50% v/v glycerol for at least 15 months. Mutant LO25 has been less studied than the other four variants but it has the highest activity and selectivity of these five initial mutants for the damascone/ionone class of molecules, e.g. forming 86% of a hydroxydamascone product. The activities of A330P, KT2, KSK19, and KT5 were assayed with a wide range of substrates. The data for some of these are given in Tables 1 to 20 where the NADPH oxidation and product formation rates (PFR) are given in units of nmol (nmol P450)$^{-1}$ min$^{-1}$ and abbreviated to min$^{-1}$ henceforth in the text. The coupling efficiency is the yield of product based on the NADPH consumed and is given as a percentage. In some cases the catalytic parameters are compared to the A74G/F87V/L188Q (GVQ) mutant disclosed in NO20020380.

Four variants of the invention (A330P, KT2, KT5, KSK19) enhanced the PFR of WT with naphthalene (3.1 min$^{-1}$) by at least an order of magnitude, A330P being the most effective at 155 min$^{-1}$, though none could match the 487 min$^{-1}$ recorded by the GVQ variant (Table 1). In all cases 1-naphthol was the only GC-detectible product (23).

WT was considerably more active towards propylbenzene at 606 min$^{-1}$, with 70% coupling. Three of the four variants of the invention have a similar PFR to that of the GVQ variant (943 min$^{-1}$), while the fourth, KT2 significantly exceeded it at 2205 min$^{-1}$ (Table 2). WT and KT2 yielded ≥99% 1-phenyl-1-propanol, but the other new variants directed oxidation away from the activated benzylic position. Variant A330P gave 30% of the ortho-phenol, a product type not previously reported in CYP102A1 turnovers, while variant KT5, in which mutations F87A and A330P occur in combination, gave 80% 1-phenyl-2-propanol. Mutation F87A is known to promote 1-phenyl-2-propanol formation, but yields only 54% when acting alone (46).

The R47L/Y51F (RLYF) couplet, which had been shown to increase CYP102A1 activity for several substrates (13,14, 17), was incorporated into variants A330P and KT2, with the aim of further raising product formation rates. Two highly active second generation variants resulted, RLYF/KT2 and RLYF/A330P. Single-site mutations were also introduced at various residues around the haem surface as well as the active site, and these were also combined with the 5 mutants identified in the first round. The activity of these second generation mutants were screened by the indigo formation and in vivo oxidation screening procedure. The I401P and Q403P mutants were identified as promising new variants from the in vivo oxidation procedure and they were prepared. The combination variants R47L/Y51F/I401P, F87A/I401P and R47L/Y51F/A330P/I401P were also prepared.

RLYF/KT2 matched the PFR of the GVQ variant in naphthalene turnovers at 496 min$^{-1}$, RLYF/A330P, at 666 min$^{-1}$, exceeded it by some 35% while I401P was still more active, at 1183 min$^{-1}$. Q403P showed a PFR of 121 min$^{-1}$ and 25% coupling, which were similar to the values for the variant KT2. The PFR of RLYF/KT2 with propylbenzene was 2688 min$^{-1}$, a 22% improvement over KT2. This rate approaches those reported for WT with natural substrates (47) while I401P at 3578 min$^{-1}$ exceeded the rates for natural substrates. Product profiles were little altered relative to the first generation variants, though RLYF/A330P gave some p-propylphenol (Table 2). KT2 was also combined with mutation F87A in order to make F87A-directed product profiles available at higher rates. Variant F87A/KT2 oxidized propylbenzene to 1-phenyl-1-propanol and 1-phenyl-2-propanol in roughly equal quantities, in line with mutant F87A, but at a PFR of 566 min$^{-1}$ versus 241 min$^{-1}$ for F87A.

Other alkylbenzenes were also examined as substrates for WT CYP102A1 and the new variants. Dramatic activity enhancements were observed with toluene (Table 3), in particular with RLYF/KT2, RLYF/A330P and I401P. The effect of the Q403P mutant was again similar to that of variant KT2. Large selectivity shifts were also evident, albeit for variants with lower product formation rates than the fastest mutants. WT CYP102A1 oxidized toluene predominantly to o-cresol (98%). This ring oxidation was unexpected since the benzylic C—H bonds are highly activated. For instance, WT CYP101A1 from *Pseudomonas putida* attacked the benzylic position to form >95% benzyl alcohol. Variant RLYF/A330P increased the PFR by a factor of 60 to 189 min$^{-1}$, coupling efficiency rising from 9% to 52% while keeping side-chain oxidation at a minimum. Addition of the I401P mutation gave rise to another increase in activity, with the NADPH and substrate oxidation rates rising to 3732 min$^{-1}$ and 1824 min$^{-1}$, respectively. Notably the coupling efficiency of 49% was largely unchanged from that of the RLYF/A330P (52%) and indeed the A330P (45%) variant, indicating that the main effect of the I401P mutation is enhanced NADPH turnover rate. Other variants showed both increased turnover activity and altered selectivity, e.g. variant F87A/KT2 gave 48% benzyl alcohol while variant KT5 yielded 95% benzyl alcohol and just 5% o-cresol (Table 3).

NADPH rates and coupling were generally lower with butylbenzene than propylbenzene, PFRs of 229 min$^{-1}$ and 1670 min$^{-1}$ being recorded for WT and the fastest variant, RLYF/KT2 (Table 4). Hydroxylation was no longer exclusively benzylic even within the WT-RLYF/KT2 sub-group, ~10% taking place at each of the next two positions of the side-chain. Most other specificity changes mirrored those observed with propylbenzene. F87A variants increased oxidation at the non-benzylic positions—to as much as 80% with KT5—while variant F87L/KT2 formed substantial quantities of o-butylphenol (32%). However, A330P favored p-butylphenol formation, particularly when in combination with RLYF (26%), while cutting benzylic oxidation levels to just 10-13%.

With t-butylbenzene the NADPH turnover rates were in line with those for butylbenzene for most variants, but coupling levels were much reduced except in the case of F87A variants, (Table 5). The GVQ variant, F87A/KT2 and KSK19 all improved PFRs by two orders of magnitude relative to WT, the highest rate being given by the new variant F87A/KT2 at 234 min$^{-1}$ versus 2.4 min$^{-1}$ for WT. F87A and F87V variants hydroxylated exclusively at the non-activated C—H bonds of the side chain to yield 2-methyl-2-phenyl-1-propanol, a compound that is awkward to synthesize by conventional methods. The majority of the products formed by WT and other variants were phenolic, with para-hydroxylation preferred over ortho-hydroxylation but again the A330P mutation increased the propensity for aromatic oxidation, shifting the product further to the para-phenol.

With ethylbenzene (Table 6) the variants of the invention generally showed enhanced activity over the WT (60 min$^{-1}$). RLYF/KT2, the fastest variant, gave a PFR of 1098 min$^{-1}$. RLYF/A330P also gave a high PFR (1062 min$^{-1}$), partly because A330P variants coupled better with ethylbenzene than WT (55-62% versus 28%). The coupling rates of Phe87 variants, by contrast, remained lower than those of WT (22-30%). WT again showed lower specificity for the benzylic position than in propylbenzene turnovers, forming 10% o-ethylphenol. A330P-containing mutants formed higher percentages of this product (21-27%), while F87A and F87V variants such as KSK19 and GVQ eliminated it from the product mix and yielded 100% 1-phenylethanol. KT5 turnovers produced small quantities of two other products: 2-phenylethanol and styrene. The former arises from oxidation at the non-activated, primary C—H bonds of the ethyl substituent while the latter represents the first observation to the Inventors' knowledge of dehydrogenation of a simple hydrocarbon catalyzed by CYP102A1.

Preferential attack at a methyl group next to an activated benzylic carbon is difficult to achieve because if these two types of bonds are at the same distance from and equally accessible to the P450 ferryl intermediate then the more activated C—H bond is attacked more rapidly. Hence KT5 may bind ethylbenzene in an orientation that places the methyl C—H bonds closer to the ferryl than the benzylic C—H bonds. In the dehydrogenation reaction the ferryl intermediate abstracts a hydrogen atom to form the $Fe^{IV}$—OH intermediate and the substrate radical then, instead of collapsing by recombining with the hydroxyl radical from the $Fe^{IV}$—OH moiety, abstracts a second hydrogen atom from the substrate to form the alkene and water. Dehydrogenation of 3-methylindole by a mammalian P450 enzyme was first reported in 1996 and this has since been extended to dehydrogenation by human P450 enzymes of indoline, capsaicin, and drugs (48-52). Aromatization of nifedipine via dehydrogenation by CYP102A1 has been reported (53). However, this reaction is driven by the formation of two delocalized aromatic systems.

The naturally occurring hydrocarbon, p-cymene (4-isopropyltoluene), is an interesting substrate as it is a precursor to four flavouring compounds. WT gave 82% p-α,α-trimethylbenzylalcohol, which arises from oxidation of the methine C—H bond of the isopropyl side-chain. Small quantities of the two possible aromatic hydroxylation products, thymol (3%) and carvacrol (7%) were also formed, and just 2% 4-isopropylbenzylalcohol. By contrast, variant A330P gave 19% thymol, 17% carvacrol, 22% 4-isopropylbenzylalcohol, and only 37% p-α,α-trimethylbenzylalcohol (Table 7). F87L/KT2 gave 74% 4-isopropylbenzylalcohol and 21% carvacrol, with the usual majority product, p-α,α-trimethylbenzylalcohol accounting for just 5% of the product mix. Activity enhancements were observed, with variant KSK19 giving a PFR of 1442 $min^{-1}$ versus 168 $min^{-1}$ for WT. p-α-Dimethylstyrene was formed via dehydrogenation of the isopropyl ring substituent. Moreover, once formed, this compound is also a substrate for the enzyme, and small quantities (1-3% of the total products) of the corresponding styrene oxide were observed. F87A- and F87V-containing variants minimized or eliminated phenol formation but gave significant quantities (>20%) of p-α-dimethylstyrene.

The variants of the invention showed increased cumene oxidation activity. The single-site mutants A330P and Q403P, and the KSK19 variant showed similar enhanced activity over the wild type, primarily due to increased NADPH turnover rates that were also higher than for the KT5 variant. The WT formed mostly the benzylic oxidation product while KT5 gave 27% 1-methylstyrene from dehydrogenation and also 1% of the styrene oxide product from further oxidation (Table 8a). The results show that an aromatic compound with a primary C—H bond in the 2-position of an alkyl substituent can give rise to dehydrogenation. This reaction pathway can form the basis of a method for synthesizing substituted styrenes which are precursors to polymers, e.g. preparation of vinylanisole from ethylanisole.

KT2 and A330P showed greatly enhanced activity towards short-chain alkanes compared to the wild type, particularly when in combination with RLYF (Tables 9-13). The I401P mutant also proved to be highly active. RLYF/KT2 and RLYF/A330P displayed similar product formation rates with pentane (1206 $min^{-1}$ and 1183 $min^{-1}$, based on coupling efficiencies of 60% and 67% respectively) that were 75 times those of the WT. The gain in coupling efficiency in these mutants is important since it shows greatly improved match between the active site topology and the substrate.

The high activities of these variants were maintained through 3-methylpentane (all >1000 $min^{-1}$ vs. ~20 $min^{-1}$ for the WT, Table 10), 2-methylbutane (both RLYF/KT2 and RLYF/A330P>1000 $min^{-1}$ with I401P less active at 721 $min^{-1}$ vs. 51 $min^{-1}$ for WT, Table 11), and butane. The I401P mutation on its own mainly increased the NADPH turnover rate, and it combined well with the RLYF couplet, raising the PFR for 3-methylpentane oxidation to 2980 $min^{-1}$. On the other hand triple mutant RLYF/A330P displayed markedly better coupling than RLYF/KT2 with propane, forming 2-propanol at 46 $min^{-1}$ versus 5.8 $min^{-1}$. Addition of the I401P mutation increased the NADPH turnover rate, with a modest increase in coupling, leading to a PFR for propane oxidation of 430 $min^{-1}$ for the RLYF/A330P/I401P mutant. These rates compare to the 23 $min^{-1}$, 160 $min^{-1}$ and 370 $min^{-1}$ rates for previously reported CYP102A1 variants 9-10A, 1-12G and 53-5H, successive generations of alkane hydroxylases containing 13-15 mutations apiece (30,31). The GVQ variant used as a comparison gave a higher NADPH turnover rate than RLYF/A330P with propane (400 $min^{-1}$ versus 180 $min^{-1}$). As far as we are aware, its proficiency with this substrate has not been reported. However, coupling was only 0.7% versus 21% for RLYF/A330P. This is an extreme but characteristic example of how A330P and KT2 compare to GVQ across the range of substrates studied. Although NADPH rates of these two variants are often lower, overall product formation rates are generally higher on account of more efficient coupling. When this property is combined with the I401P mutation that mainly increased the turnover rate the resultant mutants, such as the R47L/Y51F/A330P/I401P, can achieve extraordinary activity increases over the wild type for a range of non-natural substrates.

Longer chain alkanes were poorer substrates for most mutants, RLYF/KT2 and RLYF/A330P giving PFRs of 246 $min^{-1}$ and 230 $min^{-1}$ with octane respectively, versus 53 $min^{-1}$ for WT (Table 13). Q403P showed a modest increase in activity of 2-fold over the wild type, to a PFR of 104 $min^{-1}$ while I401P was more active at 709 $min^{-1}$. RLYF/KT2 and I401P showed similar product selectivity to the wild type, but variant A330P significantly enhanced 2-octanol formation (53%, compared to 15% for WT, Table 13) at the expense of 3- and 4-octanol (31,54). This effect of directing oxidation of an alkane in the direction of the terminal positions is a useful asset for combining with other mutations in the overall search for terminal alcohol synthesis via direct alkane oxidation.

The variants of the invention also showed increased activity for oxidizing chlorinated aromatic compounds, as exemplified by 1,4-dichlorobenzene (1,4-DCB). The increases were mainly due to higher NADPH turnover activity while the couplings were not much higher than the WT. The highest coupling was 15% with the A330P variant (Table 14). Only one product was detected by gas chromatography but under the conditions used it was not possible to determine whether this was 2,4- or 2,5-dichlorophenol. The results demonstrated the efficacy of the variants of the invention for chlorinated benzene and aromatic oxidation.

We had previously reported oxidation of the sesquiterpene valencene by WT CYP102A1 and mutants such as F87A (14). The enzymes formed numerous products, including nootkatols, nootkatone and epoxidation products. The F87A mutation was shown to shift the product selectivity slightly towards nootkatone (~20%). In comparison, variant KSK19 increases the oxidation rate of valencene 30-fold relative to the WT (Table 15). More crucially, it doubles the production rate of the grapefruit flavoring, nootkatone, relative to mutant F87A. Variants F87A/KT2 and KT5 increased the proportion of nootkatone to ~30% while also raising the PFR over F87A on its own.

WO0031273 disclosed monoterpene oxidation by CYP102A1. The new variants showed higher activity than the WT and previously reported mutants. The catalytic properties of the new variants are compared with those of the WT for R- and S-limonene oxidation (Table 16; 16a). It is particularly notable that the two enantiomers formed different products with both enzymes but the turnover activities and couplings are closely similar, demonstrating the asymmetric nature of the CYP102A1 substrate pocket. Limonene oxidation activity was increased across all variants, with the Q403P, I401P and the R47L/Y51F/I401P triple mutant showing activities that were comparable or higher than that for the oxidation of a fatty acid natural substrate (lauric acid) by wild type CYP102A1 (1439 $min^{-1}$, see Table 20). Again these mutants showed similar product selectivity to the wild type, forming mainly the carveols, while the A330P- and F87A-containing mutations had altered selectivity, with the isopiperitenols being the major products. It is also clear that both KT2 and I401P functioned well as generic accelerator mutations. With (+)-α-pinene, the WT possessed little activity while the F87A/KT2 variant had a PFR of 206 $min^{-1}$ and shifted the product selectivity towards verbenol (Table 17). The effect of introducing the F87G mutation will be of interest. The I401P and F87A/I401P mutants were more active while maintaining the verbenols as the major products. Combination of I401P with the R47L/Y51F couplet raised the PFR to 1146 $min^{-1}$ but shifted the product to 56.5% of the cis-1,2-oxide, a selectivity trend that was further reinforced by the A330P mutation.

Fluorene is a more sterically demanding substrate than naphthalene, that was used in the in vivo screening procedure. The R47L/Y51F combination raised the activity slightly, and adding the A330P mutation increased the NADPH turnover rate to 510 $min^{-1}$ but the coupling efficiency was low (Table 18). The Q403P and I401P mutations had more significant effects, and the R47L/Y51F/I401P combination was particularly active, with a PFR of 582 $min^{-1}$ compared to 0.1 $min^{-1}$ for the wild type. The ionone class of compounds are precursors to flavouring compounds. Table 19 shows the β-ionone oxidation activity of wild type and some of the new variants, highlighting the activity increases possible with combination variants such as the R47L/Y51F/I401P.

Lauric acid (dodecanoic acid) is a recognized natural substrate of CYP102A1, with a NADPH turnover rate of 2777 $min^{-1}$ and PFR of 1439 $min^{-1}$. The structural perturbations introduced by the A330P mutation virtually abolished lauric acid oxidation by CYP102A1, while the I401P mutation enhanced the NADPH turnover rate while maintaining the coupling efficiency, leading to a mutant that is 40% more active than the wild type for the oxidation of a natural substrate. Clearly the rate of the first electron transfer is increased, suggesting a change in redox potential, haem spin state and reorganization energy for the process in this mutant. The R47L/Y51F/I401P mutant showed an even higher NADPH turnover rate but the coupling was lowered, presumably because the R47 and Y51 side chains were not available for carboxylate anchoring, altering the binding and hence coupling. The F87A mutation is known to shift lauric acid oxidation towards sub-terminal carbons, and the I401P mutation increased the activity while maintaining the selectivity altering effect of the F87A mutation.

These findings show that, despite the significant body of prior art, the CYP102A1 system remains fertile ground for the application of directed evolution and site-directed mutagenesis techniques, and that variants with improved activity and product selectivity can be characterised. All of the variants of the invention contain a number of mutations that to the Inventors' knowledge have not been disclosed previously.

The A330P mutation has the sought-after effect of increasing the activity towards a wide range of compounds while also altering the product profile when acting on its own as well as when combined with another selectivity-altering mutation (F87A). On the other hand, I401P functions as a generic rate accelerator with little effect on selectivity. I401 is on a β-bulge close to the haem and may affect electron transfer. A330P is an unlikely directed evolution product, relying for its potency on a solitary substitution derived from a single point mutation rather than a concert party of altered residues, as is common. Proline is introduced directly beside an existing proline at position 329, a substrate contact residue at the end of a β-strand. The resulting loss of backbone flexibility was predicted, and appears from the crystal structure (FIG. 2) to constrict the active site pocket, allowing tighter substrate binding and enhancing activity. This explanation is consistent with the unusual and potentially useful selectivity effects observed, which are typically the converse of those brought about by F87A, where the active site pocket is more open than in WT. It will be interesting to see whether the tactic of juxtaposing proline residues can usefully be deployed elsewhere in CYP102A1, or indeed in the redesign of other enzyme systems.

Figure 2:
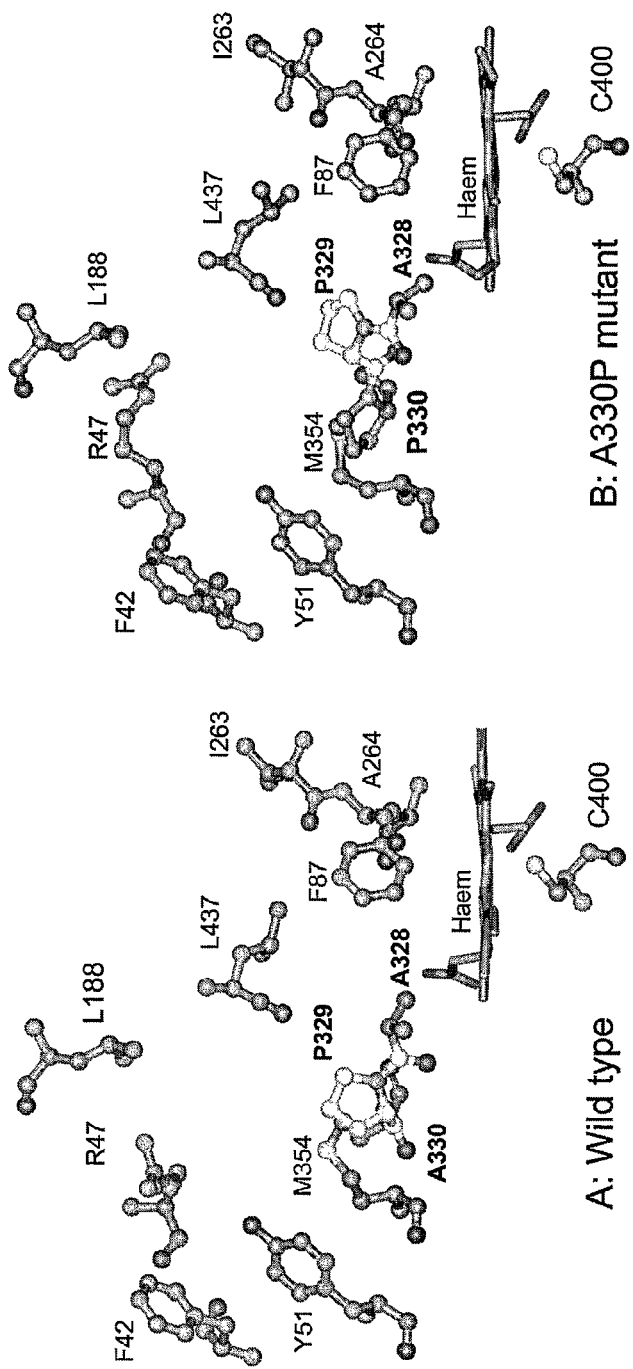
FIG. 2: Comparison of key residues in the substrate access channel and active site of wild type CYP102A1 and the A330P mutant, highlighting the structural perturbations at P329 and A328 resulting from the A330P mutation.

The crystal structure of the A330P mutant was obtained, and is shown in FIG. 2. The Calpha positions of this mutant were largely superimposable on those of the wild type, but there was significant rearrangement at positions 328, 329 and 330. As shown in FIG. 2, the introduced A330P mutation induced a dramatic shift of the ring of Pro329 towards the substrate binding pocket, reducing the active site volume and constricting the substrate access channel in a critical region. These structural changes most likely led to the unusual effects observed with the A330P mutation, such as the enhanced binding of non-natural substrates and altered product selectivity, due to the protrusion of the Pro329 ring into the substrate pocket. However they did not cause abrupt termination of secondary structure elements such as a helix.

Based on these unexpected findings, the potential for restructuring loop regions by introducing bulky residues such as proline was investigated further. Specifically, proline substitutions were carried out in the Ala399-Gln403 loop, which provides the proximal haem ligand, Cys400. Arg398 is involved in electrostatic and hydrogen bonding interactions, and may be important in stabilising the protein fold, while residues beyond Gln403 are probably too far removed from the haem to have any effects. The mutations explored were therefore A399P, I401P, G402P and Q403P. As shown in the Examples section, both I401P and Q403P brought significant enhancements to enzymic activity.

Mutating residues 401 and 403 to proline may induce conformational changes in the proximal loop so as to alter the strength of the Fe—S bonding interaction, e.g. by altering the Fe—S distance. This could render the haem iron easier to reduce, the reorganisation energy barrier to electron transfer would be lowered, as would the ease with which the haem iron could move into the plane of the porphyrin ring during the catalytic cycle.

The reorganisation of loop regions in CYP102A1 via the incorporation of bulky residues such as proline is a distinct and specific structural mechanism that is common to the A330P, I401P and Q403P substitution mutants of the current Invention.

Variant KT5, in which A330P and F87A occur together, promotes selectivity changes characteristic of F87A rather than A330P. However the shifts involved can be more pronounced than those brought about by other F87A-containing variants (e.g. 95% benzyl alcohol from toluene versus 48% with F87A/KT2, 23% with F87A and 2% with WT), and often occur at enhanced product formation rates, creating a range of complementary possibilities. It will be interesting to see how A330P combines with other known selectivity-directing mutations such as A264G, A82L and A328V.

Variants KT2 (A191T/N239H/I259V/A276T/L353I) and F87A/KT2 give product profiles that closely resemble those of WT and variant F87A respectively. Similarly I401P accelerated the rate for a range of substrates with identical product outcomes as the wild type. Hence KT2 and I401P function as rate accelerators. Component mutations N239H and I259V in KT2 are previously reported (55). However, variant KSK19, which contains an incipient F87A, has the same selectivity pattern as F87A/KT2 and is slightly more active across a range of substrates despite containing only three other mutations, suggesting that the F87A-free derivative of KSK19 may prove more potent than KT2 as a rate accelerator when it is prepared.

Of the mutations that appear to be acting as rate accelerators in KT2 and KSK19 (H171L, A191T, N239H, I259V, A276T, Q307H, N319Y and L353I), Gln307 and Asn319 (FIG. 1) are close to the region thought to be the docking site for the reductase domain from which the haem domain receives electrons (56), and may be able to influence electron transfer kinetics. Leu353 lies next to a substrate access channel residue, Met354, while Ala191, which is situated on the outer lip of the access channel, is noticeably displaced when palmitate binds (57), and could play a role in substrate enticement and/or capture. The remaining four mutations (His171, Asn239, Ile259, Ala276) are on or close to the protein surface and the detail mechanisms by which they function remain to be elucidated. It is speculated that the effects of at least some of the mutations may be rationalized in terms of their context in the CYP102A1 structure. The turnover activity of P450 enzymes is rate-limited by the rate of the first electron transfer step that initiates the catalytic cycle. The rate of electron transfer reactions are commonly discussed in terms of Marcus theory, which states that the activation energy to electron transfer depends of the thermodynamic driving force (the free energy change of the reaction) and the reorganization energy (energy input required to distort the reactant state to resemble the product state). Substrate binding plays a major role by altering the electronic properties of the haem, in most cases the sixth ligand to the haem iron is displaced, thus making the reaction thermodynamically more favorable (higher driving force) and lowering the reorganization energy barrier (less distortion of the reactant state is needed) for electron transfer (58). If the active site structure is altered, e.g. by an active site substitution, binding of non-natural substrates could be enhanced, and faster substrate oxidation is observed.

Another mechanism for altering substrate binding (and hence the electronic properties of the haem) may be induction of changes in the secondary structure elements surrounding the substrate pocket. In P450 enzymes, the substrate pocket is usually defined by residues from the B and B' helices, the BC loop, the F/G loop, the G helix and the I helix. Amino acid substitutions at residues far away from the substrate pocket can alter substrate binding by inducing changes in the positions of these secondary structure elements. His171 is at the beginning of the F helix and contacts the G helix at L215. N239 is in the H helix and this helix contacts the N-terminal end of the I helix. Substitutions at H171 and N239 will affect the positioning of the G and I helices, respectively and can alter substrate binding. Ile259 and Ala276 are both in the I helix. Although these residues do not contact the substrate, amino acid substitutions may affect the active site structure, for example by inducing structural changes in the intervening residue, I263, which is located in the active site, and has been shown to alter the activity of CYP102A1 in the Inventors' earlier work (13).

It is of particular interest to note that variant LO25 contains the L215I mutation which can affect the contact between the F and G helices at the H171/L215 close approach. Overall, whilst none of the mutations are in the active site, all of them are at residues that play some role in the packing/interactions between secondary structure elements. The tandem-proline arrangement introduced by the A330P is unique and shows very unexpected but highly beneficial effects.

The mutations disclosed in the present invention may be introduced to existing variants (e.g. those containing the L188Q, R47L, Y51F mutations) for process development but also as starting points for further evolution.

REFERENCES

1. Miura, Y., and Fulco, A. J. (1975) *Biochim. Biophys. Acta* 388, 305-317.
2. Cryle, M. J., Espinoza, R. D., Smith, S. J., Matovic, N. J., and De Voss, J. J. (2006) *Chem Commun,* 2353-2355.
3. Ravichandran, K. G., Boddupalli, S. S., Hasemann, C. A., Peterson, J. A., and Deisenhofer, J. (1993) *Science* 261, 731-736.
4. Li, H., and Poulos, T. L. (1997) *Nature Struct. Biol.* 4, 140-146.
5. Munro, A. W., Leys, D. G., McLean, K. J., Marshall, K. R., Ost, T. W., Daff, S., Miles, C. S., Chapman, S. K., Lysek, D. A., Moser, C. C., Page, C. C., and Dutton, P. L. (2002) *Trends Biochem. Sci.* 27, 250-257.
6. Urlacher, V. B., Lutz-Wahl, S., and Schmid, R. D. (2004) *Appl. Microbiol. Biotechnol.* 64, 317-325.
7. Bell, S. G., Hoskins, N., Whitehouse, C. J. C., and Wong, L.-L. (2007) *Metal Ions Life Sci.* 3, 437-476.
8. Graham-Lorence, S., Truan, G., Peterson, J. A., Falck, J. R., Wei, S., Helvig, C., and Capdevila, J. H. (1997) *J. Biol. Chem.* 272, 1127-1135.
9. Oliver, C. F., Modi, S., Sutcliffe, M. J., Primrose, W. U., Lian, L. Y., and Roberts, G. C. K. (1997) *Biochemistry* 36, 1567-1572.
10. Noble, M. A., Miles, C. S., Chapman, S. K., Lysek, D. A., Mackay, A. C., Reid, G. A., Hanzlik, R. P., and Munro, A. W. (1999) *Biochem. J.* 339, 371-379.
11. Cowart, L. A., Falck, J. R., and Capdevila, J. H. (2001) *Arch. Biochem. Biophys.* 387, 117-124.
12. Oliver, C. F., Modi, S., Primrose, W. U., Lian, L. Y., and Roberts, G. C. K. (1997) *Biochem. J.* 327, 537-544.
13. Carmichael, A. B., and Wong, L. L. (2001) *Eur. J. Biochem.* 268, 3117-3125.
14. Sowden, R. J., Yasmin, S., Rees, N. H., Bell, S. G., and Wong, L. L. (2005) *Org. Biomol. Chem.* 3, 57-64.
15. Lussenburg, B. M., Babel, L. C., Vermeulen, N. P., and Commandeur, J. N. (2005) *Anal Biochem* 341, 148-155.
16. Wong, T. S., Wu, N., Roccatano, D., Zacharias, M., and Schwaneberg, U. (2005) *J Biomol Screen* 10, 246-252.
17. Urlacher, V. B., Makhsumkhanov, A., and Schmid, R. D. (2006) *Appl. Microbiol. Biotechnol.* 70, 53-59.
18. van Vugt-Lussenburg, B. M., Damsten, M. C., Maasdijk, D. M., Vermeulen, N. P., and Commandeur, J. N. (2006) *Biochem. Biophys. Res. Commun.* 346, 810-818.

19. van Vugt-Lussenburg, B. M., Stjernschantz, E., Lastdrager, J., Oostenbrink, C., Vermeulen, N. P., and Commandeur, J. N. (2007) *J. Med. Chem.* 50, 455-461.
20. Maves, S. A., Yeom, H., McLean, M. A., and Sligar, S. G. (1997) *FEBS Lett.* 414, 213-218.
21. Li, Q. S., Schwaneberg, U., Fischer, P., and Schmid, R. D. (2000) *Chem. Eur. J.* 6, 1531-1536.
22. Appel, D., Lutz-Wahl, S., Fischer, P., Schwaneberg, U., and Schmid, R. D. (2001) *J. Biotechnol.* 88, 167-171.
23. Li, Q. S., Ogawa, J., Schmid, R. D., and Shimizu, S. (2001) *Appl. Environ. Microbiol.* 67, 5735-5739.
24. Schulze, H., Schmid, R. D., and Bachmann, T. T. (2004) *Anal. Chem.* 76, 1720-1725.
25. Sulistyaningdyah, W. T., Ogawa, J., Li, Q. S., Maeda, C., Yano, Y., Schmid, R. D., and Shimizu, S. (2005) *Appl. Microbiol. Biotechnol.* 67, 556-562.
26. Schwaneberg, U., Schmidt-Dannert, C., Schmitt, J., and Schmid, R. D. (1999) *Anal. Biochem.* 269, 359-366.
27. Li, Q. S., Schwaneberg, U., Fischer, M., Schmitt, J., Pleiss, J., Lutz-Wahl, S., and Schmid, R. D. (2001) *Biochim. Biophys. Acta* 1545, 114-121.
28. Farinas, E. T., Bulter, T., and Arnold, F. H. (2001) *Curr. Opin. Biotechnol.* 12, 545-551.
29. Glieder, A., Farinas, E. T., and Arnold, F. H. (2002) *Nat. Biotechnol.* 20, 1135-1139.
30. Meinhold, P., Peters, M. W., Chen, M. M., Takahashi, K., and Arnold, F. H. (2005) *Chem Bio Chem* 6, 1-4.
31. Peters, M. W., Meinhold, P., Glieder, A., and Arnold, F. H. (2003) *J. Am. Chem. Soc.* 125, 13442-13450.
32. Kubo, T., Peters, M. W., Meinhold, P., and Arnold, F. H. (2006) *Chemistry* 12, 1216-1220.
33. Munzer, D. F., Meinhold, P., Peters, M. W., Feichtenhofer, S., Griengl, H., Arnold, F. H., Glieder, A., and de Raadt, A. (2005) *Chem. Commun.*, 2597-2599.
34. Lentz, O., Feenstra, A., Habicher, T., Hauer, B., Schmid, R. D., and B., U. V. (2005) *Chem Bio Chem* 7, 345-350.
35. Ortiz de Montellano, P. R. (1986) *Cytochrome P450: Structure, Mechanism, and Biochemistry*, Plenum Press, New York.
36. Ortiz de Montellano, P. R. (ed) (1995) *Cytochrome P450: Structure, Mechanism, and Biochemistry*, 2$^{nd}$ Ed., Plenum Press, New York.
37. Ortiz de Montellano, P. R. (ed) (2005) *Cytochrome P450: Structure, Mechanism, and Biochemistry* 3rd Ed., Kluwer Academic/Plenum Press, New York.
38. Poulos, T. L., Finzel, B. C., and Howard, A. J. (1987) *J. Mol. Biol.* 195, 687-700.
39. Poulos, T. L. (2005) *Biochem. Biophys. Res. Commun.* 338, 337-345.
40. Poulos, T. L. (2005) *Drug Metab Dispos* 33, 10-18.
41. Poulos, T. L. (2003) *Proc. Natl. Acad. Sci. USA* 100, 13121-13122.
42. Poulos, T. L. (2003) *Biochem. Biophys. Res. Commun.* 312, 35-39.
43. Hasemann, C. A., Kurumbail, R. G., Boddupalli, S. S., Peterson, J. A., and Deisenhofer, J. (1995) *Structure* 2, 41-62.
44. Rupasinghe, S., Schuler, M. A., Kagawa, N., Yuan, H., Lei, L., Zhao, B., Kelly, S. L., Waterman, M. R., and Lamb, D. C. (2006) *FEBS Lett.* 580, 6338-6342.
45. Lepesheva, G. I., and Waterman, M. R. (2007) *Biochim. Biophys. Acta* 1770, 467-747.
46. Li, Q. S., Ogawa, J., Schmid, R. D., and Shimizu, S. (2001) *FEBS Lett.* 508, 249-252.
47. Capdevila, J. H., Wei, S., Helvig, C., Falck, J. R., Belosludtsev, Y., Truan, G., Graham-Lorence, S. E., and Peterson, J. A. (1996) *J. Biol. Chem.* 271, 22663-22671.
48. Sidles, G. L., and Yost, G. S. (1996) *Chem. Res. Toxicol.* 9, 291-297.
49. Lanza, D. L., and Yost, G. S. (2001) *Drug Metab Dispos* 29, 950-953.
50. Reilly, C. A., Ehlhardt, W. J., Jackson, D. A., Kulanthaivel, P., Mutlib, A. E., Espina, R. J., Moody, D. E., Crouch, D. J., and Yost, G. S. (2003) *Chem. Res. Toxicol.* 16, 336-349.
51. Kassahun, K., Skordos, K., McIntosh, I., Slaughter, D., Doss, G. A., Baillie, T. A., and Yost, G. S. (2005) *Chem. Res. Toxicol.* 18, 1427-1437.
52. Sun, H., Ehlhardt, W. J., Kulanthaivel, P., Lanza, D. L., Reilly, C. A., and Yost, G. S. (2007) *J Pharmacol Exp Ther* 322, 843-851.
53. Di Nardo, G., Fantuzzi, A., Sideri, A., Panicco, P., Sassone, C., Giunta, C., and Gilardi, G. (2007) *J Biol Inorg Chem* 12, 313-323.
54. Lentz, O., Feenstra, A., Habicher, T., Hauer, B., Schmid, R. D., and Urlacher, V. B. (2006) *Chem Bio Chem* 7, 345-350.
55. Cirino, P. C., and Arnold, F. H. (2003) *Angew. Chem. Int. Ed.* 42, 3299-3301.
56. Sevrioukova, I. F., Hazzard, J. T., Tollin, G., and Poulos, T. L. (1999) *J. Biol. Chem.* 274, 36097-36106.
57. Paulsen, M. D., and Ornstein, R. L. (1995) *Proteins: Struct., Funct., Genet.* 21, 237-243.
58. Honeychurch, M. J., Hill, H. A. O., and Wong, L. L. (1999) *FEBS Lett.* 451, 351-353.

TABLE A

Sequence similarities between CYP102A1 haem domain (amino acid residues 1-470) and various structurally characterized cytochrome P450 enzymes.

| Cytochrome P450 | CYP102A1 | | |
| --- | --- | --- | --- |
| | Identities | Positives | Gaps |
| CYP505 (P450foxy)* | 188/452 (41%) | 268/452 (59%) | 10/452 (2%) |
| CYP3A4 | 114/395 (28%) | 184/395 (45%) | 37/395 (9%) |
| CYP51 (*M. tuberculosis*) | 100/410 (24%) | 180/410 (43%) | 27/410 (6%) |
| P4502R1 | 76/252 (30%) | 126/252 (50%) | 19/252 (7%) |
| CYP175A1 | 98/364 (26%) | 150/364 (41%) | 61/364 (16%) |
| CYP2D6 | 59/232 (25%) | 96/232 (41%) | 24/232 (10%) |
| CYP2A6 | 99/434 (22%) | 174/434 (40%) | 26/434 (5%) |
| CYP108A1 (P450terp) | 58/219 (26%) | 97/219 (44%) | 30/219 (13%) |
| CYP2A13 | 99/437 (22%) | 170/437 (38%) | 26/437 (5%) |
| CYP2C8 | 57/198 (28%) | 85/198 (42%) | 7/198 (3%) |
| CYP107L1 (P450pikC) | 6/236 (27%) | 102/236 (43%) | 52/236 (22%) |
| CYP2B4 | 55/229 (24%) | 102/229 (44%) | 13/229 (5%) |
| CYP2C9 | 51/177 (28%) | 80/177 (45%) | 6/177 (3%) |
| CYP2C5 | 49/165 (29%) | 76/165 (46%) | 6/165 (3%) |
| CYP165B3 (P450oxyB) | 75/324 (23%) | 127/324 (39%) | 63/324 (19%) |
| CYP154C1 | 59/216 (27%) | 84/216 (38%) | 38/216 (17%) |
| CYP154A1 | 70/343 (20%) | 138/343 (40%) | 53/343 (15%) |
| CYP245A1 | 47/179 (26%) | 74/179 (41%) | 34/179 (18%) |
| CYP119A1 | 51/180 (28%) | 80/180 (44%) | 45/180 (25%) |
| CYP8A1 | 46/157 (29%) | 72/157 (45%) | 24/157 (15%) |
| CYP167A1 (P450epoK) | 51/219 (23%) | 94/219 (42%) | 38/219 (17%) |
| CYP107A1 (P450eryF) | 65/283 (22%) | 114/283 (40%) | 36/283 (12%) |
| CYP199A2 | 43/176 (24%) | 73/176 (41%) | 27/176 (15%) |
| CYP101A1 (P450cam) | 56/223 (25%) | 90/223 (40%) | 57/223 (25%) |
| CYP165C1 (P450oxyC) | 48/204 (23%) | 90/204 (44%) | 41/204 (20%) |
| CYP119A2 | 44/166 (26%) | 70/166 (42%) | 35/166 (21%) |

TABLE A-continued

Sequence similarities between CYP102A1 haem domain (amino acid residues 1-470) and various structurally characterized cytochrome P450 enzymes.

| Cytochrome P450 | CYP102A1 | | |
|---|---|---|---|
| | Identities | Positives | Gaps |
| CYP152A1 (P450BSβ) | 41/148 (27%) | 62/148 (41%) | 20/148 (13%) |
| CYP121 | 44/184 (23%) | 72/184 (39%) | 35/184 (19%) |

*CYP505 (P450foxy) is not structurally characterized and the alignment used the haem domain only.

TABLE B

Sequence similarities between CYP102A1 whole sequence and various cytochrome P450 enzymes (alignment done against proteins in the Swissprot protein databank).

| Cytochrome P450 | CYP102A1 | | |
|---|---|---|---|
| | Identities | Positives | Gaps |
| CYP102A2 | 627/1055 (59%) | 781/1055 (74%) | 12/1055 (1%) |
| CYP102A3 | 614/1050 (58%) | 785/1050 (74%) | 9/1050 (1%) |
| CYP505 | 395/1072 (36%) | 586/1072 (54%) | 43/1072 (4%) |

Note that, despite being in the same subfamily, CYP102A2 and CYP102A3 are only 59% and 58% homologous to CYP102A1.

TABLE C

Physical characteristics of amino acids

| NON-AROMATIC | Non-polar | G A P I L V |
|---|---|---|
| | Polar - uncharged | C S T M N Q |
| | Polar - charged | D E H K R |
| AROMATIC | | H F W Y |

TABLE D

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

TABLE 1

In vitro oxidation activity, coupling efficiency and selectivity of CYP102A1 variants with naphthalene.

| Variant | NADPH turnover rate | Coupling efficiency (%) | Product formation rate | % 1-ol |
|---|---|---|---|---|
| WT and accelerator variants | | | | |
| Wild-type | 80 | 3.9 | 3.1 | 100 |
| RLYF | 166 | 19 | 32 | 100 |
| KT2 | 490 | 23 | 113 | 100 |
| I401P (IP) (1) | 2816 | 42 | 1183 | 100 |
| I401P (IP) (2) | 2791 | 32 | 896 | 100 |
| Q403P | 484 | 25 | 121 | 100 |
| RLYF/IP | 4456 | 44 | 1939 | 100 |
| RLYF/KT2 | 1306 | 38 | 496 | 100 |
| F87A variants (KT5 also contains A330P) | | | | |
| F87A | 106 | 5.2 | 5.5 | 100 |
| F87A/KT2 | 370 | 8.7 | 32 | 100 |
| F87A/EP | 1865 | 12 | 220 | 100 |
| KSK19 | 511 | 11 | 56 | 100 |
| KT5 | 567 | 5.5 | 31 | 100 |
| F87V and F87L variants | | | | |
| GVQ | 2116 | 23 | 487 | 100 |
| F87L/KT2 | 723 | 28 | 202 | 100 |
| A330P variants | | | | |
| A330P | 483 | 32 | 155 | 100 |
| RLYF/A330P(1) | 1306 | 51 | 666 | 100 |
| RLYF/A330P(2) | 1333 | 51 | 680 | 100 |
| RLYF/A330P/IP | 1728 | 39 | 666 | 100 |

Rates are given in nmol·min$^{-1}$·(nmol P450)$^{-1}$. The only detectable product was 1-naphthol (1-ol).

TABLE 2

In vitro oxidation activity, selectivity and spin shifts of CYP102A1 variants with propylbenzene.

| Variant | NADPH turnover rate | Coupling efficiency (%) | Product formation rate | % 1-ol | % 2-ol | % ortho | % para |
|---|---|---|---|---|---|---|---|
| WT and accelerator variants | | | | | | | |
| Wild-type (1) | 866 | 70 | 606 | 99 | — | 1 | — |
| Wild-type (2) | 894 | 71 | 635 | 99 | — | 1 | — |
| R47L/Y51F | 2157 | 78 | 1682 | 99 | 1 | — | — |
| KT2 | 2756 | 80 | 2205 | 99 | — | 1 | — |
| I401P (1) | 4953 | 78 | 3863 | 98 | 1 | 1 | — |
| I401P (2) (*) | 4476 | 80 | 3578 | 98 | 0.5 | 0.5 | — |
| RLYF/IP (*) | 5550 | 91 | 5074 | 98.5 | 0.5 | 0.5 | |

TABLE 2-continued

In vitro oxidation activity, selectivity and spin shifts of CYP102A1 variants with propylbenzene.

| Variant | NADPH turnover rate | Coupling efficiency (%) | Product formation rate | % 1-ol | % 2-ol | % ortho | % para |
|---|---|---|---|---|---|---|---|
| RLYF/KT2 | 3126 | 86 | 2688 | 100 | — | — | — |
| F87A variants (KT5 also contains A330P) | | | | | | | |
| F87A | 670 | 36 | 241 | 47 | 53 | — | — |
| F87A/KT2 | 1664 | 34 | 566 | 54 | 46 | — | — |
| F87A/IP (*) | 2176 | 41 | 897 | 61 | 38.5 | — | — |
| KSK19 | 2079 | 51 | 1060 | 53 | 47 | — | — |
| KT5 (*) | 1062 | 65 | 690 | 20 | 79 | — | — |
| F87V and F87L variant | | | | | | | |
| GVQ | 3172 | 32 | 1015 | 78 | 14 | 8 | — |
| F87L/KT2 (*) | 462 | 34 | 157 | 49 | 2 | 45 | 1 |
| A330P variants | | | | | | | |
| A330P | 1810 | 39 | 706 | 68 | 2 | 30 | — |
| RLYF/A330P (1) | 2497 | 27 | 674 | 65 | 5 | 23 | 7 |
| RLYF/A330P (2) | 2524 | 27 | 681 | 65 | 5 | 23 | 7 |
| RLYF/A330P/IP (*) | 2592 | 28 | 721 | 75.5 | 2 | 20 | 1.5 |

Rates are given in nmol · min$^{-1}$ · (nmol P450)$^{-1}$.

Products were 1-phenyl-1-propanol (1-ol), 1-phenyl-2-propanol (2-ol), 2-propylphenol (ortho) and 4-propylphenol (para). Small quantities of 1-phenyl-1-propanone (≤1%) and 3-phenyl-1-propanol (<0.5%, KT5 only) were also formed.

— Not detected.

(*) Percentages do not sum to 100 due to these and other minority products.

TABLE 3

In vitro oxidation activity and selectivity of CYP102A1 variants with toluene.

| Variant | NADPH turnover rate | Coupling efficiency (%) | Product formation rate | % 1-ol | % ortho | % para | % others |
|---|---|---|---|---|---|---|---|
| WT and accelerator variants | | | | | | | |
| Wild-type (1) | 29 | 9.4 | 2.7 | 2 | 98 | — | — |
| Wild-type (2) | 57 | 3.9 | 2.2 | 2.5 | 96.5 | 1 | — |
| RLYF | 57 | 13 | 7.4 | 1 | 98 | 1 | — |
| KT2 | 156 | 23 | 36 | 3 | 96 | 1 | — |
| I401P (1) | 1248 | 25 | 312 | 3 | 96 | — | 1 |
| I401P (2) | 1326 | 14 | 180 | — | 100 | — | — |
| Q403P | 126 | 10 | 13 | — | 100 | — | — |
| RLYF/IP | 2539 | 16 | 415 | — | 99 | — | 1 |
| RLYF/KT2 | 368 | 37 | 136 | 3 | 95 | 2 | — |
| F87A variants (KT5 also contains A330P) | | | | | | | |
| F87A | 11 | 0.8 | 0.1 | 22 | 78 | — | — |
| F87A/KT2 | 131 | 1.4 | 1.8 | 49 | 51 | — | — |
| KSK19 | 115 | 2.1 | 2.4 | 43 | 57 | — | — |
| KT5 | 217 | 2.9 | 6.3 | 95 | 5 | — | — |
| F87V and F87L variants | | | | | | | |
| GVQ | 1202 | 6.2 | 75 | 39 | 58 | 2 | 1 |
| F87L/KT2 | 58 | 6.0 | 3.5 | 33 | 64 | — | 3 |
| A330P variants | | | | | | | |
| A330P | 189 | 45 | 85 | 1 | 98 | 1 | — |
| RLYF/A330P | 363 | 52 | 189 | 1 | 97 | 1 | 1 |
| RLYF/A330P/IP | 3732 | 49 | 1824 | — | 100 | — | — |

Rates are given in nmol · min$^{-1}$ · (nmol P450)$^{-1}$.
Products were benzylalcohol (1-ol), o-cresol (ortho) and p-cresol (para).
— Not detected.

TABLE 4

In vitro oxidation activity and selectivity of CYP102A1 variants with butylbenzene.

| Variant | NADPH turnover rate | Coupling efficiency (%) | Product formation rate | % 1-ol (*) | % 2-ol | % 3-ol | % ortho | % para | % others |
|---|---|---|---|---|---|---|---|---|---|
| WT and accelerator variants ||||||||||
| Wild-type | 457 | 64 | 292 | 80 | 10 | 8 | 2 | — | — |
| RLYF | 996 | 69 | 687 | 80 | 10 | 9 | 1 | — | — |
| KT2 | 2124 | 68 | 1444 | 80 | 10 | 8 | 2 | — | — |
| RLYF/KT2 | 2299 | 73 | 1678 | 80 | 11 | 8 | 1 | — | — |
| F87A variants (KT5 also contains A330P) ||||||||||
| F87A | 795 | 49 | 390 | 43 | 46 | 10 | — | — | 1 |
| F87A/KT2 | 1357 | 43 | 584 | 49 | 42 | 9 | — | — | — |
| KSK19 | 1729 | 51 | 882 | 48 | 41 | 10 | — | — | 1 |
| KT5 | 1277 | 53 | 677 | 18 | 45 | 35 | — | — | 2 |
| F87V and F87L variants ||||||||||
| GVQ | 3166 | 38 | 1203 | 49 | 28 | 15 | 7 | — | 1 |
| F87L/KT2 | 420 | 16 | 67 | 41 | 10 | 5 | 32 | 1 | 11 |
| A330P variants ||||||||||
| A330P | 1617 | 25 | 404 | 14 | 37 | 19 | 10 | 20 | — |
| RLYF/A330P | 2094 | 22 | 461 | 11 | 29 | 26 | 6 | 26 | 2 |

Rates are given in nmol · min$^{-1}$ · (nmol P450)$^{-1}$.
Products were 1-phenyl-1-butanol (1-ol), 1-phenyl-2-butanol (2-ol), 4-phenyl-2-butanol (3-ol), 2-butylphenol (ortho) and 4-butylphenol (para).
(*) includes 1-3% 1-phenyl-1-butanone.
— Not detected.

TABLE 5a

In vitro oxidation activity, selectivity and spin shifts of CYP102A1 variants with t-butylbenzene.

| Variant | NADPH turnover rate | Coupling efficiency (%) | Product formation rate | % ortho | % para | % 1-ol |
|---|---|---|---|---|---|---|
| WT and accelerator variants |||||||
| Wild-type | 304 | 0.8 | 2.4 | 14 | 63 | 23 |
| R47L/Y51F | 963 | 0.6 | 5.8 | 7 | 61 | 34 |
| KT2 | 1429 | 1.0 | 14 | 10 | 70 | 20 |
| RLYF/KT2 | 2808 | 0.4 | 11 | — | 41 | 59 |
| F87A variants (KT5 also contains A330P) |||||||
| F87A | 329 | 11 | 36 | — | — | 100 |
| F87A/KT2 | 1946 | 12 | 234 | — | — | 100 |
| KSK19 | 1548 | 13 | 201 | — | — | 100 |
| KT5 | 1297 | 16 | 208 | — | — | 100 |
| F87V and F87L variants |||||||
| GVQ | 2753 | 4.3 | 118 | — | — | 100 |
| F87L/KT2 | 307 | 1.9 | 5.8 | 29 | 61 | 10 |
| A330P variant |||||||
| A330P | 1421 | 1.8 | 26 | 8 | 82 | 10 |
| RLYF/A330P | 1983 | 3.7 | 73 | 2 | 92 | 6 |

Rates are given in nmol · min$^{-1}$ · (nmol P450)$^{-1}$.
Products were 2-t-butylphenol (ortho), 4-t-butylphenol (para) and 2-methyl-2-phenyl-propan-1-ol (1-ol).
— Not detected.

TABLE 5b

In vitro oxidation activity/selectivity and spin shifts of CYP102A1 variants with ethylbenzene.

| Variant | NADPH turnover rate | Coupling efficiency (%) | Product formation rate | % 1-ol | % 2-ol | % ortho | % styrene |
|---|---|---|---|---|---|---|---|
| WT and accelerator variants | | | | | | | |
| Wild-type (1) | 123 | 49 | 60 | 90 | — | 10 | — |
| Wild-type (2) | 123 | 28 | 34 | 90 | | 10 | |
| R47L/Y51F | 433 | 51 | 221 | 95 | — | 5 | — |
| KT2 | 806 | 53 | 427 | 91 | — | 9 | — |
| RLYF/KT2 | 1861 | 59 | 1098 | 93 | — | 7 | — |
| F87A variants (KT5 also contains A330P) | | | | | | | |
| F87A | 138 | 22 | 30 | 100 | — | — | — |
| F87A/KT2 | 570 | 20 | 114 | 100 | — | — | — |
| KSK19 | 710 | 24 | 170 | 100 | — | — | — |
| KT5 | 488 | 31 | 151 | 93 | 4 | — | 3 |
| F87V and F87L variants | | | | | | | |
| GVQ | 2201 | 26 | 572 | 100 | — | — | — |
| F87L/KT2 | 169 | 19 | 32 | 79 | — | 21 | — |
| A330P variants | | | | | | | |
| A330P | 720 | 55 | 396 | 73 | — | 27 | — |
| RLYF/A330P | 1713 | 62 | 1062 | 74 | — | 26 | — |

Rates are given in nmol · min$^{-1}$ · (nmol P450)$^{-1}$.
Products were 1-phenylethanol (1-ol), 2-phenylethanol (2-ol), 2-ethylphenol (ortho) and styrene.
— Not detected.
NB/Results were also obtained for F87A, F87A/KT2, KSK19 and GVQ following recalibration of detector response. NADPH turnover was identical. Coupling efficiencies were 23 (F87A), 21 (F87A/KT2), 25 (KSK19), 26 (GVQ). Product formation rates were 32 (F87A), 120 (F87A/KT2), 178 (KSK19), 572 (GVQ). 1-ol was 99% (F87A), 96% (F87A/KT2), 95% (KSK19), 99% (GVQ). Styrene was now detected in reactions with these variants at 2% (F87A), 4% (F87A/KT2), 5% (KSK19), 1% (GVQ).

TABLE 6a

In vitro oxidation activity and selectivity of CYP102 variants with o-xylene.

| Variant | NADPH turnover rate | Coupling efficiency (%) | Product formation rate | % 1-ol | % 2,3 phenol | % 3,4 phenol | % hydroquinone | % catechol |
|---|---|---|---|---|---|---|---|---|
| WT and accelerator variants | | | | | | | | |
| Wild-type | 32 | 14 | 4.5 | 47 | 27 | 10 | 8 | 8 |
| R47L/Y51F | 77 | 36 | 28 | 49 | 24 | 10 | 9 | 8 |
| KT2 | 291 | 43 | 125 | 57 | 22 | 8 | 7 | 6 |
| RLYF/KT2 | 584 | 61 | 356 | 57 | 20 | 9 | 8 | 6 |
| F87A variants (KT5 also contains A330P) | | | | | | | | |
| F87A | 133 | 11 | 15 | 94 | 1 | — | 2 | 3 |
| F87A/KT2 | 197 | 14 | 28 | 92 | 1 | — | 2 | 5 |
| KSK19 | 133 | 20 | 27 | 93 | 2 | 1 | 2 | 2 |
| KT5 (*) | 237 | 36 | 85 | 99 | — | — | — | — |
| F87V and F87L variants | | | | | | | | |
| GVQ (*) | 1520 | 29 | 441 | 84 | 6 | 2 | 4 | 3 |
| F87L/KT2 (*) | 134 | 23 | 31 | 79 | 10 | 3 | 3 | 3 |
| A330P variants | | | | | | | | |
| A330P | 307 | 49 | 150 | 28 | 29 | 14 | 16 | 13 |
| RLYF/A330P | 694 | 79 | 548 | 29 | 28 | 15 | 15 | 13 |

Rates are given in nmol · min$^{-1}$ · (nmol P450)$^{-1}$.
Products were 2-methylbenzylalcohol (1-ol), 2,3-dimethylphenol (2,3-phenol), 3,4-dimethylphenol (3,4-phenol), 2,3-dimethyl-p-benzoquinone (hydroquinone) and pyrocatechol (catechol).
(*) Percentages do not sum to 100 due to minority products.
— Not detected.

TABLE 6b

In vitro oxidation activity and selectivity of CYP102A1 variants with m-xylene.

| Variant | NADPH turnover rate | Coupling efficiency (%) | Product formation rate | % 1-ol | % 2,4 phenol | % 2,6 phenol |
|---|---|---|---|---|---|---|
| WT and accelerator variants | | | | | | |
| Wild-type | 27 | 29 | 7.8 | 2 | 87 | 11 |
| R47L/Y51F | 143 | 38 | 54 | 2 | 90 | 8 |
| KT2 | 545 | 40 | 218 | 4 | 86 | 10 |
| RLYF/KT2 (*) | 1152 | 50 | 576 | 3 | 87 | 8 |
| F87A variants (KT5 also contains A330P) | | | | | | |
| F87A | 90 | 13 | 12 | 45 | 54 | 1 |
| F87A/KT2 | 253 | 10 | 25 | 49 | 50 | 1 |
| KSK19 | 367 | 12 | 44 | 47 | 51 | 2 |
| KT5 | 369 | 15 | 55 | 83 | 16 | 1 |
| F87V and F87L variants | | | | | | |
| GVQ | 1611 | 15 | 242 | 23 | 71 | 6 |
| F87L/KT2 | 192 | 14 | 27 | 23 | 67 | 10 |
| A330P variants | | | | | | |
| A330P | 429 | 48 | 206 | 1 | 85 | 14 |
| RLYF/A330P | 1282 | 64 | 820 | 1 | 87 | 12 |

Rates are given in nmol·min$^{-1}$·(nmol P450)$^{-1}$.
Products were 3-methylbenzylalcohol (1-ol), 2,4-dimethylphenol (2,4-phenol) and 2,6-dimethylphenol (2,6-phenol).
(*) Percentages do not sum to 100 due to minority products.

TABLE 7

In vitro oxidation activity/selectivity and spin shifts of CYP102A1 variants with p-cymene.

| Variant | NADPH turnover rate | Coupling efficiency (%) | Product formation rate | % p-α-DMS(*) | % i-Pr-ol | % Me-ol | % thymol | % carvacrol | % other |
|---|---|---|---|---|---|---|---|---|---|
| WT and accelerator variants | | | | | | | | | |
| Wild-type | 467 | 36 | 168 | 6 | 82 | 2 | 3 | 7 | — |
| R47L/Y51F | 1648 | 41 | 676 | 4 | 88 | 1 | 2 | 5 | — |
| KT2 | 1867 | 44 | 821 | 5 | 80 | 3 | 4 | 8 | — |
| RLYF/KT2 | 2919 | 48 | 1401 | 7* | 77 | 4 | 5 | 6 | 1 |
| F87A variants (KT5 also contains A330P) | | | | | | | | | |
| F87A | 413 | 38 | 157 | 8* | 92 | — | — | — | — |
| F87A/KT2 | 2234 | 51 | 1139 | 20* | 78 | 2 | — | — | — |
| KSK19 | 2721 | 53 | 1442 | 23* | 76 | 1 | — | — | — |
| KT5 | 1403 | 50 | 702 | 22* | 76 | 2 | — | — | — |
| F87V and F87L variants | | | | | | | | | |
| GVQ (**) | 2799 | 28 | 784 | 27* | 71 | 1 | — | — | — |
| F87L/KT2 | 475 | 16 | 76 | — | 5 | 74 | — | 21 | — |
| A330P variants | | | | | | | | | |
| A330P | 1040 | 26 | 270 | 4* | 35 | 19 | 19 | 16 | 7 |
| RLYF/A330P | 1825 | 26 | 475 | 7* | 42 | 28 | 12 | 8 | 3 |

Rates are given in nmol·min$^{-1}$·(nmol P450)$^{-1}$.
Products were p-α-dimethylstyrene (p-α-DMS), p-α-α-trimethylbenzylalcohol (i-Pr-ol), 4-isopropylbenzylalcohol (Me-ol), thymol, carvacrol and an unidentified product.
(*) includes up to 3% p-α-dimethylstyreneoxide.
(**) Percentages do not sum to 100 due to other minority products.
— Not detected.

TABLE 8

In vitro oxidation activity and selectivity of some CYP102A1 variants with cumene.

| Variant | NADPH turnover rate | Coupling efficiency (%) | Product formation rate | styrene | styrene oxide | 1-ol | 2-ol | ortho | para |
|---|---|---|---|---|---|---|---|---|---|
| Wildtype | 419 | 31 | 130 | 2 | — | — | 83 | 14 | 1 |
| A330P | 1687 | 32 | 540 | 9 | 2 | 1 | 71 | 15 | 2 |
| Q403P | 1621 | 38 | 616 | 12.5 | — | — | 83 | 4.5 | — |
| KSK19 | 1755 | 37 | 649 | 23 | 6 | 1 | 70 | — | — |
| KT5 | 755 | 39 | 294 | 31 | 4 | 3 | 62 | — | — |

Rates are given in nmol · min$^{-1}$ · (nmol P450)$^{-1}$.
Products were α-methylstyrene (styrene), α-methylstyrene oxide (styrene oxide), 2-phenyl-1-propanol (1-ol), 2-phenyl-2-propanol (2-ol), 2-isopropylphenol (ortho) and 4-isopropylphenol (para).
— Not detected.

TABLE 8a

In vitro oxidation activity and selectivity of some CYP102A1 variants with cumene after further GC analysis.

| Variant | NADPH turnover rate | Coupling efficiency (%) | Product formation rate | styrene | styrene oxide | 1-ol | 2-ol | ortho | para |
|---|---|---|---|---|---|---|---|---|---|
| Wildtype | 419 | 31 | 130 | 8.5 | — | — | 81 | 10.5 | — |
| A330P | 1687 | 31 | 523 | 7 | — | 1 | 75 | 15 | 2 |
| Q403P | 1621 | 38 | 616 | 12.5 | — | — | 83 | 4.5 | — |
| KSK19 | 1755 | 34 | 597 | 19 | 1 | 1 | 79 | — | — |
| KT5 | 755 | 37 | 279 | 27 | 1 | 3 | 69 | — | — |

Rates are given in nmol · min$^{-1}$ · (nmol P450)$^{-1}$.
Products were α-methylstyrene (styrene), α-methylstyrene oxide (styrene oxide), 2-phenyl-1-propanol (1-ol), 2-phenyl-2-propanol (2-ol), 2-isopropylphenol (ortho) and 4-isopropylphenol (para).
— Not detected.

TABLE 9

In vitro oxidation activity, selectivity and spin shifts of CYP102A1 variants with pentane.

| Variant | NADPH turnover rate | Coupling efficiency (%) | Product formation rate | % 2-ol | % 3-ol | % 2-one | % 3-one |
|---|---|---|---|---|---|---|---|
| WT and accelerator variants ||||||||
| Wild-type | 74 | 21 | 16 | 59 | 39 | — | 2 |
| R47L/Y51F | 361 | 45 | 162 | 58 | 42 | — | — |
| KT2 | 1103 | 56 | 618 | 59 | 41 | — | — |
| I401P | 2325 | 42 | 977 | 57 | 38 | 2 | 3 |
| RLYF/KT2 | 2010 | 60 | 1206 | 63 | 37 | — | — |
| F87A variants ||||||||
| F87A | 155 | 18 | 28 | 62 | 38 | — | — |
| F87A/KT2 | 538 | 22 | 118 | 57 | 43 | — | — |
| KSK19 | 738 | 27 | 199 | 56 | 41 | 1 | 2 |
| KT5 | 502 | 19 | 95 | 65 | 35 | — | — |
| F87V variant ||||||||
| GVQ | 2107 | 28 | 590 | 47 | 52 | — | 1 |
| A330P variants ||||||||
| A330P | 959 | 65 | 623 | 62 | 38 | — | — |
| RLYF/A330P | 1766 | 67 | 1183 | 63 | 37 | — | — |

Rates are given in nmol · min$^{-1}$ · (nmol P450)$^{-1}$.
Products were 2-pentanol (2-ol), 3-pentanol (3-ol), 2-pentanone (2-one) and 3-pentanone (3-one).

TABLE 10

In vitro oxidation activity/selectivity and spin shifts of CYP102A1 variants with 3-methylpentane.

| Variant | NADPH turnover rate | Coupling efficiency (%) | Product formation rate | % 2-ol (A) | % 2-ol (B) | % 3-ol |
|---|---|---|---|---|---|---|
| WT and accelerator variants |||||||
| Wild-type | 98 | 41 | 40 | 69 | 19 | 13 |
| R47L/Y51F | 568 | 58 | 329 | 65 | 22 | 13 |
| KT2 | 1005 | 57 | 573 | 67 | 20 | 13 |
| I401P (IP) (1) | 2566 | 46 | 1180 | 66 | 19 | 15 |
| I401P (IP) (2) | 2763 | 50 | 1378 | 63 | 22 | 15 |
| Q403P | 685 | 52 | 356 | 65 | 19 | 16 |
| RLYF/IP | 4925 | 61 | 2980 | 58 | 26.5 | 15.5 |
| RLYF/KT2 | 1713 | 60 | 1028 | 64 | 23 | 13 |
| F87A variants (KT5 also contains A330P) |||||||
| F87A | 184 | 27 | 50 | 15 | 9 | 76 |
| F87A/KT2 | 530 | 37 | 196 | 14 | 9 | 77 |
| F87A/IP | 1569 | 36 | 565 | 15.5 | 11.5 | 73 |
| KSK19 | 469 | 40 | 188 | 13 | 9 | 78 |
| KT5 | 570 | 42 | 239 | 10 | 7 | 83 |
| F87V variant |||||||
| GVQ | 1856 | 32 | 594 | 36 | 17 | 47 |
| A330P variants |||||||
| A330P | 982 | 64 | 628 | 59 | 23 | 18 |
| RLYF/A330P | 1986 | 67 | 1331 | 54 | 27 | 19 |
| RLYF/A330P/IP | 2277 | 68 | 1553 | 41.5 | 33 | 25.5 |

Rates are given in nmol · min$^{-1}$ · (nmol P450)$^{-1}$.
Products were 3-methyl-2-pentanol (2-ol) - two diastereomers designated (A) and (B), and 3-methyl-3-pentanol (3-ol).

TABLE 11

In vitro oxidation activity and selectivity of CYP102A1 variants with 2-methylbutane.

| Variant | NADPH turnover rate | Coupling efficiency (%) | Product formation rate | % 1-ol | % 2-ol | % 3-ol | % 4-ol | % 3-one |
|---|---|---|---|---|---|---|---|---|
| WT and accelerator variants ||||||||| 
| Wild-type | 118 | 43 | 51 | 2 | 21 | 77 | — | — |
| R47L/Y51F | 449 | 48 | 216 | 1 | 21 | 78 | — | — |
| KT2 | 902 | 53 | 478 | 2 | 21 | 77 | — | — |
| I401P | 2120 | 34 | 721 | 1 | 20 | 79 | — | — |
| RLYF/KT2 | 1782 | 62 | 1105 | 2 | 22 | 76 | — | — |
| F87A variants (KT5 also contains A330P) |||||||||
| F87A/KT2 | 712 | 24 | 171 | 1 | 82 | 17 | — | — |
| KT5 | 453 | 28 | 127 | 1 | 83 | 15 | — | 1 |
| F87V and F87L variants |||||||||
| GVQ | 1682 | 27 | 454 | 2 | 52 | 45 | 1 | — |
| F87L/KT2 | 88 | 6 | 5 | 5 | 24 | 71 | — | — |
| A330P variant |||||||||
| RLYF/A330P | 2151 | 69 | 1484 | 2 | 31 | 67 | — | — |

Rates are given in nmol · min$^{-1}$ · (nmol P450)$^{-1}$.
Products were 2-methyl-1-butanol (1-ol), 2-methyl-2-butanol (2-ol), 3-methyl-2-butanol (3-ol), 3-methyl-1-butanol (4-ol) and 3-methyl-2-butanone (3-one).
— Not detected.

TABLE 12

In vitro oxidation activity and selectivity of some CYP102A1 variants with butane and propane.

| Variant | NADPH turnover rate | Coupling efficiency (%) | Product formation rate | % 1-ol | % 2-ol | % 2-one |
|---|---|---|---|---|---|---|
| Butane |||||||
| Wild-type | 55 | 19 | 10 | — | 99 | 1 |
| GVQ | 1377 | 15 | 207 | — | 98 | 2 |
| RLYF/KT2 | 1123 | 52 | 584 | — | 97 | 3 |
| RLYF/A330P | 764 | 62 | 474 | 1 | 92 | 7 |
| Propane |||||||
| Wild-type (1) | 1 | 0.1 | 0.001 | — | 100 | — |
| Wild-type (2) | 27 | 0.7 | 0.2 | 73 | 27 | — |
| GVQ | 404 | 0.7 | 2.8 | — | 100 | — |
| RLYF/KT2 | 90 | 6.4 | 5.8 | — | 100 | — |
| RLYF/A330P | 180 | 21 | 38 | — | 100 | — |
| (1) RLYF/A330P | 220 | 21 | 46 | — | 100 | — |
| (2) I401P (IP) | 684 | 3.7 | 25 | — | 100 | — |
| F87A/IP | 727 | 1.3 | 9.6 | — | 100 | — |
| RLYF/IP | 1245 | 8.5 | 106 | — | 100 | — |
| RLYF/A330P/IP | 1264 | 29 | 430 | 4.5 | 95.5 | — |

Rates are given in nmol · min$^{-1}$ · (nmol P450)$^{-1}$.
Products were 1-butanol (1-ol), 2-butanol (2-ol) and 2-butanone (2-one) for butane and 2-propanol only for propane.

TABLE 13

In vitro oxidation activity and selectivity of CYP102A1 variants with octane.

| Variant | NADPH turnover rate | Coupling efficiency (%) | Product formation rate | % 2-ol | % 3-ol | % 4-ol | % 3-one | % 4-one |
|---|---|---|---|---|---|---|---|---|
| WT and accelerator variants |||||||||
| Wild-type | 148 | 36 | 53 | 15 | 43 | 42 | — | — |
| RLYF/KT2 | 770 | 32 | 246 | 16 | 40 | 43 | — | 1 |
| I401P | 2215 | 32 | 709 | 14 | 44 | 42 | — | — |
| Q403P | 471 | 22 | 104 | 8 | 46 | 46 | — | — |
| F87A variants (KT5 also contains A330P) |||||||||
| F87A | 181 | 28 | 51 | 10 | 38 | 43 | 7 | 2 |
| F87A/KT2 | 628 | 27 | 170 | 11 | 37 | 43 | 7 | 2 |
| KT5 | 519 | 17 | 83 | 12 | 35 | 25 | 24 | 4 |

TABLE 13-continued

In vitro oxidation activity and selectivity of CYP102A1 variants with octane.

| Variant | NADPH turnover rate | Coupling efficiency (%) | Product formation rate | % 2-ol | % 3-ol | % 4-ol | % 3-one | % 4-one |
|---|---|---|---|---|---|---|---|---|
| A330P variants | | | | | | | | |
| A330P | 642 | 26 | 167 | 53 | 30 | 16 | 1 | — |
| RLYF/A330P | 1046 | 22 | 230 | 56 | 25 | 17 | 2 | — |

Rates are given in nmol · min⁻¹ · (nmol P450)⁻¹.
Products were 2-octanol (2-ol), 3-octanol (3-ol), 4-octanol (4-ol), 3-octanone (3-one) and 4-octanone (4-one).
— Not detected.

TABLE 14

In vitro oxidation activity and selectivity of some CYP102A1 variants with 1,4-dichlorobenzene.

| Variant | NADPH turnover rate | Coupling efficiency (%) | Product formation rate | % product |
|---|---|---|---|---|
| WT and accelerator variants | | | | |
| Wild-type | 544 | 10 | 54 | 100 |
| RLYF | 1161 | 16 | 186 | 100 |
| KT2 | 1685 | 8 | 135 | 100 |
| RLYF/KT2 | 2603 | 7 | 182 | 100 |
| F87A variants | | | | |
| F87A | 655 | — | — | — |
| F87A/KT2 | 1921 | — | — | — |
| KSK19 | 2549 | — | — | — |
| F87V variant | | | | |
| GVQ | 1988 | — | — | — |
| A330P variants | | | | |
| A330P | 1126 | 15 | 169 | 100 |
| RLYF/A330P | 2039 | 12 | 245 | 100 |

Rates are given in nmol · mm⁻¹ · (nmol P450)⁻¹. Products were 2,4-dichlorophenol and/or 2,5-dichlorophenol, which have identical GC elution times. Further oxidation to a GC-indetectible semiquinone may make the coupling figures unreliable.

TABLE 15

In vitro oxidation activity and selectivity of CYP102A1 variants with valencene.

| Variant | NADPH turnover rate | Coupling efficiency (%) | Product formation rate | % Nootkatols | % Nootkatone | % Val. epox. | % Noot. epox. | % others |
|---|---|---|---|---|---|---|---|---|
| WT and accelerator variants | | | | | | | | |
| Wild-type | 42 | 16 | 6.7 | 21 | — | 34 | 6 | 39 |
| R47L/Y51F | 194 | 21 | 41 | 11 | 1 | 50 | 2 | 36 |
| Q403P | 277 | 14 | 39 | 25 | — | 52 | 1 | 22 |
| KT2 | 339 | 17 | 58 | 7 | 1 | 54 | 9 | 29 |
| RLYF/KT2 | 519 | 22 | 114 | 7 | — | 66 | 3 | 24 |
| F87A variants (KT5 also contains A330P) | | | | | | | | |
| F87A | 443 | 24 | 106 | 36 | 23 | 21 | 5 | 15 |
| F87A/KT2 | 671 | 24 | 161 | 24 | 32 | 20 | 11 | 13 |
| KSK19 | 1050 | 21 | 221 | 24 | 25 | 23 | 11 | 17 |
| KT5 | 557 | 23 | 128 | 18 | 30 | 30 | 14 | 8 |
| F87V variant | | | | | | | | |
| GVQ | 540 | 17 | 92 | 29 | 11 | 36 | 8 | 16 |
| A330P variant | | | | | | | | |
| A330P | 14 | 5.0 | 0.7 | 39 | 4 | — | 16 | 41 |
| RLYF/A330P | 61 | 11 | 6.7 | 43 | — | 10 | 2 | 45 |

Rates are given in nmol · min⁻¹ · (nmol P450)⁻¹.
Products were cis- and trans-nootkatols (nootkatols), nootkatone, cis- and trans-valencene epoxides (Val. epox.) and cis- and trans-nootkatone epoxides (Noot. epox.).

TABLE 16

In vitro oxidation activity and selectivity of some CYP102A1 variants with R- and S-limonene.

| Variant | NADPH turnover rate | Coupling efficiency (%) | Product formation rate | epoxides | 4.07 min | Isopiper | carveols | others |
|---|---|---|---|---|---|---|---|---|
| | | | R-limonene | | | | | |
| Wild-type | 463 | 43 | 199 | 27 | — | 15 | 55 | 3 |
| F87A/KT2 | 1249 | 42 | 525 | 9 | 7 | 66 | 2 | 16 |
| RLYF/A330P | 1596 | 49 | 782 | 33 | — | 48 | 5 | 14 |
| RLYF/KT2 | 1986 | 54 | 1072 | 28 | — | 19 | 49 | 4 |
| | | | S-limonene | | | | | |
| Wild-type | 361 | 40 | 144 | 43 | 1 | 31 | 21 | 4 |
| F87A/KT2 | 1105 | 45 | 497 | 26 | 17 | 41 | 3 | 13 |

Rates are given in nmol · min$^{-1}$ · (nmol P450)$^{-1}$.

Products were 1,2-limonene epoxides (epoxides), cis- and trans-isopiperitenol (isopiper), and cis- and trans-carveols (carveols).

TABLE 16a

In vitro oxidation activity and selectivity of CYP102A1 variants with R-limonene.

| Variant | N | C (%) | PFR | % cis-1,2 | % tr-1,2 | % U | % cis-3-ol | % tr-3-ol | % 6-ol (A) | % 6-ol (B) | % 6-one | % 10-ol | % other |
|---|---|---|---|---|---|---|---|---|---|---|---|---|---|
| Wild-type (WT) | 491 | 40 | 196 | 16.5 | 4.5 | 0.5 | 5.5 | 10.5 | 49 | 9.5 | 0.5 | 1 | 2.5 |
| F87A/KT2 | 1249 | 42 | 545 | 4 | 3 | 5.5 | 10 | 58 | 2 | 0.5 | — | 4 | 13 |
| Q403P | 2053 | 77 | 1581 | 20 | 4.5 | 0.5 | 5 | 11 | 40 | 10.5 | 4 | 0.5 | 4 |
| I401P (IP) | 3490 | 69 | 2403 | 18.5 | 4.5 | 0.5 | 4 | 13 | 42 | 10.5 | 2.5 | 1.5 | 3 |
| F87A/IP | 1195 | 56 | 666 | 10 | 6.5 | 5.5 | 6.5 | 45.5 | 3 | 2 | 4.5 | 6.5 | 10 |
| RLYF/IP | 4479 | 70 | 3123 | 20 | 4.5 | 0.5 | 4 | 11.5 | 42 | 10.5 | 2.5 | 1.5 | 3 |
| RLYF/A330P/IP | 1345 | 61 | 825 | 22.5 | 11 | 0.5 | 6 | 33.5 | 6 | 3 | 3.5 | 5 | 9 |
| RLYF/A330P | 1623 | 48 | 779 | 18.5 | 12.5 | — | 10 | 39 | 3 | 2.5 | — | 6 | 8.5 |

N = NADPH turnover rate.
C = coupling.
PFR = product formation rate.
Rates in nmol min$^{-1}$ (nmol P450)$^{-1}$.

Products were cis-1,2-limonene epoxide (cis-1,2), trans-1,2-limonene epoxide (tr-1,2), unidentified product (U), cis-isopiperitenol (cis-3-ol), trans-isopiperitenol (tr-3-ol), carveol (2 isomers) (6-ol (A) and (B)), carvone (6-one) and perillyl alcohol (10-ol).

TABLE 17

In vitro oxidation activity and selectivity of some CYP102A1 variants with (+)-α-pinene.

| Variant | NADPH turnover rate | Coupling efficiency (%) | Product formation rate | Epoxides | Verbenols | Verbenones | Myrtenol | others |
|---|---|---|---|---|---|---|---|---|
| Wild-type | <1 | ~16 | <0.2 | 31 | 44 | 7 | 5 | 13 |

TABLE 17-continued

In vitro oxidation activity and selectivity of some CYP102A1 variants with (+)-α-pinene.

| Variant | NADPH turnover rate | Coupling efficiency (%) | Product formation rate | Epoxides | Verbenols | Verbenones | Myrtenol | others |
|---|---|---|---|---|---|---|---|---|
| F87A/KT2 | 469 | 44 | 206 | 14 | 64 | 7 | 4 | 11 |

Rates are given in nmol · min⁻¹ · (nmol P450)⁻¹.
Products were 2,3-pinene epoxides (epoxides), cis- and trans-verbenol (verbenols), verbenone, and myrtenol.
Data overstates coupling due to impurities in substrate.

TABLE 17a

In vitro oxidation activity and selectivity of some CYP102A1 variants with (+)-α-pinene.

| Variant | N | C (%) | PFR | % (−)-2,3 | % (+)-2,3 | % cis-4-ol | % tr-4-ol | % 4-one | % 10-ol | % other |
|---|---|---|---|---|---|---|---|---|---|---|
| Wild-type (WT) | 41 | 0 | 0 | — | — | — | — | — | — | — |
| I401P (IP) | 1229 | 19 | 238 | 18 | 1 | 32 | 41.5 | 2 | 0.5 | 5 |
| F87A/IP | 1039 | 41 | 422 | 26.5 | 2 | 35 | 28 | 1.5 | 4.5 | 2.5 |
| RLYF/IP | 2770 | 41 | 1146 | 56.5 | 0.5 | 17.5 | 22.5 | 1.5 | 0.5 | 1 |
| RLYF/A330P/IP | 1294 | 29 | 373 | 78.5 | — | 9 | 5.5 | 4.5 | 0.5 | 2 |
| RLYF/A330P | 712 | 37 | 263 | 85 | 0.5 | 4 | 4.5 | 3.5 | 0.5 | 2 |

Rates are given in nmol · min⁻¹ · (nmol P450)⁻¹.
N = NADPH turnover rate.
C = coupling.
PFR = product formation rate.
Rates in nmol min⁻¹ (nmol P450)⁻¹.
Products were (−)-2,3-pinene epoxide ((−)-2,3), (+)-2,3-pinene epoxide ((+)-2,3), cis-verbenol (cis-4-ol), trans-verbenol (tr-4-ol), verbenone (4-one) and myrtenol (10-ol).

TABLE 18

In vitro oxidation activity and selectivity of CYP102A1 variants with fluorene.

| Variant | N | C (%) | PFR | % 9-ol | % 9-one |
|---|---|---|---|---|---|
| Wild-type (WT) | 7.9 | 0.9 | 0.1 | 71 | 29 |
| I401P (IP) | 1057 | 18 | 188 | 100 | — |
| Q403P | 277 | 7 | 19 | 100 | — |
| F87A/IP | 871 | 7.8 | 68 | 100 | — |
| RLYF/IP | 2283 | 26 | 582 | 100 | — |
| RLYF/A330P/IP | 2473 | 4.6 | 114 | 100 | — |
| RLYF/A330P | 510 | 3.6 | 18 | 100 | — |

N = NADPH turnover rate.
C = coupling.
PFR = product formation rate.
All rates in nmol min⁻¹ (nmol P450)⁻¹.
Products were 9-fluorenol (9-ol) and 2-fluorenone (9-one).

TABLE 19

In vitro oxidation activity and selectivity of CYP102A1 variants with β-ionone.

| Variant | N | C (%) | PFR | % 4-ol | % other |
|---|---|---|---|---|---|
| Wild-type (WT) | 241 | 34 | 82 | 100 | — |
| I401P (IP) | 3262 | 58 | 1894 | 98 | 2 |
| F87A/IP | 1190 | 38 | 450 | 99.5 | 0.5 |
| RLYF/IP | 3078 | 63 | 1949 | 99 | 1 |
| RLYF/A330P/IP | 1462 | 54 | 789 | 100 | — |
| RLYF/A330P | 727 | 51 | 373 | 100 | — |

N = NADPH turnover rate.
C = coupling.
PFR = product formation rate.
Rates are in nmol min⁻¹ (nmol P450)⁻¹.
Products were 4-hydroxy-β-ionone (4-ol).

TABLE 20

In vitro oxidation activity and selectivity of CYP102A1 variants with lauric (dodecanoic) acid.

| Variant | N | C (%) | PFR | % ω-1 | % ω-2 | % ω-3 | % ω-4 | % ω-5 | % other |
|---|---|---|---|---|---|---|---|---|---|
| Wild-type (WT) | 2777 | 52 | 1439 | 33.5 | 29 | 37 | 0.5 | — | — |
| I401P (IP) | 3812 | 53 | 2012 | 36 | 30.5 | 33 | 0.5 | — | — |
| F87A/IP | 1468 | 21 | 300 | 6 | 11 | 36.5 | 17.5 | 28.5 | 0.5 |
| RLYF/IP | 4410 | 44 | 1928 | 30.5 | 38.5 | 30 | 1 | — | — |

TABLE 20-continued

In vitro oxidation activity and selectivity of CYP102A1 variants with lauric (dodecanoic) acid.

| Variant | N | C (%) | PFR | % ω-1 | % ω-2 | % ω-3 | % ω-4 | % ω-5 | % other |
|---|---|---|---|---|---|---|---|---|---|
| RLYF/A330P/IP | 348 | 1.8 | 6.2 | 18 | 40 | 40 | 2 | — | — |
| RLYF/A330P | 47 | 0 | 0 | — | — | — | — | — | — |

N = NADPH turnover rate.
C = coupling.
PFR = product formation rate.
Rates in nmol min$^{-1}$ (nmol P450)$^{-1}$.
Products were 11-hydroxydodecanoic acid (ω-1), 10-hydroxydodecanoic acid (ω-2), 9-hydroxydodecanoic acid (ω-3), 8-hydroxydodecanoic acid (ω-4) and 7-hydroxydodecanoic acid (ω-5).

Sequence of the Invention (CYP102A1 wild type) (SEQ ID NO:1)

```
aca att aaa gaa atg cct cag cca aaa acg ttt gga gag ctt aaa      45
Thr Ile Lys Glu Met Pro Gln Pro Lys Thr Phe Gly Glu Leu Lys
1               5                   10                  15 aat tta ccg tta tta aac aca gat aaa ccg gtt caa gct ttg atg      90
Asn Leu Pro Leu Leu Asn Thr Asp Lys Pro Val Gln Ala Leu Met
                20                  25                  30 aaa att gcg gat gaa tta gga gaa atc ttt aaa ttc gag gcg cct      135
Lys Ile Ala Asp Glu Leu Gly Glu Ile Phe Lys Phe Glu Ala Pro
                35                  40                  45 ggt cgt gta acg cgc tac tta tca agt cag cgt cta att aaa gaa      180
Gly Arg Val Thr Arg Tyr Leu Ser Ser Gln Arg Leu Ile Lys Glu
                50                  55                  60 tgc gat gaa tca cgc ttt gat aaa aac tta agt caa gcg gca ctt      225
Ala Cys Asp Glu Ser Arg Phe Asp Lys Asn Leu Ser Gln Ala Leu
                65                  70                  75 aaa ttt gta cgt gat ttt gca gga gac ggg tta ttt aca agc tgg      270
Lys Phe Val Arg Asp Phe Ala Gly Asp Gly Leu Phe Thr Ser Trp
                80                  85                  90 acg cat gaa aaa aat tgg aaa aaa gcg cat aat atc tta ctt cca      315
Thr His Glu Lys Asn Trp Lys Lys Ala His Asn Ile Leu Leu Pro
                95                  100                 105 agc ttc agt cag cag gca atg aaa ggc tat cat gcg atg atg gtc      360
Ser Phe Ser Gln Gln Ala Met Lys Gly Tyr His Ala Met Met Val
                110                 115                 120 gat atc gcc gtg cag ctt gtt caa aag tgg gag cgt cta aat gca      405
Asp Ile Ala Val Gln Leu Val Gln Lys Trp Glu Arg Leu Asn Ala
                125                 130                 135 gat gag cat att gaa gta ccg gaa gac atg aca cgt tta acg ctt      450
Asp Glu His Ile Glu Val Pro Glu Asp Met Thr Arg Leu Thr Leu
                140                 145                 150 gat aca att ggt ctt tgc ggc ttt aac tat cgc ttt aac agc ttt      495
Asp Thr Ile Gly Leu Cys Gly Phe Asn Tyr Arg Phe Asn Per Phe
                155                 160                 165 tac cga gat cag cct cat cca ttt att aca agt atg gtc cgt gca      540
Tyr Arg Asp Gln Pro His Pro Phe Ile Thr Per Met Val Arg Ala
                170                 175                 180
```

```
ctg gat gaa gca atg aac aag ctg cag cga gca aat cca gac gac        585
Leu Asp Glu Ala Met Asn Lys Leu Gln Arg Ala Asn Pro Asp Asp
            185                 190                 195 cca gct tat gat gaa aac aag cgc cag ttt caa gaa gat atc aag        630
Pro Ala Tyr Asp Glu Asn Lys Arg Gln Phe Gln Glu Asp Ile Lys
            200                 205                 210 gtg atg aac gac cta gta gat aaa att att gca gat cgc aaa gca        675
Val Met Asn Asp Leu Val Asp Lys Ile Ile Ala Asp Arg Lys Ala
            215                 220                 225 agc ggt gaa caa agc gat gat tta tta acg cat atg cta aac gga        720
Ser Gly Glu Gln Ser Asp Asp Leu leu Thr His Met Leu Asn Gly
            230                 235                 240 aaa gat cca gaa acg ggt gag ccg ctt gat gac gag aac att cgc        765
Lys Asp Pro Glu Thr Gly Glu Pro Leu Asp Asp Glu Asn Ile Arg
            245                 250                 255 tat caa att att aca ttc tta att gcg gga cac gaa aca aca agt        810
Tyr Gln Ile Ile Thr Phe Leu Ile Ala Gly His Glu Thr Thr Ser
            260                 265                 270 ggt ctt tta tca ttt gcg ctg tat ttc tta gtg aaa aat cca cat        855
Gly Leu Leu Ser Phe Ala leu Tyr Phe Leu Val Lys Asn Pro His
            275                 280                 285 gta tta caa aaa gca gca gaa gaa gca gca cga gtt cta gta gat        900
Val Leu Gln Lys Ala Ala Glu Glu Ala Ala Arg Val Leu Val Asp
            290                 295                 300 cct gct cca agc tac aaa caa gtc aaa cag ctt aaa tat gtc ggc        945
Pro Val Pro Ser Tyr Lys Gln Val Lys Gln Leu Lys Tyr Val Gly
            305                 310                 315 atg gtc tta aac gaa gcg ctg cgc tta tgg cca act gct cct gcg        990
Met Val Leu Asn Glu Ala Leu Arg Leu Trp Pro Thr Ala Pro Ala
            320                 325                 330 ttt tcc cta tat gca aaa gaa gat acg gtg ctt gga gga gaa tat       1035
Phe Ser Leu Tyr Ala Lys Glu Asp Thr Val Leu Gly Gly Glu Tyr
            335                 340                 345 cct tta gaa aaa ggc gac gaa cta atg gtt ctg att cct cag ctt       1080
Pro Leu Glu Lys Gly Asp Glu Leu Met Val Leu Ile Pro Gln Leu
            350                 355                 360 cac cgt gat aaa aca att tgg gga gac gat gtg gaa gag ttc cgt       1125
His Arg Asp Lys Thr Ile Trp Gly Asp Asp Val Glu Glu Phe Arg
            365                 370                 375 cca gag cgt ttt gaa aat cca agt gcg att ccg cag cat gcg ttt       1170
Pro Glu Arg Phe Glu Asn Pro Ser Ala Ile Pro Gln His Ala Phe
            380                 385                 390 aaa ccg ttt gga aac ggt cag cgt gcg tgt atc ggt cag cag ttc       1215
Lys Pro Phe Gly Asn Gly Gln Arg Ala Cys Ile Gly Gln Gln Phe
            395                 400                 405 gct ctt cat gaa gca acg ctg gta ctt ggt atg atg cta aaa cac       1260
Ala Leu His Glu Ala Thr Leu Val Leu Gly Met Met Leu Lys His
            410                 415                 420
```

-continued

```
ttt gac ttt gaa gat cat aca aac tac gag ctg gat att aaa gaa    1305
Phe Asp Phe Glu Asp His Thr Asn Tyr Glu Leu Asp Ile Lys Glu
            425                 430                 435 act tta acg tta aaa cct gaa ggc ttt gtg gta aaa gca aaa tcg    1350
Thr Leu Thr Leu Lys Pro Glu Gly Phe Val Val Lys Ala Lys Ser
        440                 445                 450 aaa aaa att ccg ctt ggc ggt att cct tca cct agc act gaa cag    1395
Lys Lys Ile Pro Leu Gly Gly Ile Pro Ser Pro Ser Thr Glu Gln
        455                 460                 465 tct gcc aaa aaa gca cgc aaa aag gca gaa aac gct cat aat acg    1440
Ser Ala Lys Lys Val Arg Lys Lys Ala Glu Asn Ala His Asn Thr
        470                 475                 480 ccg ctg ctt gtg cta tac ggt tca aat atg gga aca gct gaa gga    1485
Pro Leu Leu Val Leu Tyr Gly Ser Asn Met Gly Thr Ala Glu Gly
        485                 490                 495 acg gcg cgt gat tta gca gat att gca atg agc aaa gga ttt gca    1530
Thr Ala Arg Asp Leu Ala Asp Ile Ala Met Ser Lys Gly Phe Ala
        500                 505                 510 ccg cag gtc gca acg ctt gat tca cac gcc gga aat ctt ccg cgc    1575
Pro Gln Val Ala Thr Leu Asp Ser His Ala Gly Asn Leu Pro Arg
        515                 520                 525 gaa gga gct gta tta att gta acg gcg tct tat aac ggt cat ccg    1620
Glu Gly Ala Val Leu Ile Val Thr Ala Ser Tyr Asn Gly His Pro
        530                 535                 540 cct gat aac gca aag caa ttt gtc gac tgg tta gac caa gcg tct    1665
Pro Asp Asn Ala Lys Gln Phe Val Asp Trp Leu Asp Gln Ala Ser
        545                 550                 555 gct gat gaa gta aaa ggc gtt cgc tac tcc gta ttt gga tgc ggc    1710
Ala Asp Glu Val Lys Gly Val Arg Tyr Ser Val Phe Gly Cys Gly
        560                 565                 570 gat aaa aac tgg gct act acg tat caa aaa gtg cct gct ttt atc    1755
Asp Lys Asn Trp Ala Thr Thr Tyr Gln Lys Val Pro Ala Phe Ile
        575                 580                 585 gat gaa acg ctt gcc gct aaa ggg gca gaa aac atc gct gac cgc    1800
Asp Glu Thr Leu Ala Ala Lys Gly Ala Glu Asn Ile Ala Asp Arg
        590                 595                 600 ggt gaa gca gat gca agc gac gac ttt gaa ggc aca tat gaa gaa    1845
Gly Glu Ala Asp Ala Ser Asp Asp Phe Glu Gly Thr Tyr Glu Glu
        605                 610                 615 tgg cgt gaa cat atg tgg agt gac gta gca gcc tac ttt aac ctc    1890
Trp Arg Glu His Met Trp Ser Asp Val Ala Ala Tyr Phe Asn Leu
        620                 625                 630 gac att gaa aac agt gaa gat aat aaa tct act ctt tca ctt caa    1935
Asp Ile Glu Asn Ser Glu Asp Asn Lys Ser Thr Leu Ser Leu Gln
        635                 640                 645 ttt gtc gac agc gcc gcg gat atg ccg ctt gcg aaa atg cac ggt    1980
Phe Val Asp Ser Ala Ala Asp Met Pro Leu Ala Lys Met His Gly
        650                 655                 660 gcg ttt tca acg aac gtc gta gca agc aaa gaa ctt caa cag cca    2025
```

-continued

```
                    Ala Phe Ser Thr Asn Val Val Ala Ser Lys Glu Leu Gln Gln Pro
                                    665                 670                 675 ggc agt gca cga agc acg cga cat ctt gaa att gaa ctt cca aaa         2070
Gly Ser Ala Arg Ser Thr Arg His Leu Glu Ile Glu Leu Pro Lys
                680                 685                 690 gaa gct tct tat caa gaa gga gat cat tta ggt gtt att cct cgc         2115
Glu Ala Ser Tyr Gln Glu Gly Asp His Leu Gly Val Ile Pro Arg
            695                 700                 705 aac tat gaa gga ata gta aac cgt gta aca gca agg ttc ggc cta         2160
Asn Tyr Glu Gly Ile Val Asn Arg Val Thr Ala Arg Phe Gly Leu
            710                 715                 720 gat gca tca cag caa atc cgt ctg gaa gca gaa gaa gaa aaa tta         2205
Asp Ala Ser Gln Gln Ile Arg Leu Glu Ala Glu Glu Glu Lys Leu
            725                 730                 735 gct cat ttg cca ctc gct aaa aca gta tcc gta gaa gag ctt ctg         2250
Ala His Leu Pro Leu Ala Lys Thr Val Ser Val Glu Glu Leu Leu
            740                 745                 750 caa tac gtg gag ctt caa gat cct gtt acg cgc acg cag ctt cgc         2295
Gln Tyr Val Glu Leu Gln Asp Pro Val Thr Arg Thr Gln Leu Arg
            755                 760                 765 gca atg gct gct aaa acg gtc tgc ccg ccg cat aaa gta gag ctt         2340
Ala Met Ala Ala Lys Thr Val Cys Pro Pro His Lys Val Glu Leu
            770                 775                 780 gaa gcc ttg ctt gaa aag caa gcc tac aaa gaa caa gtg ctg gca         2385
Glu Ala Leu Leu Glu Lys Gln Ala Tyr Lys Glu Gln Val Leu Ala
            785                 790                 795 aaa cgt tta aca atg ctt gaa ctg ctt gaa aaa tac ccg gcg tgt         2430
Lys Arg Leu Thr Met Leu Glu Leu Leu Glu Lys Tyr Pro Ala Cys
            800                 805                 810 gaa atg aaa ttc agc gaa ttt atc gcc ctt ctg cca agc ata cgc         2475
Glu Met Lys Phe Ser Glu Phe Ile Ala Leu Leu Pro Ser Ile Arg
            815                 820                 825 ccg cgc tat tac tcg att tct tca tca cct cgt gtc gat gaa aaa         2520
Pro Arg Tyr Tyr Ser Ile Ser Ser Ser Pro Arg Val Asp Glu Lys
            830                 835                 840 caa gca agc atc acg gtc agc gtt gtc tca gga gaa gcg tgg agc         2565
Gln Ala Ser Ile Thr Val Ser Val Val Ser Gly Glu Ala Trp Ser
            845                 850                 855 gga tat gga gaa tat aaa gga att gcg tcg aac tat ctt gcc gag         2610
Gly Tyr Gly Glu Tyr Lys Gly Ile Ala Ser Asn Tyr Leu Ala Glu
            860                 865                 870 ctg caa gaa gga gat acg att acg tgc ttt att tcc aca ccg cag         2655
Leu Gln Glu Gly Asp Thr Ile Thr Cys Phe Ile Ser Thr Pro Gln
            875                 880                 885 tca gaa ttt acg ctg cca aaa gac cct gaa acg ccg ctt atc atg         2700
Ser Glu Phe Thr Leu Pro Lys Asp Pro Glu Thr Pro Leu Ile Met
            890                 895                 900 gtc gga ccg gga aca ggc gtc gcg ccg ttt aga ggc ttt gtg cag         2745
```

```
Val Gly Pro Gly Thr Gly Val Ala Pro Phe Arg Gly Phe Val Gln
                905                 910                 915 gcg cgc aaa cag cta aaa gaa caa gga cag tca ctt gga gaa gca      2790
Ala Arg Lys Gln Leu Lys Glu Gln Gly Gln Ser Leu Gly Glu Ala
                920                 925                 930 cat tta tac ttc ggc tgc cgt tca cct cat gaa gac tat ctg tat      2835
His Leu Tyr Phe Gly Cys Arg Ser Pro His Glu Asp Tyr Leu Tyr
                935                 940                 945 caa gaa gag ctt gaa aac gcc caa agc gaa ggc atc att acg ctt      2880
Gln Glu Glu Leu Glu Asn Ala Gln Ser Glu Gly Ile Ile Thr Leu
                950                 955                 960 cat acc gct ttt tct cgc atg cca aat cag ccg aaa aca tac gtt      2925
His Thr Ala Phe Ser Arg Met Pro Asn Gln Pro Lys Thr Tyr Val
                965                 970                 975 cag cac gta atg gaa caa gac ggc aag aaa ttg att gaa ctt ctt      2970
Gln His Val Met Glu Gln Asp Gly Lys Lys Leu Ile Glu Leu Leu
                980                 985                 990 gat caa gga gcg cac ttc tat att tgc gga gac gga agc caa atg      3015
Asp Gln Gly Ala His Phe Tyr Ile Cys Gly Asp Gly Ser Gln Met
                995                 1000                1005 gca cct gcc gtt gaa gca acg ctt atg aaa agc tat gct gac gtt      3060
Ala Pro Ala Val Glu Ala Thr Leu Met Lys Ser Tyr Ala Asp Val
                1010                1015                1020 cac caa gtg agt gaa gca gac gct cgc tta tgg ctg cag cag cta      3105
His Gln Val Ser Glu Ala Asp Ala Arg Leu Trp Leu Gln Gln Leu
                1025                1030                1035 gaa gaa aaa ggc cga tac gca aaa gac gtg tgg gct ggg               3144
Glu Glu Lys Gly Arg Tyr Ala Lys Asp Val Trp Ala Gly
                1040                1045            1048
```

---

The invention claimed is:

1. A process for oxidizing a substrate which is an organic compound, comprising the step of oxidizing said organic compound substrate with a mutant CYP102A1 (Cytochrome P450 family 102 sub-family A member No. 1) enzyme, in the presence of NADPH and dioxygen, wherein said CYP102A1 enzyme comprises:
   (a) the amino acid sequence of SEQ ID NO: 2;
   (b) a homologue thereof of the CYP102 family; or
   (c) an amino acid sequence having at least 80% identity to the amino acid sequence of (a) or (b);
   in the presence of NADPH and dioxygen, wherein the mutant enzyme of (a), (b), or (c) comprises a substitution at one or more amino acid residue positions in the polypeptide chain corresponding to amino acid residue positions 330, 191, 401, 403, or 276 of SEQ ID NO: 2, thereby enhancing the monooxygenase activity of the mutant enzyme of (a), (b), or (c).

2. The process according to claim 1 wherein said substrate is a short-chain alkane, or a substituted derivative thereof, or is an aromatic compound, or an alkylbenzene, or a substituted derivative thereof, wherein a substituted derivative is capable of being oxidized by the mutant CYP102A1 (Cytochrome P450 family 102 sub-family A member No. 1) enzyme.

3. The process according to claim 1 wherein said substrate is a halo aromatic compound or an acyclic or cyclic terpene or a terpenoid or a sesquiterpene, or a cycloalkene or a saturated fatty acid; or a substituted derivative thereof, wherein a substituted derivative is capable of being oxidized by the mutant CYP102A1 (Cytochrome P450 family 102 sub-family A member No. 1) enzyme.

4. The process according to claim 2, wherein said short chain alkane is pentane, 3-methylpentane, 2-methylbutane, butane, propane, ethane and methane; or wherein said alkylbenzene is propylbenzene, ethylbenzene, toluene, butylbenzene, t-butylbenzene, o-xylene, m-xylene, cumene, p-cymene, and ethylanisole; or wherein the aromatic compound is naphthalene or fluorene; or wherein said monoterpene is limonene or pinene; or wherein said sesquiterpene is valencene; or wherein said terpenoid is an ionone such as β-ionone or a damascone; or wherein said saturated fatty acid is lauric acid or decanoic acid.

5. The process according to claim 1, wherein the organic compound substrate is oxidized in a cell which expresses said enzyme.

6. The process according to claim 1 wherein a different number of products are formed in comparison to if the process were carried out using CYP102A1 (Cytochrome P450 family 102 sub-family A, member No. 1).

7. The process according to claim 1, wherein said mutant enzyme shares at least 95% homology with amino acid residues 1-480 of SEQ ID NO: 2.

8. The process according to claim 1, wherein said mutant enzyme, which has:
   (i) a conservative mutation at one or more of positions 117, 131, 215, 330, 401; and/or
   (ii) a polar amino acid at one or more of positions 191 and 276; and/or
   (iii) a non-polar amino acid at one or more of positions 377 and 403; and/or
   (iv) an uncharged residue at position 425,
   and wherein optionally there are no mutations at positions which flank one or more of positions 117, 131, 191, 215, 276, 307, 330, 377, 401, 403 or 425.

9. The process according to claim 1, wherein said mutant enzyme has:
   (i) an amino acid with an increased side-chain volume at one or more of position 330, 401 and 403;
   (ii) a polar amino acid at one or more of positions 191 and 276; and/or
   (iii) a polar uncharged amino acid at position 425.

10. The process according to claim 1, wherein said mutant enzyme additionally comprises substitutions at one or more of the following positions: 47, 51, 74, 82, 87, 171, 188, 239, 259, 263, 264, 267, 319, 328 or 353.

11. The process according to claim 1, wherein said mutant enzyme comprises mutations selected from: R47L, Y51F, A74G, A82L, F87A, F87G, F87L, H171L, L188Q, N239H, I259V, I263A, A264G, E267V, N319Y, A328V or L353I.

12. The process according to claim 1, wherein said mutant enzyme comprises one or more of the following mutations or groups of mutations:
   (i) A330P;
   (ii) A191T/N239H/I259V/A276T/L353I;
   (iii) F87A/H171L/Q307H/N319Y;
   (iv) F87A/A330P/E377A/D425N;
   (v) F87A/A117V/E131D/L215I;
   (vi) I401P;
   (vii) R47L/Y51F/I401P;
   (viii) F87A/I401P;
   (ix) R47L/Y51F/F87A/I401P;
   (x) R47L/Y51F/A330P/I401P;
   (xi) Q403P;
   (xii) R47L/Y51F/Q403P;
   (xiii) R47L/Y51F/F87A/Q403P.

* * * * *